(12) United States Patent
Meridew et al.

(10) Patent No.: US 10,507,029 B2
(45) Date of Patent: Dec. 17, 2019

(54) PATIENT-SPECIFIC ACETABULAR GUIDES AND ASSOCIATED INSTRUMENTS

(71) Applicant: Biomet Manufacturing, LLC, Warsaw, IN (US)

(72) Inventors: Jason D. Meridew, Warsaw, IN (US); Tyler D. Witt, Warsaw, IN (US); Ryan John Schoenefeld, Fort Wayne, IN (US); William Jason Slone, Silver Lake, IN (US); Adolph V. Lombardi, New Albany, OH (US); Jeffrey H. Nycz, Warsaw, IN (US); Matthew D. Munsterman, Warsaw, IN (US); Alexander P. Wolfe, West Lafayette, IN (US); Tamon Kabata, Kanazawa (JP); James Nairus, Bolton, MA (US); John C. Clohisy, St. Louis, MO (US)

(73) Assignee: Biomet Manufacturing, LLC, Warsaw, IN (US)

( * ) Notice: Subject to any disclaimer, the term of this patent is extended or adjusted under 35 U.S.C. 154(b) by 348 days.

(21) Appl. No.: 15/130,414

(22) Filed: Apr. 15, 2016

(65) Prior Publication Data

US 2016/0228133 A1    Aug. 11, 2016

Related U.S. Application Data

(62) Division of application No. 13/400,652, filed on Feb. 21, 2012, now Pat. No. 9,339,278.
(Continued)

(51) Int. Cl.
*A61B 17/00* (2006.01)
*A61B 17/17* (2006.01)
(Continued)

(52) U.S. Cl.
CPC ...... *A61B 17/1746* (2013.01); *A61B 17/1659* (2013.01); *A61B 17/1666* (2013.01);
(Continued)

(58) Field of Classification Search
CPC combination set(s) only.
See application file for complete search history.

(56) References Cited

U.S. PATENT DOCUMENTS

| | | |
|---|---|---|
| 1,480,285 A | 1/1924 | Moore |
| 1,763,730 A | 6/1930 | Lackum |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

"U.S. Appl. No. 12/255,945, Appeal Decision mailed Feb. 27, 2017", 12 pgs.

(Continued)

*Primary Examiner* — Sameh R Boles
(74) *Attorney, Agent, or Firm* — Schwegman Lundberg & Woessner, P.A.

(57) ABSTRACT

A patient-specific acetabular guide can be used for preparing an acetabulum of a patient to receive an acetabular implant. The acetabular guide includes a patient-specific engagement surface designed to be complementary and mateable with a corresponding surface of the patient's pelvic anatomy. The acetabular guide is designed during a pre-operative plan for the patient by a three-dimensional reconstruction of the anatomy of the patient using two-dimensional medical images. The patient-specific engagement surface has a first portion mateable with a portion of the acetabulum of the patient. The acetabular guide includes a guiding element that
(Continued)

extends from the acetabular guide opposite to the first portion of engagement surface. The guiding element defines a bore designed to be oriented along an alignment axis for an acetabular implant when the acetabular guide is engaged to the acetabulum.

2 Claims, 23 Drawing Sheets

Related U.S. Application Data

(60) Provisional application No. 61/446,660, filed on Feb. 25, 2011.

(51) Int. Cl.
    *A61B 17/16*     (2006.01)
    *A61F 2/46*     (2006.01)
    *A61B 90/00*     (2016.01)
    *A61B 34/10*     (2016.01)

(52) U.S. Cl.
CPC ........ *A61F 2/4609* (2013.01); *A61B 17/1617* (2013.01); *A61B 17/1735* (2013.01); *A61B 2034/108* (2016.02); *A61B 2090/034* (2016.02); *A61F 2002/4687* (2013.01); *F04C 2270/041* (2013.01)

(56) References Cited

U.S. PATENT DOCUMENTS

| | | |
|---|---|---|
| 1,959,615 A | 5/1934 | Derrah |
| 2,181,746 A | 11/1939 | Siebrandt |
| 2,407,845 A | 9/1946 | Orisan |
| 2,416,228 A | 2/1947 | Sheppard |
| 2,433,815 A | 12/1947 | Nicephore |
| 2,455,655 A | 12/1948 | Carroll |
| 2,618,913 A | 11/1952 | Plancon et al. |
| 2,702,550 A | 2/1955 | Rowe |
| 2,724,326 A | 11/1955 | Long |
| 2,910,978 A | 11/1959 | Urist |
| 2,955,530 A | 10/1960 | Nilo |
| 3,048,522 A | 8/1962 | Velley |
| 3,229,006 A | 1/1966 | Egon |
| 3,229,372 A | 1/1966 | Quashnock et al. |
| 3,330,611 A | 7/1967 | Heifetz |
| 3,514,791 A | 6/1970 | Sparks |
| 3,554,197 A | 1/1971 | Dobbie |
| 3,624,747 A | 11/1971 | Mcknight et al. |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee et al. |
| 3,840,904 A | 10/1974 | Tronzo |
| 3,869,731 A | 3/1975 | Waugh et al. |
| 3,903,549 A | 9/1975 | Deyerle |
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon et al. |
| 3,975,858 A | 8/1976 | Much |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,219,939 A | 9/1980 | Turen |
| 4,246,895 A | 1/1981 | Rehder |
| 4,299,224 A | 11/1981 | Noiles |
| 4,304,178 A | 12/1981 | Haberle |
| 4,306,866 A | 12/1981 | Weissman |
| 4,311,145 A | 1/1982 | Esty et al. |
| 4,324,006 A | 4/1982 | Charnley |
| 4,344,193 A | 8/1982 | Kenny |
| 4,349,018 A | 9/1982 | Chamber |
| 4,373,709 A | 2/1983 | Whitt et al. |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| 4,421,112 A | 12/1983 | Mains et al. |
| 4,428,571 A | 1/1984 | Sugarman |
| 4,436,684 A | 3/1984 | White |
| D273,895 S | 5/1984 | Kenna et al. |
| D274,091 S | 5/1984 | Kenna |
| 4,453,421 A | 6/1984 | Umano |
| 4,457,306 A | 7/1984 | Borzone |
| 4,475,549 A | 10/1984 | Oh |
| 4,501,269 A | 2/1985 | Bagby |
| 4,506,393 A | 3/1985 | Murphy |
| 4,509,518 A | 4/1985 | Mcgarry et al. |
| 4,516,276 A | 5/1985 | Mittelmeier |
| 4,524,766 A | 6/1985 | Petersen |
| 4,528,980 A | 7/1985 | Kenna |
| 4,534,365 A | 8/1985 | Bonetta et al. |
| 4,535,773 A | 8/1985 | Yoon |
| 4,545,375 A | 10/1985 | Cline |
| 4,554,686 A | 11/1985 | Baker |
| 4,562,598 A | 1/1986 | Kranz |
| 4,565,191 A | 1/1986 | Slocum |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,619,658 A | 10/1986 | Pappas et al. |
| 4,621,630 A | 11/1986 | Kenna |
| 4,624,254 A | 11/1986 | Mcgarry et al. |
| 4,632,111 A | 12/1986 | Roche |
| 4,633,862 A | 1/1987 | Petersen |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,663,720 A | 5/1987 | Duret et al. |
| 4,678,470 A | 7/1987 | Nashef et al. |
| 4,682,598 A | 7/1987 | Beraha |
| 4,685,460 A | 8/1987 | Thornton |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,711,233 A | 12/1987 | Brown |
| 4,715,860 A | 12/1987 | Amstutz et al. |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,722,330 A | 2/1988 | Russell et al. |
| 4,739,751 A | 4/1988 | Sapega et al. |
| 4,759,350 A | 7/1988 | Dunn et al. |
| 4,778,474 A | 10/1988 | Homsy |
| 4,794,854 A | 1/1989 | Swaim |
| 4,800,874 A | 1/1989 | David et al. |
| 4,817,602 A | 4/1989 | Beraha |
| 4,821,213 A | 4/1989 | Cline et al. |
| 4,822,365 A | 4/1989 | Walker et al. |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |

(56) References Cited

U.S. PATENT DOCUMENTS

| | | |
|---|---|---|
| 4,863,472 A | 9/1989 | Tormala et al. |
| 4,871,975 A | 10/1989 | Nawata et al. |
| 4,888,022 A | 12/1989 | Huebsch |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,911,721 A | 3/1990 | Andergaten |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker et al. |
| 4,950,296 A | 8/1990 | Mcintyre |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | Hodorek |
| 4,985,037 A | 1/1991 | Petersen |
| 4,985,038 A | 1/1991 | Lyell |
| 4,994,064 A | 2/1991 | Aboczky |
| 5,002,579 A | 3/1991 | Copf et al. |
| 5,006,121 A | 4/1991 | Hafeli |
| 5,007,912 A | 4/1991 | Albrektsson et al. |
| 5,007,936 A | 4/1991 | Woolson |
| 5,015,247 A | 5/1991 | Michelson |
| 5,019,105 A | 5/1991 | Wiley |
| 5,030,219 A | 7/1991 | Matsen et al. |
| 5,030,221 A | 7/1991 | Buechel et al. |
| 5,032,132 A | 7/1991 | Matsen, III et al. |
| 5,035,700 A | 7/1991 | Kenna |
| 5,037,424 A | 8/1991 | Aboczsky |
| 5,041,117 A | 8/1991 | Engelhardt |
| 5,053,037 A | 10/1991 | Lackey et al. |
| 5,053,039 A | 10/1991 | Hofmann et al. |
| 5,056,351 A | 10/1991 | Stiver et al. |
| 5,060,678 A | 10/1991 | Bauman et al. |
| 5,061,270 A | 10/1991 | Aboczky |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,086,401 A | 2/1992 | Glassman et al. |
| 5,092,869 A | 3/1992 | Waldron et al. |
| 5,098,383 A | 3/1992 | Hemmy et al. |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,425 A | 4/1992 | Hwang |
| 5,108,441 A | 4/1992 | Mcdowell |
| 5,111,987 A | 5/1992 | Moeinzadeh et al. |
| 5,122,144 A | 6/1992 | Bert et al. |
| 5,123,906 A | 6/1992 | Kelman |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,141,512 A | 8/1992 | Farmer et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,176,711 A | 1/1993 | Grimes |
| 5,178,622 A | 1/1993 | Lehner, II |
| 5,183,053 A | 2/1993 | Yeh |
| 5,183,464 A | 2/1993 | Dubrul et al. |
| 5,186,178 A | 2/1993 | Yeh |
| 5,192,327 A | 3/1993 | Brantigan |
| 5,194,066 A | 3/1993 | Van Zile |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,222,984 A | 6/1993 | Forte |
| 5,228,459 A | 7/1993 | Caspari et al. |
| 5,234,433 A | 8/1993 | Bert et al. |
| 5,242,448 A | 9/1993 | Pettine et al. |
| 5,246,444 A | 9/1993 | Schreiber |
| 5,253,506 A | 10/1993 | Davis et al. |
| 5,258,004 A | 11/1993 | Bales et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| 5,274,565 A | 12/1993 | Reuben |
| D343,247 S | 1/1994 | Walen |
| 5,275,166 A | 1/1994 | Vaitekunas et al. |
| 5,275,603 A | 1/1994 | Ferrante et al. |
| 5,282,802 A | 2/1994 | Mahony, III |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,299,288 A | 3/1994 | Glassman et al. |
| 5,300,077 A | 4/1994 | Howell |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,323,697 A | 6/1994 | Schrock |
| 5,329,845 A | 7/1994 | Bichel |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Bonutti |
| 5,360,446 A | 11/1994 | Kennedy |
| 5,364,402 A | 11/1994 | Mumme et al. |
| 5,368,599 A | 11/1994 | Hirsch et al. |
| 5,368,858 A | 11/1994 | Hunziker |
| 5,370,692 A | 12/1994 | Fink et al. |
| 5,370,699 A | 12/1994 | Hood et al. |
| 5,379,133 A | 1/1995 | Kirk |
| 5,382,249 A | 1/1995 | Fletcher et al. |
| 5,383,937 A | 1/1995 | Mikhail |
| 5,390,683 A | 2/1995 | Pisharodi |
| 5,395,376 A | 2/1995 | Pisharodi |
| 5,405,395 A | 4/1995 | Coates |
| 5,408,409 A | 4/1995 | Glassman et al. |
| D358,647 S | 5/1995 | Cohen et al. |
| 5,411,521 A | 5/1995 | Putnam et al. |
| 5,415,662 A | 5/1995 | Ferrante et al. |
| 5,417,694 A | 5/1995 | Marik et al. |
| 5,423,827 A | 6/1995 | Mumme et al. |
| 5,425,355 A | 6/1995 | Kulick |
| 5,425,745 A | 6/1995 | Green et al. |
| 5,438,263 A | 8/1995 | Dworkin et al. |
| 5,440,496 A | 8/1995 | Andersson et al. |

(56) References Cited

U.S. PATENT DOCUMENTS

| | | |
|---|---|---|
| 5,443,475 A | 8/1995 | Auerbach et al. |
| 5,445,639 A | 8/1995 | Kuslich et al. |
| 5,445,642 A | 8/1995 | McNulty et al. |
| 5,448,489 A | 9/1995 | Reuben |
| 5,449,360 A | 9/1995 | Schreiber |
| 5,452,407 A | 9/1995 | Crook |
| 5,454,365 A | 10/1995 | Bonutti |
| 5,454,815 A | 10/1995 | Geisser et al. |
| 5,454,816 A | 10/1995 | Ashby |
| 5,456,268 A | 10/1995 | Bonutti |
| 5,462,550 A | 10/1995 | Dietz et al. |
| 5,472,415 A | 12/1995 | King et al. |
| 5,474,559 A | 12/1995 | Bertin et al. |
| 5,484,095 A | 1/1996 | Green et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | Defonzo et al. |
| 5,507,763 A | 4/1996 | Petersen et al. |
| 5,507,833 A | 4/1996 | Bohn |
| 5,514,139 A | 5/1996 | Goldstein et al. |
| 5,514,143 A | 5/1996 | Bonutti et al. |
| 5,514,519 A | 5/1996 | Neckers |
| 5,520,692 A | 5/1996 | Ferrante |
| 5,520,694 A | 5/1996 | Dance et al. |
| 5,520,695 A | 5/1996 | Luckman |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,546,720 A | 8/1996 | Labruzza |
| 5,549,683 A | 8/1996 | Bonutti |
| 5,549,688 A | 8/1996 | Ries et al. |
| 5,554,169 A | 9/1996 | Green et al. |
| 5,554,190 A | 9/1996 | Draenert |
| 5,560,096 A | 10/1996 | Stephens |
| 5,560,728 A | 10/1996 | Mcfadden |
| 5,562,675 A | 10/1996 | Mcnulty et al. |
| 5,569,163 A | 10/1996 | Francis et al. |
| 5,569,261 A | 10/1996 | Marik et al. |
| 5,570,700 A | 11/1996 | Vogeler |
| 5,571,110 A | 11/1996 | Matsen, III et al. |
| 5,571,111 A | 11/1996 | Aboczky |
| 5,578,037 A | 11/1996 | Sanders et al. |
| 5,578,039 A | 11/1996 | Vendrely et al. |
| 5,586,558 A | 12/1996 | Riley |
| 5,593,411 A | 1/1997 | Stalcup et al. |
| 5,593,448 A | 1/1997 | Dong |
| 5,595,703 A | 1/1997 | Swaelens et al. |
| 5,597,379 A | 1/1997 | Haines et al. |
| 5,601,565 A | 2/1997 | Huebner |
| 5,607,431 A | 3/1997 | Dudasik et al. |
| 5,608,052 A | 3/1997 | Zmitek et al. |
| 5,609,603 A | 3/1997 | Linden |
| 5,611,802 A | 3/1997 | Samuelson et al. |
| 5,613,969 A | 3/1997 | Jenkins, Jr. |
| 5,616,147 A | 4/1997 | Gadelius |
| 5,620,448 A | 4/1997 | Puddu |
| 5,624,444 A | 4/1997 | Wixon et al. |
| 5,624,463 A | 4/1997 | Stone et al. |
| 5,632,745 A | 5/1997 | Schwartz |
| 5,634,927 A | 6/1997 | Houston et al. |
| 5,641,323 A | 6/1997 | Caldarise |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,658,294 A | 8/1997 | Sederholm |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| 5,671,018 A | 9/1997 | Ohara et al. |
| D385,163 S | 10/1997 | Hutchins et al. |
| 5,676,668 A | 10/1997 | McCue et al. |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,398 A | 11/1997 | Carls et al. |
| 5,683,469 A | 11/1997 | Johnson et al. |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,694,693 A | 12/1997 | Hutchins et al. |
| 5,697,933 A | 12/1997 | Gundlapalli et al. |
| 5,702,447 A | 12/1997 | Walch et al. |
| 5,702,460 A | 12/1997 | Carls et al. |
| 5,702,464 A | 12/1997 | Lackey et al. |
| 5,702,475 A | 12/1997 | Zahedi |
| 5,704,941 A | 1/1998 | Jacober et al. |
| 5,707,350 A | 1/1998 | Krause et al. |
| 5,709,689 A | 1/1998 | Ferrante et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliot et al. |
| 5,722,978 A | 3/1998 | Jenkins, Jr. |
| 5,723,331 A | 3/1998 | Tubo et al. |
| 5,725,376 A | 3/1998 | Poirier |
| 5,725,592 A | 3/1998 | White et al. |
| 5,725,593 A | 3/1998 | Caracciolo |
| 5,728,128 A | 3/1998 | Crickenberger et al. |
| 5,733,292 A | 3/1998 | Gustilo et al. |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,755,731 A | 5/1998 | Grinberg |
| 5,755,791 A | 5/1998 | Whitson et al. |
| 5,755,803 A | 5/1998 | Haines et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,769,855 A | 6/1998 | Bertin et al. |
| 5,769,899 A | 6/1998 | Schwartz et al. |
| 5,772,594 A | 6/1998 | Barrick |
| 5,776,200 A | 7/1998 | Johnson et al. |
| 5,786,217 A | 7/1998 | Tubo et al. |
| 5,788,700 A | 8/1998 | Morawa et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,810,827 A | 9/1998 | Haines et al. |
| 5,810,831 A | 9/1998 | D'Antonio |
| 5,817,097 A | 10/1998 | Howard et al. |
| 5,817,109 A | 10/1998 | Mcgarry et al. |
| 5,824,083 A | 10/1998 | Draenert |
| 5,835,619 A | 11/1998 | Morimoto et al. |
| 5,842,477 A | 12/1998 | Naughton et al. |
| 5,846,931 A | 12/1998 | Hattersley et al. |
| 5,860,980 A | 1/1999 | Axelson, Jr. et al. |
| 5,860,981 A | 1/1999 | Bertin et al. |
| 5,866,415 A | 2/1999 | Villeneuve |
| 5,871,018 A | 2/1999 | Delp et al. |
| 5,871,493 A | 2/1999 | Sjostrom et al. |
| 5,876,456 A | 3/1999 | Sederholm et al. |
| 5,879,354 A | 3/1999 | Haines et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia, III et al. |
| 5,885,297 A | 3/1999 | Matsen |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,899,914 A | 5/1999 | Zirps et al. |

(56) References Cited

U.S. PATENT DOCUMENTS

| | | |
|---|---|---|
| 5,901,060 A | 5/1999 | Schall et al. |
| 5,902,340 A | 5/1999 | White et al. |
| 5,908,424 A | 6/1999 | Bertin et al. |
| 5,911,723 A | 6/1999 | Ashby et al. |
| 5,911,724 A | 6/1999 | Wehrli |
| 5,913,874 A | 6/1999 | Berns et al. |
| 5,916,219 A | 6/1999 | Matsuno et al. |
| 5,921,988 A | 7/1999 | Legrand |
| 5,921,990 A | 7/1999 | Webb |
| 5,925,049 A | 7/1999 | Gustilo et al. |
| 5,925,077 A | 7/1999 | Williamson et al. |
| 5,942,370 A | 8/1999 | Neckers |
| 5,961,499 A | 10/1999 | Bonutti et al. |
| 5,967,777 A | 10/1999 | Klein et al. |
| 5,976,149 A | 11/1999 | Masini |
| 5,980,526 A | 11/1999 | Johnson et al. |
| 5,995,738 A | 11/1999 | DiGioia, III et al. |
| 5,997,566 A | 12/1999 | Tobin |
| 6,002,859 A | 12/1999 | DiGioia, III et al. |
| 6,007,537 A | 12/1999 | Burkinshaw et al. |
| 6,008,433 A | 12/1999 | Stone |
| 6,012,456 A | 1/2000 | Schuerch |
| 6,013,081 A | 1/2000 | Burkinshaw et al. |
| 6,015,419 A | 1/2000 | Strome et al. |
| 6,019,767 A | 2/2000 | Howell |
| 6,022,350 A | 2/2000 | Ganem |
| 6,022,356 A | 2/2000 | Noyes et al. |
| 6,024,746 A | 2/2000 | Katz |
| 6,033,415 A | 3/2000 | Mittelstadt et al. |
| 6,042,612 A | 3/2000 | Voydeville |
| 6,056,754 A | 5/2000 | Haines et al. |
| 6,056,756 A | 5/2000 | Eng et al. |
| 6,059,789 A | 5/2000 | Dinger |
| 6,059,817 A | 5/2000 | Bonutti et al. |
| 6,059,831 A | 5/2000 | Braslow et al. |
| 6,059,833 A | 5/2000 | Doets |
| 6,063,095 A | 5/2000 | Wang et al. |
| 6,066,175 A | 5/2000 | Henderson et al. |
| 6,077,270 A | 6/2000 | Katz |
| 6,077,287 A | 6/2000 | Taylor et al. |
| 6,086,593 A | 7/2000 | Bonutti |
| 6,090,122 A | 7/2000 | Sjostrom et al. |
| 6,096,043 A | 8/2000 | Techiera et al. |
| 6,099,531 A | 8/2000 | Bonutti |
| 6,099,532 A | 8/2000 | Florea |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,132,469 A | 10/2000 | Schroeder |
| 6,132,472 A | 10/2000 | Bonutti |
| 6,136,033 A | 10/2000 | Suemer |
| 6,156,069 A | 12/2000 | Amstutz |
| 6,156,070 A | 12/2000 | Incavo et al. |
| 6,159,217 A | 12/2000 | Robie et al. |
| 6,159,246 A | 12/2000 | Mendes et al. |
| 6,161,080 A | 12/2000 | Aouni-Ateshian et al. |
| 6,162,257 A | 12/2000 | Gustilo et al. |
| 6,165,223 A | 12/2000 | Metzger et al. |
| 6,171,340 B1 | 1/2001 | Mcdowell et al. |
| 6,174,321 B1 | 1/2001 | Webb |
| 6,185,315 B1 | 2/2001 | Schmucker et al. |
| 6,187,010 B1 | 2/2001 | Masini |
| 6,187,023 B1 | 2/2001 | Bonutti |
| 6,195,158 B1 | 2/2001 | Cadell et al. |
| 6,195,615 B1 | 2/2001 | Lysen |
| 6,197,064 B1 | 3/2001 | Haines et al. |
| 6,198,794 B1 | 3/2001 | Peshkin et al. |
| 6,203,546 B1 | 3/2001 | Macmahon |
| 6,205,411 B1 | 3/2001 | Digioia, III et al. |
| 6,206,927 B1 | 3/2001 | Fell et al. |
| 6,210,445 B1 | 4/2001 | Zawadzki |
| 6,211,976 B1 | 4/2001 | Popovich et al. |
| 6,214,051 B1 | 4/2001 | Badorf et al. |
| 6,228,121 B1 | 5/2001 | Khalili |
| 6,238,435 B1 | 5/2001 | Meulink et al. |
| 6,254,604 B1 | 7/2001 | Howell |
| 6,258,097 B1 | 7/2001 | Cook et al. |
| 6,258,127 B1 | 7/2001 | Schmotzer |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,277,136 B1 | 8/2001 | Bonutti et al. |
| 6,290,703 B1 | 9/2001 | Ganem |
| 6,290,704 B1 | 9/2001 | Burkinshaw et al. |
| 6,290,727 B1 | 9/2001 | Otto et al. |
| 6,293,971 B1 | 9/2001 | Nelson et al. |
| 6,301,495 B1 | 10/2001 | Gueziec et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,806 B1 | 12/2001 | Fox |
| 6,325,829 B1 | 12/2001 | Schmotzer |
| 6,327,491 B1 | 12/2001 | Franklin et al. |
| 6,328,572 B1 | 12/2001 | Higashida et al. |
| 6,338,737 B1 | 1/2002 | Toledano |
| 6,338,738 B1 | 1/2002 | Bellotti et al. |
| 6,343,987 B2 | 2/2002 | Hayama et al. |
| 6,354,011 B1 | 3/2002 | Albrecht |
| 6,358,266 B1 | 3/2002 | Bonutti |
| 6,361,506 B1 | 3/2002 | Saenger et al. |
| 6,361,563 B2 | 3/2002 | Terrill-Grisoni et al. |
| 6,361,565 B1 | 3/2002 | Bonutti |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,040 B1 | 5/2002 | Christoudias |
| 6,391,251 B1 | 5/2002 | Keicher et al. |
| 6,395,005 B1 | 5/2002 | Lovell |
| 6,406,495 B1 | 6/2002 | Schoch |
| 6,409,722 B1 | 6/2002 | Hoey et al. |
| 6,413,279 B1 | 7/2002 | Metzger et al. |
| 6,416,553 B1 | 7/2002 | White et al. |
| 6,423,063 B1 | 7/2002 | Bonutti |
| 6,423,068 B1 | 7/2002 | Reisberg et al. |
| 6,424,332 B1 | 7/2002 | Powell |
| 6,427,698 B1 | 8/2002 | Yoon et al. |
| 6,428,541 B1 | 8/2002 | Boyd et al. |
| 6,431,743 B1 | 8/2002 | Mizutani et al. |
| D462,767 S | 9/2002 | Meyer et al. |
| 6,447,448 B1 | 9/2002 | Ishikawa et al. |
| 6,458,135 B1 | 10/2002 | Harwin et al. |
| 6,459,948 B1 | 10/2002 | Ateshian et al. |
| 6,463,351 B1 | 10/2002 | Clynch |
| 6,468,280 B1 | 10/2002 | Saenger et al. |
| 6,468,289 B1 | 10/2002 | Bonutti |
| 6,475,243 B1 | 11/2002 | Sheldon et al. |
| 6,478,799 B1 | 11/2002 | Williamson |
| 6,482,209 B1 | 11/2002 | Engh et al. |
| 6,482,236 B2 | 11/2002 | Habecker |
| 6,488,715 B1 | 12/2002 | Pope et al. |
| 6,500,181 B1 | 12/2002 | Portney |
| 6,503,255 B1 | 1/2003 | Albrektsson et al. |
| 6,503,267 B2 | 1/2003 | Bonutti et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,554,838 B2 | 4/2003 | Mcgovern et al. |
| 6,556,008 B2 | 4/2003 | Thesen |
| 6,558,391 B2 | 5/2003 | Axelson, Jr. et al. |

(56) References Cited

U.S. PATENT DOCUMENTS

| | | |
|---|---|---|
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,583,630 B2 | 6/2003 | Mendes et al. |
| 6,589,283 B1 | 7/2003 | Metzger et al. |
| 6,591,581 B2 | 7/2003 | Schmieding |
| 6,602,259 B1 | 8/2003 | Masini |
| 6,605,293 B1 | 8/2003 | Giordano et al. |
| 6,610,067 B2 | 8/2003 | Tallarida et al. |
| 6,610,096 B2 | 8/2003 | MacDonald |
| 6,620,181 B1 | 9/2003 | Bonutti |
| 6,622,567 B1 | 9/2003 | Hamel et al. |
| 6,629,999 B1 | 10/2003 | Serafin, Jr. |
| 6,632,225 B2 | 10/2003 | Sanford et al. |
| 6,635,073 B2 | 10/2003 | Bonutti |
| 6,641,617 B1 | 11/2003 | Merrill et al. |
| 6,673,077 B1 | 1/2004 | Katz |
| 6,676,662 B1 | 1/2004 | Bagga et al. |
| 6,676,892 B2 | 1/2004 | Das et al. |
| 6,682,566 B2 | 1/2004 | Draenert et al. |
| 6,682,567 B1 | 1/2004 | Schroeder |
| 6,695,848 B2 | 2/2004 | Haines |
| 6,696,073 B2 | 2/2004 | Boyce et al. |
| 6,697,664 B2 | 2/2004 | Kienzle, III et al. |
| 6,699,289 B2 | 3/2004 | Iannotti et al. |
| 6,701,174 B1 | 3/2004 | Krause et al. |
| 6,702,821 B2 | 3/2004 | Bonutti |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,743,235 B2 | 6/2004 | Subba Rao |
| 6,746,487 B2 | 6/2004 | Scifert et al. |
| 6,749,638 B1 | 6/2004 | Saladino |
| 6,750,653 B1 | 6/2004 | Zou X et al. |
| 6,770,078 B2 | 8/2004 | Bonutti |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,810,753 B2 | 11/2004 | Valdevit et al. |
| 6,821,299 B2 | 11/2004 | Kirking et al. |
| 6,823,871 B2 | 11/2004 | Schmieding |
| 6,827,723 B2 | 12/2004 | Carson |
| 6,871,549 B2 | 3/2005 | Serra et al. |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,975,755 B1 | 12/2005 | Baumberg |
| 6,979,299 B2 | 12/2005 | Peabody et al. |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,001,393 B2 | 2/2006 | Schwenke et al. |
| 7,022,141 B2 | 4/2006 | Dwyer et al. |
| 7,029,477 B2 | 4/2006 | Grimm |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,995 B2 | 9/2006 | Crofford |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,172,599 B2 | 2/2007 | Steffensmeier et al. |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,261,719 B1 | 8/2007 | Twomey et al. |
| 7,275,218 B2 | 9/2007 | Petrella et al. |
| 7,282,054 B2 | 10/2007 | Steffensmeier et al. |
| 7,291,117 B2 | 11/2007 | Boecker et al. |
| 7,291,177 B2 | 11/2007 | Gibbs |
| 7,294,133 B2 | 11/2007 | Zink et al. |
| 7,297,164 B2 | 11/2007 | Johnson et al. |
| 7,309,339 B2 | 12/2007 | Cusick et al. |
| 7,331,965 B2 | 2/2008 | Nielsen |
| 7,333,013 B2 | 2/2008 | Berger |
| 7,335,207 B1 | 2/2008 | Smith |
| 7,335,231 B2 | 2/2008 | Mclean |
| 7,338,499 B1 | 3/2008 | Kuczynski et al. |
| 7,371,260 B2 | 5/2008 | Malinin |
| 7,377,182 B2 | 5/2008 | Serra et al. |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De |
| 7,419,492 B2 | 9/2008 | Yoon et al. |
| 7,427,200 B2 | 9/2008 | Noble et al. |
| 7,427,272 B2 | 9/2008 | Richard et al. |
| 7,458,989 B2 | 12/2008 | Banks |
| 7,465,320 B1 | 12/2008 | Kito et al. |
| 7,468,075 B2 | 12/2008 | Lang et al. |
| 7,474,223 B2 | 1/2009 | Nycz et al. |
| 7,488,324 B1 | 2/2009 | Metzger et al. |
| 7,488,325 B2 | 2/2009 | Qian et al. |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kleman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,636,595 B2 | 12/2009 | Marquart |
| 7,646,161 B2 | 1/2010 | Albu-schäffer et al. |
| 7,651,501 B2 | 1/2010 | Penenberg et al. |
| 7,660,623 B2 | 2/2010 | Hunter et al. |
| 7,670,345 B2 | 3/2010 | Plassky et al. |
| 7,674,100 B2 | 3/2010 | Hayes-pankhurst et al. |
| 7,682,398 B2 | 3/2010 | Croxton et al. |
| 7,695,477 B2 | 4/2010 | Creger et al. |

(56) References Cited

U.S. PATENT DOCUMENTS

| | | |
|---|---|---|
| 7,695,521 B2 | 4/2010 | Ely et al. |
| 7,699,847 B2 | 4/2010 | Sheldon et al. |
| 7,702,380 B1 | 4/2010 | Dean |
| 7,704,253 B2 | 4/2010 | Bastian et al. |
| 7,723,395 B2 | 5/2010 | Ringeisen et al. |
| 7,747,305 B2 | 6/2010 | Dean et al. |
| 7,752,690 B1 | 7/2010 | Seth |
| D622,854 S | 8/2010 | Otto et al. |
| 7,780,672 B2 | 8/2010 | Metzger et al. |
| 7,780,681 B2 | 8/2010 | Sarin et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,040 B2 | 11/2010 | Ward et al. |
| 7,837,690 B2 | 11/2010 | Metzger |
| 7,846,382 B2 | 12/2010 | Strand |
| 7,850,698 B2 | 12/2010 | Straszheim-Morley et al. |
| 7,854,737 B2 | 12/2010 | Daniels et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roßner et al. |
| 8,057,482 B2 | 11/2011 | Stone et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,109,942 B2 | 2/2012 | Carson |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,823 B2 | 5/2012 | Nycz et al. |
| 8,167,951 B2 | 5/2012 | Ammann et al. |
| 8,170,641 B2 | 5/2012 | Belcher |
| 8,172,850 B2 | 5/2012 | Mcminn |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |
| 8,337,426 B2 | 12/2012 | Nycz |
| 8,337,501 B2 | 12/2012 | Fitz et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,529,578 B2 | 9/2013 | Daniels et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,551,099 B2 | 10/2013 | Lang et al. |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,781,557 B2 | 7/2014 | Dean et al. |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite |
| 8,979,936 B2 | 3/2015 | White et al. |
| 8,986,309 B1 | 3/2015 | Murphy |
| 9,005,297 B2 | 4/2015 | Katrana et al. |
| 9,060,788 B2 | 6/2015 | Bollinger |
| 9,066,734 B2 | 6/2015 | Schoenefeld et al. |
| 9,107,139 B2 | 8/2015 | Sirotkin et al. |
| 9,113,971 B2 | 8/2015 | Metzger et al. |
| 9,173,661 B2 | 11/2015 | Metzger et al. |
| 9,186,254 B2 | 11/2015 | Fitz et al. |

(56) References Cited

U.S. PATENT DOCUMENTS

| | | |
|---|---|---|
| 9,208,558 B2 | 12/2015 | Dean et al. |
| 9,241,745 B2 | 1/2016 | Smith et al. |
| 9,271,744 B2 | 3/2016 | Meridew |
| 9,275,191 B2 | 3/2016 | Dean et al. |
| 9,289,253 B2 | 3/2016 | Vanasse et al. |
| 9,292,920 B2 | 3/2016 | Dean et al. |
| 9,330,206 B2 | 5/2016 | Dean et al. |
| 9,339,278 B2 | 5/2016 | Meridew et al. |
| 9,345,548 B2 | 5/2016 | Schoenefeld et al. |
| 9,445,907 B2 | 9/2016 | Meridew et al. |
| 9,468,538 B2 | 10/2016 | Nycz et al. |
| 9,480,490 B2 | 11/2016 | Metzger et al. |
| 9,480,580 B2 | 11/2016 | White et al. |
| 9,522,010 B2 | 12/2016 | Metzger et al. |
| 9,539,013 B2 | 1/2017 | Katrana et al. |
| 9,662,127 B2 | 5/2017 | Meridew et al. |
| 9,662,216 B2 | 5/2017 | Witt et al. |
| 9,700,329 B2 | 7/2017 | Metzger et al. |
| 9,730,616 B2 | 8/2017 | Hershberger |
| 9,743,935 B2 | 8/2017 | Smith et al. |
| 9,795,399 B2 | 10/2017 | Metzger et al. |
| 9,861,387 B2 | 1/2018 | Metzger et al. |
| 9,907,659 B2 | 3/2018 | Belcher et al. |
| 9,913,734 B2 | 3/2018 | White et al. |
| 9,918,740 B2 | 3/2018 | Uthgenannt et al. |
| 9,968,376 B2 | 5/2018 | Metzger et al. |
| 9,993,344 B2 | 6/2018 | White et al. |
| 10,159,498 B2 | 12/2018 | Uthgenannt et al. |
| 10,206,695 B2 | 2/2019 | Meridew et al. |
| 10,206,697 B2 | 2/2019 | Metzger et al. |
| 10,278,711 B2 | 5/2019 | Meridew et al. |
| 2001/0005797 A1 | 6/2001 | Barlow et al. |
| 2001/0011190 A1 | 8/2001 | Park |
| 2001/0018589 A1 | 8/2001 | Muller |
| 2001/0021876 A1 | 9/2001 | Terrill-Grisoni et al. |
| 2001/0034554 A1 | 10/2001 | Pappas |
| 2001/0037155 A1 | 11/2001 | Merchant |
| 2001/0054478 A1 | 12/2001 | Watanabe et al. |
| 2002/0007294 A1 | 1/2002 | Bradbury et al. |
| 2002/0029038 A1 | 3/2002 | Haines |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0062127 A1 | 5/2002 | Schumacher et al. |
| 2002/0077540 A1 | 6/2002 | Kienzle, III |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0107523 A1 | 8/2002 | Naughton et al. |
| 2002/0116023 A1 | 8/2002 | Fletcher et al. |
| 2002/0120342 A1 | 8/2002 | Gibbs |
| 2002/0128872 A1 | 9/2002 | Giammattei |
| 2002/0147415 A1 | 10/2002 | Martelli |
| 2002/0173797 A1 | 11/2002 | Van Zile et al. |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198529 A1 | 12/2002 | Masini |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson, Jr. et al. |
| 2003/0028196 A1 | 2/2003 | Bonutti |
| 2003/0039676 A1 | 2/2003 | Boyce et al. |
| 2003/0055502 A1 | 3/2003 | Lang et al. |
| 2003/0060831 A1 | 3/2003 | Bonutti |
| 2003/0069897 A1 | 4/2003 | Roy et al. |
| 2003/0074800 A1 | 4/2003 | Huang |
| 2003/0100906 A1 | 5/2003 | Rosa et al. |
| 2003/0100907 A1 | 5/2003 | Rosa et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130665 A1 | 7/2003 | Pinczewski et al. |
| 2003/0130741 A1 | 7/2003 | McMinn |
| 2003/0139817 A1 | 7/2003 | Tuke et al. |
| 2003/0153829 A1 | 8/2003 | Sarin et al. |
| 2003/0158606 A1 | 8/2003 | Coon et al. |
| 2003/0171757 A1 | 9/2003 | Coon et al. |
| 2003/0181987 A1 | 9/2003 | Muirhead-allwood |
| 2003/0212403 A1 | 11/2003 | Swanson |
| 2003/0212459 A1 | 11/2003 | Gibbs |
| 2003/0216669 A1 | 11/2003 | Lang et al. |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0018144 A1 | 1/2004 | Briscoe |
| 2004/0030245 A1 | 2/2004 | Noble et al. |
| 2004/0034302 A1 | 2/2004 | Abovitz et al. |
| 2004/0039395 A1 | 2/2004 | Coon et al. |
| 2004/0044295 A1 | 3/2004 | Reinert et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0097952 A1 | 5/2004 | Sarin et al. |
| 2004/0098133 A1 | 5/2004 | Carignan et al. |
| 2004/0102785 A1 | 5/2004 | Hodorek et al. |
| 2004/0102792 A1 | 5/2004 | Sarin et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0117026 A1 | 6/2004 | Tuma et al. |
| 2004/0118229 A1 | 6/2004 | Reynolds et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138670 A1 | 7/2004 | Metzger |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Trueman, III |
| 2004/0220583 A1 | 11/2004 | Pieczynski, II et al. |
| 2004/0225369 A1 | 11/2004 | Lakin et al. |
| 2004/0230199 A1 | 11/2004 | Jansen et al. |
| 2004/0236341 A1 | 11/2004 | Petersen |
| 2004/0236424 A1 | 11/2004 | Berez et al. |
| 2004/0243148 A1 | 12/2004 | Wasielewski |
| 2004/0243481 A1 | 12/2004 | Bradbury et al. |
| 2004/0249386 A1 | 12/2004 | Faoro |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0009952 A1 | 1/2005 | Qian et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0015599 A1 | 1/2005 | Wang et al. |
| 2005/0015603 A1 | 1/2005 | Cabezas et al. |
| 2005/0015604 A1 | 1/2005 | Sundararajan et al. |
| 2005/0015605 A1 | 1/2005 | Lin et al. |
| 2005/0019664 A1 | 1/2005 | Matsumoto |
| 2005/0021044 A1 | 1/2005 | Stone et al. |
| 2005/0021148 A1 | 1/2005 | Gibbs |
| 2005/0021299 A1 | 1/2005 | Kadota et al. |
| 2005/0021494 A1 | 1/2005 | Wilkinson |
| 2005/0027303 A1 | 2/2005 | Lionberger et al. |
| 2005/0027361 A1 | 2/2005 | Reiley |

(56) References Cited

U.S. PATENT DOCUMENTS

| | | |
|---|---|---|
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065617 A1 | 3/2005 | Moctezuma de la Barrera et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0109855 A1 | 5/2005 | Mccombs |
| 2005/0113659 A1 | 5/2005 | Pothier et al. |
| 2005/0113840 A1 | 5/2005 | Metzger et al. |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0143828 A1 | 6/2005 | Collins et al. |
| 2005/0148843 A1 | 7/2005 | Roose |
| 2005/0149042 A1 | 7/2005 | Metzger |
| 2005/0171545 A1 | 8/2005 | Walsh et al. |
| 2005/0177170 A1 | 8/2005 | Fisher et al. |
| 2005/0177245 A1 | 8/2005 | Leatherbury et al. |
| 2005/0203384 A1 | 9/2005 | Sati et al. |
| 2005/0203536 A1 | 9/2005 | Laffargue et al. |
| 2005/0203540 A1 | 9/2005 | Broyles |
| 2005/0209597 A1 | 9/2005 | Long et al. |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams, III et al. |
| 2005/0234332 A1 | 10/2005 | Murphy |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245808 A1 | 11/2005 | Carson |
| 2005/0245934 A1 | 11/2005 | Tuke et al. |
| 2005/0245936 A1 | 11/2005 | Tuke et al. |
| 2005/0251026 A1 | 11/2005 | Stone |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0025778 A1 | 2/2006 | Ferree |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058809 A1 | 3/2006 | Zink et al. |
| 2006/0058884 A1 | 3/2006 | Aram et al. |
| 2006/0058886 A1* | 3/2006 | Wozencroft ....... A61B 17/1746 623/22.15 |
| 2006/0069444 A1 | 3/2006 | Deffenbaugh |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0094958 A1 | 5/2006 | Marquart et al. |
| 2006/0095044 A1 | 5/2006 | Grady, Jr. et al. |
| 2006/0095047 A1 | 5/2006 | de la Barrera |
| 2006/0095049 A1 | 5/2006 | Zannis et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122491 A1 | 6/2006 | Murray et al. |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0142774 A1 | 6/2006 | Metzger |
| 2006/0142778 A1 | 6/2006 | Dees |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0241775 A1 | 10/2006 | Buss |
| 2006/0241776 A1 | 10/2006 | Brown et al. |
| 2006/0241781 A1 | 10/2006 | Brown et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083209 A1 | 4/2007 | Schenberger et al. |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0106391 A1 | 5/2007 | Ronk |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0149981 A1 | 6/2007 | Bhattacharyya |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0179739 A1 | 8/2007 | Donofrio et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |

(56) References Cited

U.S. PATENT DOCUMENTS

| | | |
|---|---|---|
| 2007/0224238 A1 | 9/2007 | Mansmann et al. |
| 2007/0225719 A1 | 9/2007 | Stone et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244457 A1 | 10/2007 | Fangrow |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |
| 2007/0255030 A1 | 11/2007 | Sakamoto et al. |
| 2007/0255255 A1 | 11/2007 | Shah et al. |
| 2007/0255288 A1 | 11/2007 | Mahfouz et al. |
| 2007/0255412 A1 | 11/2007 | Hajaj et al. |
| 2007/0262567 A1 | 11/2007 | Benson |
| 2007/0262867 A1 | 11/2007 | Westrick et al. |
| 2007/0270680 A1 | 11/2007 | Sheffer et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0282451 A1 | 12/2007 | Metzger et al. |
| 2007/0288029 A1 | 12/2007 | Justin et al. |
| 2007/0288030 A1 | 12/2007 | Metzger et al. |
| 2008/0009874 A1 | 1/2008 | Meridew et al. |
| 2008/0009952 A1 | 1/2008 | Hodge |
| 2008/0015599 A1 | 1/2008 | D'alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0015607 A1 | 1/2008 | D'Alessio et al. |
| 2008/0021299 A1 | 1/2008 | Meulink |
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133016 A1 | 6/2008 | Heinz |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0221699 A1 | 9/2008 | Meridew et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0249395 A1 | 10/2008 | Shachar et al. |
| 2008/0255674 A1 | 10/2008 | Rahaman et al. |
| 2008/0257363 A1 | 10/2008 | Schoenefeld et al. |
| 2008/0262499 A1 | 10/2008 | Giori et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El |
| 2008/0287954 A1 | 11/2008 | Kunz et al. |
| 2008/0287959 A1 | 11/2008 | Quest et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0312746 A1 | 12/2008 | Unger |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0022015 A1 | 1/2009 | Harrison |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0066936 A1 | 3/2009 | Huang et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0099570 A1 | 4/2009 | Paradis et al. |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0129067 A1 | 5/2009 | Fan et al. |
| 2009/0131941 A1 | 5/2009 | Park et al. |
| 2009/0131942 A1 | 5/2009 | Aker et al. |
| 2009/0138019 A1 | 5/2009 | Wasielewski |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |

(56) References Cited

U.S. PATENT DOCUMENTS

| | | |
|---|---|---|
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0204225 A1 | 8/2009 | Meridew et al. |
| 2009/0209884 A1 | 8/2009 | Van Vorhis et al. |
| 2009/0209961 A1 | 8/2009 | Ferrante et al. |
| 2009/0210067 A1 | 8/2009 | Meridew |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234217 A1 | 9/2009 | Mire et al. |
| 2009/0234302 A1 | 9/2009 | Hoendervoogt et al. |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2009/0318930 A1 | 12/2009 | Stone et al. |
| 2009/0318931 A1 | 12/2009 | Stone et al. |
| 2010/0010493 A1 | 1/2010 | Dower |
| 2010/0015082 A1 | 1/2010 | Ting-jenulis et al. |
| 2010/0016705 A1 | 1/2010 | Stone et al. |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0049327 A1 | 2/2010 | Isch et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger |
| 2010/0094295 A1 | 4/2010 | Schnieders et al. |
| 2010/0099977 A1 | 4/2010 | Hershberger |
| 2010/0100011 A1 | 4/2010 | Roche |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0131073 A1 | 5/2010 | Meridew et al. |
| 2010/0136214 A1 | 6/2010 | Kumar |
| 2010/0137869 A1 | 6/2010 | Borja et al. |
| 2010/0137871 A1 | 6/2010 | Borja |
| 2010/0137924 A1 | 6/2010 | Tuke et al. |
| 2010/0139377 A1 | 6/2010 | Huang et al. |
| 2010/0145343 A1 | 6/2010 | Johnson et al. |
| 2010/0145344 A1 | 6/2010 | Jordan et al. |
| 2010/0145466 A1 | 6/2010 | Slone |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0286789 A1 | 11/2010 | Meridew |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0015752 A1 | 1/2011 | Meridew |
| 2011/0015753 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski |
| 2011/0029116 A1 | 2/2011 | Jordan et al. |
| 2011/0035012 A1 | 2/2011 | Linares |
| 2011/0040303 A1 | 2/2011 | Iannotti et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0060339 A1 | 3/2011 | de Wekker |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184424 A1 | 7/2011 | Isch et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |

(56) References Cited

U.S. PATENT DOCUMENTS

| | | |
|---|---|---|
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276053 A1 | 11/2011 | Birkbeck et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0053590 A1 | 3/2012 | Allen et al. |
| 2012/0063655 A1 | 3/2012 | Dean et al. |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch et al. |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0190971 A1 | 7/2012 | de Wekker |
| 2012/0192401 A1 | 8/2012 | Pavlovskaia et al. |
| 2012/0196314 A1 | 8/2012 | Nawaz et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0245647 A1* | 9/2012 | Kunz ............... A61B 17/1746 606/86 R |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2012/0330319 A1 | 12/2012 | Birkbeck et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0066323 A1 | 3/2013 | Nycz et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0110116 A1 | 5/2013 | Kehres et al. |
| 2013/0110470 A1 | 5/2013 | Vanasse et al. |
| 2013/0116699 A1 | 5/2013 | Smith et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0158671 A1 | 6/2013 | Uthgenannt et al. |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong |
| 2013/0289730 A1 | 10/2013 | Gabriel et al. |
| 2013/0292870 A1 | 11/2013 | Roger |
| 2013/0317511 A1 | 11/2013 | Bojarski et al. |
| 2013/0317621 A1 | 11/2013 | Metzger et al. |
| 2013/0326878 A1 | 12/2013 | Boehm et al. |
| 2013/0338673 A1 | 12/2013 | Keppler |
| 2014/0001226 A1 | 1/2014 | Scabin et al. |
| 2014/0005672 A1 | 1/2014 | Edwards et al. |
| 2014/0012266 A1 | 1/2014 | Bonin, Jr. et al. |
| 2014/0018934 A1 | 1/2014 | Meridew et al. |
| 2014/0052270 A1 | 2/2014 | Witt et al. |
| 2014/0066937 A1 | 3/2014 | Wiebe, III et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0081275 A1 | 5/2014 | Metzger et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |
| 2015/0150688 A1 | 6/2015 | Vanasse et al. |
| 2015/0157341 A1 | 6/2015 | Catanzarite et al. |
| 2015/0320429 A1 | 11/2015 | Katrana et al. |
| 2015/0320508 A1 | 11/2015 | White et al. |
| 2015/0335438 A1 | 11/2015 | Pierce et al. |
| 2015/0351778 A1 | 12/2015 | Uthgenannt et al. |
| 2016/0008013 A1 | 1/2016 | Metzger et al. |
| 2016/0038160 A1 | 2/2016 | Metzger |
| 2016/0100845 A1 | 4/2016 | Smith et al. |

(56) References Cited

U.S. PATENT DOCUMENTS

| | | | |
|---|---|---|---|
| 2016/0135824 A1 | 5/2016 | Vanasse et al. |
| 2016/0196651 A1 | 7/2016 | Dean et al. |
| 2016/0203241 A1 | 7/2016 | Dean et al. |
| 2016/0213491 A1 | 7/2016 | Schoenefeld et al. |
| 2016/0338838 A1 | 11/2016 | Meridew et al. |
| 2017/0000626 A1 | 1/2017 | White et al. |
| 2017/0056030 A1 | 3/2017 | Metzger et al. |
| 2017/0224496 A1 | 8/2017 | Witt et al. |
| 2017/0273718 A1 | 9/2017 | Metzger et al. |
| 2017/0311846 A1 | 11/2017 | Hershberger |
| 2017/0333194 A1 | 11/2017 | Pierce et al. |
| 2018/0008292 A1 | 1/2018 | Metzger et al. |
| 2018/0140426 A1 | 5/2018 | Belcher et al. |
| 2018/0153565 A1 | 6/2018 | Stone et al. |
| 2018/0168690 A1 | 6/2018 | Uthgenannt et al. |
| 2018/0168822 A1 | 6/2018 | White et al. |
| 2018/0206888 A1 | 7/2018 | Metzger et al. |
| 2018/0250135 A1 | 9/2018 | White et al. |
| 2018/0256257 A1 | 9/2018 | Luby |
| 2019/0069909 A1 | 3/2019 | Uthgenannt et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CH | 1179960 A | 5/1927 |
| CN | 1630495 A | 6/2005 |
| CN | 1728976 A | 2/2006 |
| CN | 1729483 A | 2/2006 |
| CN | 1729484 A | 2/2006 |
| CN | 193844 A | 2/2007 |
| CN | 101111197 A | 1/2008 |
| CN | 102038553 A | 5/2011 |
| CN | 102335742 A | 2/2012 |
| DE | 337437 C | 5/1921 |
| DE | 3447365 A1 | 7/1986 |
| DE | 04219939 A1 | 12/1993 |
| DE | 4421153 A1 | 12/1995 |
| DE | 10341187 A1 | 3/2005 |
| DE | 10358926 B4 | 9/2006 |
| DE | 102009028503 A1 | 2/2011 |
| DE | 102010013258 A1 | 6/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1563810 A1 | 8/2005 |
| EP | 1574177 A1 | 9/2005 |
| EP | 1588669 A1 | 10/2005 |
| EP | 1634551 A2 | 3/2006 |
| EP | 1832239 A1 | 9/2007 |
| EP | 1852072 A2 | 11/2007 |
| EP | 1852072 A3 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| EP | 2816962 A1 | 12/2014 |
| EP | 2029061 B1 | 2/2017 |
| EP | 2303192 B1 | 11/2018 |
| FR | 1111677 A | 3/1956 |
| FR | 2429582 A1 | 1/1980 |
| FR | 2659226 A2 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A1 | 6/1988 |
| GB | 2423021 | 8/2006 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| GB | 2486390 B | 11/2015 |
| GB | 2527690 B | 6/2016 |
| GB | 2483980 B | 12/2016 |
| GB | 2491526 B | 1/2017 |
| JP | 59157715 A | 9/1984 |
| JP | 60231208 A | 11/1985 |
| JP | 6233790 A | 8/1994 |
| JP | 2000245758 A | 9/2000 |
| JP | 2004008797 A | 1/2004 |
| JP | 2005218861 A | 8/2005 |
| JP | 2009515610 A | 4/2006 |
| JP | 2009514612 A | 4/2009 |
| JP | 2011505080 A | 2/2011 |
| JP | 2011517996 A | 6/2011 |
| JP | 2011527885 A | 11/2011 |
| JP | 5710014 B2 | 4/2015 |
| KR | 200050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 A | 5/2005 |
| TW | 201114409 A | 5/2011 |
| WO | WO-8807840 A1 | 10/1988 |
| WO | WO-8909028 A1 | 10/1989 |
| WO | WO-9014806 A1 | 12/1990 |
| WO | WO-9107139 A1 | 5/1991 |
| WO | WO-9325157 A1 | 12/1993 |
| WO | WO-9413218 A1 | 6/1994 |
| WO | WO-9528688 A1 | 10/1995 |
| WO | WO-9607361 A1 | 3/1996 |
| WO | WO-9729703 A1 | 8/1997 |
| WO | WO-9901073 A1 | 1/1999 |
| WO | WO-9952473 A1 | 10/1999 |
| WO | WO-9959106 A1 | 11/1999 |
| WO | WO-2008091358 A1 | 7/2000 |
| WO | WO-0110339 A2 | 2/2001 |
| WO | WO-0133511 A2 | 5/2001 |
| WO | WO-0170142 A1 | 9/2001 |
| WO | WO-0184479 A1 | 11/2001 |
| WO | WO-0217821 A2 | 3/2002 |
| WO | WO-2002026145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004030556 A2 | 4/2004 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2004112610 A2 | 12/2004 |

(56) References Cited

FOREIGN PATENT DOCUMENTS

| | | |
|---|---|---|
| WO | WO-2005051209 A1 | 6/2005 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2005099636 A1 | 10/2005 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2007145937 A3 | 12/2007 |
| WO | WO-2007147235 A1 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009006741 A1 | 1/2009 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010045537 A1 | 4/2010 |
| WO | WO-2010048257 A1 | 4/2010 |
| WO | WO-2010088696 A1 | 8/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO 2011041398 A1 | 4/2011 |
| WO | WO-2011060536 A1 | 5/2011 |
| WO | WO-2011063231 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013126416 A1 | 8/2013 |
| WO | WO-2013170872 A1 | 11/2013 |
| WO | WO-2014019712 A1 | 2/2014 |
| WO | WO-2015084831 A1 | 6/2015 |
| WO | WO-2016007631 A1 | 1/2016 |

OTHER PUBLICATIONS

"U.S. Appl. No. 13/041,883, Examiner's Answer dated Mar. 8, 2017", 8 pgs.

"U.S. Appl. No. 13/527,981, Final Office Action dated Feb. 8, 2017", 17 pgs.

"U.S. Appl. No. 14/064,970, Notice of Allowability dated Feb. 10, 2017", 2 pgs.

"U.S. Appl. No. 14/064,970, Notice of Allowability dated Feb. 17, 2017", 2 pgs.

"U.S. Appl. No. 14/064,970, Notice of Allowance dated Jan. 27, 2017", 10 pgs.

"U.S. Appl. No. 14/105,669, Notice of Allowance dated Jan. 26, 2017", 7 pgs.

"U.S. Appl. No. 14/658,429, Non Final Office Action dated Feb. 23, 2017", 6 pgs.

"U.S. Appl. No. 14/812,583, Restriction Requirement dated Jan. 23, 2017", 8 pgs.

"U.S. Appl. No. 14/973,057, Final Office Action dated Feb. 13, 2017", 7 pgs.

"U.S. Appl. No. 14/973,057, Response filed Jan. 18, 2017 to Non Final Office Action dated Oct. 18, 2016", 8 pgs.

"U.S. Appl. No. 15/267,714, Response filed Feb. 28, 2017 to Restriction Requirement dated Jan. 5, 2017", 8 pgs.

"U.S. Appl. No. 15/352,721, Preliminary Amendment filed Feb. 3, 2017", 6 pgs.

"European Application Serial No. 09732174.9, Response filed Feb. 22, 2017 to Communication Pursuant to Article 94(3) EPC dated Oct. 17, 2016", 6 pgs.

"European Application Serial No. 12724475.4, Response filed Jan. 10, 2017 to Communication Pursuant to Article 94(3) EPC dated Aug. 31, 2016", 17 pgs.

"International Application Serial No. PCT/US2015/039561, International Preliminary Report on Patentability dated Jan. 19, 2017", 8 pgs.

"U.S. Appl. No. 12/255,945, Notice of Allowance dated May 5, 2017", 7 pgs.

"U.S. Appl. No. 12/371,096, Appeal Decision mailed Jun. 23, 2017", 10 pgs.

"U.S. Appl. No. 13/041,883, Reply Brief Filed May 21, 2017 to Examiner's Answer dated Mar. 8, 2017", 8 pgs.

"U.S. Appl. No. 13/527,981, Examiner Interview Summary dated Apr. 24, 2017", 5 pgs.

"U.S. Appl. No. 13/527,981, Non Final Office Action dated Jun. 22, 2017", 6 pgs.

"U.S. Appl. No. 13/527,981, Response filed May 8, 2017 to Final Office Action dated Feb. 8, 2017", 18 pgs.

"U.S. Appl. No. 13/800,334, Final Office Action dated Jun. 15, 2017", 22 pgs.

"U.S. Appl. No. 13/800,334, Response filed Mar. 15, 2017 to Non Final Office Action dated Dec. 12, 2016", 16 pgs.

"U.S. Appl. No. 14/327,234, Notice of Allowance dated Jun. 22, 2017", 12 pgs.

"U.S. Appl. No. 14/327,234, Response filed May 17, 2017 to Restriction Requriement dated Apr. 6, 2017", 8 pgs.

"U.S. Appl. No. 14/327,234, Restriction Requirement dated Apr. 6, 2017", 7 pgs.

"U.S. Appl. No. 14/483,214, Examiner Interview Summary dated Apr. 12, 2017", 3 pgs.

"U.S. Appl. No. 14/483,214, Non Final Office Action dated May 2, 2017", 10 pgs.

"U.S. Appl. No. 14/483,214, Response filed Jul. 31, 2017 to Non Final Office Action dated May 2, 2017", 12 pgs.

"U.S. Appl. No. 14/658,429, Examiner Interview Summary dated Aug. 17, 2017", 2 pgs.

"U.S. Appl. No. 14/658,429, Final Office Action dated Jun. 15, 2017", 7 pgs.

"U.S. Appl. No. 14/658,429, Response Filed May 19, 2017 to Non-Final Office Action dated Feb. 23, 2017", 15 pgs.

"U.S. Appl. No. 14/658,429, Response filed Aug. 11, 2017 to Final Office Action dated Jun. 15, 2017", 21 pgs.

"U.S. Appl. No. 14/798,809, Non Final Office Action dated Jun. 28, 2017", 7 pgs.

(56) References Cited

OTHER PUBLICATIONS

"U.S. Appl. No. 14/798,809, Response filed Apr. 3, 2017 to Restriction Requirement dated Jan. 4, 2017", 8 pgs.
"U.S. Appl. No. 14/812,583, Non Final Office Action dated May 9, 2017", 14 pgs.
"U.S. Appl. No. 14/812,583, Response filed Mar. 16, 2017 to Restriction Requirement dated Jan. 23, 2017", 6 pgs.
"U.S. Appl. No. 14/865,762, Non Final Office Action dated Jun. 13, 2017", 13 pgs.
"U.S. Appl. No. 14/865,762, Response filed May 17, 2017 to Restrictiion Requirement dated Apr. 13, 2017", 8 pgs.
"U.S. Appl. No. 14/865,762, Restriction Requirement dated Apr. 13, 2017", 6 pgs.
"U.S. Appl. No. 14/973,057, Corrected Notice of Allowance dated May 30, 2017", 2 pgs.
"U.S. Appl. No. 14/973,057, Notice of Allowance dated Apr. 27, 2017", 7 pgs.
"U.S. Appl. No. 14/973,057, Response filed Apr. 5, 2017 to Final Office Action dated Feb. 13, 2017", 9 pgs.
"U.S. Appl. No. 15/267,714, Non Final Office Action dated May 10, 2017", 23 pgs.
"U.S. Appl. No. 15/267,714, Response filed Aug. 4, 2017 to Non Final Office Action dated May 10, 2017", 21 pgs.
"U.S. Appl. No. 15/352,721, Corrected Notice of Allowance dated Apr. 27, 2017", 2 pgs.
"U.S. Appl. No. 15/352,721, Notice of Allowance dated Mar. 10, 2017", 11 pgs.
"U.S. Appl. No. 15/495,432, Preliminary Amendment filed May 17, 2017", 8 pgs.
"U.S. Appl. No. 15/618,331, Preliminary Amendment filed Jun. 28, 2017", 6 pgs.
"U.S. Appl. No. 15/650,035, Preliminary Amendment filed Jul. 20, 2017", 6 pgs.
"U.S. Appl. No. 15/672,724, Preliminary Amendment filed Aug. 9, 2017", 4 pgs.
"U.S. Appl. No. 15/672,724, Supplemental Preliminary Amendment filed Aug. 23, 2017", 7 pgs.
"U.S. Appl. No. 13/800,334, Response filed Aug. 10, 2017 to Final Office Action dated Jun. 15, 2017", 9 pgs.
"European Application Serial No. 09731923.0, Response filed Apr. 10, 2017 to Communication Pursuant to Article 94(3) EPC dated Nov. 29, 2016", 18 pgs.
"European Application Serial No. 16179349.2, Extended European Search Report dated Mar. 22, 2017", 9 pgs.
"European Application Serial No. 16179569.5, Extended European Search Report dated Jul. 7, 2017", 8 pgs.
"U.S. Appl. No. 12/371,096, Corrected Notice of Allowance dated Nov. 13, 2017", 2 pgs.
"U.S. Appl. No. 13/527,981, Corrected Notice of Allowance dated Nov. 27, 2017", 2 pgs.
"U.S. Appl. No. 14/658,429, Examiner Interview Summary dated Dec. 26, 2017", 2 pgs.
"U.S. Appl. No. 14/658,429, Notice of Allowance dated Feb. 9, 2018", 8 pgs.
"U.S. Appl. No. 14/658,429, Response filed Jan. 4, 2018 to Final Office Action dated Oct. 20, 2017", 20 pgs.
"U.S. Appl. No. 14/739,160, Non Final Office Action dated Jan. 16, 2018", 14 pgs.
"U.S. Appl. No. 14/798,809, Advisory Action dated Feb. 28, 2018", 3 pgs.
"U.S. Appl. No. 14/798,809, Final Office Action dated Dec. 29, 2017", 4 pgs.
"U.S. Appl. No. 14/798,809, Response filed Feb. 21, 2018 to Final Office Action dated Dec. 29, 2017", 7 pgs.
"U.S. Appl. No. 14/865,762, Final Office Action dated Mar. 8, 2018", 14 pgs.
"U.S. Appl. No. 15/008,528, Response filed Dec. 7, 2017 to Restriction Requirement dated Oct. 12, 2017", 7 pgs.
"U.S. Appl. No. 15/224,741, Restriction Requirement dated Mar. 15, 2018", 7 pgs.

"U.S. Appl. No. 15/495,432, Restriction Requirement dated Feb. 9, 2018", 8 pgs.
"U.S. Appl. No. 15/618,331, Notice of Allowance dated Jan. 10, 2018", 10 pgs.
"U.S. Appl. No. 15/863,421, Preliminary Amendment Filed Mar. 13, 2018", 9 pgs.
"U.S. Appl. No. 15/875,204, Preliminary Amendment Filed Mar. 8, 2018", 9 pgs.
"U.S. Appl. No. 15/878,984, Preliminary Amendment Filed Mar. 9, 2018", 8 pgs.
"European Application Serial No. 16179569.5, Response filed Feb. 7, 2018 to Extended European Search Report dated Jul. 7, 2017", 14 pgs.
"German Application Serial No. 1120111008104, Response filed Feb. 23, 2018 to Office Action dated Oct. 18, 2017", (W/ English translation of claims), 8 pgs.
U.S. Appl. No. 15/672,724, filed Aug. 9, 2017, Patient-Specific Augments.
U.S. Appl. No. 15/650,035, filed Jul. 14, 2017, Mechanical Axis Alignment Using MRI Imaging.
U.S. Appl. No. 15/495,432, filed Apr. 24, 2017, Patient-Specific Hip Joint Devices.
U.S. Appl. No. 15/618,331, filed Jun. 9, 2017, Patient-Specific Orthopedic Instruments.
"U.S. Appl. No. 12/371,096, Notice of Allowance dated Oct. 20, 2017", 5 pgs.
"U.S. Appl. No. 13/527,981, Notice of Allowance dated Nov. 3, 2017", 5 pgs.
"U.S. Appl. No. 13/527,981, Response filed Sep. 21, 2017 to Non Final Office Action dated Jun. 22, 2017", 11 pgs.
"U.S. Appl. No. 13/800,334, Notice of Allowance dated Aug. 31, 2017", 8 pgs.
"U.S. Appl. No. 14/483,214, Final Office Action dated Oct. 25, 2017", 11 pgs.
"U.S. Appl. No. 14/658,429, Advisory Action dated Sep. 12, 2017", 3 pgs.
"U.S. Appl. No. 14/658,429, Final Office Action dated Oct. 20, 2017", 11 pgs.
"U.S. Appl. No. 14/658,429, Supplemental Response Filed Sep. 21, 2017 to Final Office Action dated Jun. 15, 2017 and Advisory Action dated Sep. 12, 2017", 25 pgs.
"U.S. Appl. No. 14/798,809, Examiner Interview Summary dated Sep. 14, 2017", 3 pgs.
"U.S. Appl. No. 14/798,809, Response filed Sep. 26, 2017 to Non Final Office Action dated Jun. 28, 2017", 9 pgs.
"U.S. Appl. No. 14/865,762, Response filed Sep. 13, 2017 to Non Final Office Action dated Jun. 13, 2017", 17 pgs.
"U.S. Appl. No. 15/008,528, Restriction Requirement dated Oct. 12, 2017", 6 pgs.
"U.S. Appl. No. 15/267,714, Notice of Allowance dated Oct. 10, 2017", 13 pgs.
"U.S. Appl. No. 15/712,679, Preliminary Amendment filed Oct. 12, 2017", 7 pgs.
"European Application Serial No. 15739458.6, Response filed Sep. 4, 2017 to Communication pursuant to Rules 161(1) and 162 EPC dated Feb. 21, 2017", 9 pgs.
"European Application Serial No. 16179349.2, Response filed Oct. 19, 2017 to Extended European Search Report dated Mar. 22, 2017", 17 pgs.
"German Application Serial No. 1120111008104, Office Action dated Oct. 18, 2017", w/English Claims, 7 pgs.
U.S. Appl. No. 15/911,701, filed Mar. 5, 2018, Virtual Surgery Planning System and Method.
U.S. Appl. No. 15/878,984, filed Jan. 24, 2018, Alignment Guides With Patient-Specific Anchoring Elements.
U.S. Appl. No. 15/875,204, filed Jan 19, 2018, Method and Apparatus for Manufacturing an Implant.
U.S. Appl. No. 15/863,421, filed Jan. 5, 2018, Patient-Specific Acetabular Alignment Guides.
U.S. Appl. No. 15/887,740, filed Feb. 2, 2018, Backup Surgical Instrument System and Method.
U.S. Appl. No. 15/933,576, filed Mar. 23, 2018, Patient-Specific Orthopedic Instruments.

(56) References Cited

OTHER PUBLICATIONS

U.S. Appl. No. 15/712,679, filed Sep. 22, 2017, Patient-Specific Knee Alignment Guikde and Associated Method.
"U.S. Appl. No. 13/041,883, Appeal Decision mailed Sep. 13, 2018", 13 pgs.
"U.S. Appl. No. 14/739,160, Notice of Allowance dated Aug. 6, 2018", 9 pgs.
"U.S. Appl. No. 14/739,160, Response filed Apr. 16, 2018 to Non Final Office Action dated Jan. 16, 2018", 19 pgs.
"U.S. Appl. No. 14/798,809, Corrected Notice of Allowability dated Jun. 27, 2018", 4 pgs.
"U.S. Appl. No. 14/798,809, Notice of Allowance dated May 3, 2018", 7 pgs.
"U.S. Appl. No. 14/798,809, Notice of Allowance dated Sep. 24, 2018", 6 pgs.
"U.S. Appl. No. 14/798,809, Response Filed Mar. 29, 2018 to Advisory Action dated Feb. 28, 2018", 8 pgs.
"U.S. Appl. No. 14/865,762, Non Final Office Action dated Aug. 27, 2018", 15 pgs.
"U.S. Appl. No. 14/865,762, Response filed Jun. 8, 2018 to Non Final Office Action dated Mar. 8, 2018", 17 pgs.
"U.S. Appl. No. 15/008,528, Non Final Office Action dated Jun. 11, 2018", 13 pgs.
"U.S. Appl. No. 15/008,528, Response Filed Sep. 11, 2018 to Non-Final Office Action dated Jun. 11, 2018", 14 pgs.
"U.S. Appl. No. 15/224,741, Non Final Office Action dated Jun. 11, 2018", 10 pgs.
"U.S. Appl. No. 15/224,741, Response filed May 14, 2018 to Restriction Requirement dated Mar. 15, 2018", 8 pgs.
"U.S. Appl. No. 15/495,432, Non Final Office Action dated May 9, 2018", 9 pgs.
"U.S. Appl. No. 15/495,432, Response filed Apr. 4, 2018 to Restriction Requirement dated Feb. 9, 2018", 10 pgs.
"U.S. Appl. No. 15/712,679, Notice of Allowance dated Oct. 10, 2018", 9 pgs.
"U.S. Appl. No. 15/887,740, Preliminary Amendment Filed Apr. 27, 2018", 8 pgs.
"U.S. Appl. No. 15/933,576, Notice of Allowance dated Oct. 17, 2018", 8 pgs.
"U.S. Appl. No. 15/933,576, Preliminary Amendment Filed Apr. 17, 2018", 6 pgs.
"U.S. Appl. No. 15/972,591, Non Final Office Action date Oct. 9, 2018"; 5 pgs.
"U.S. Appl. No. 15/972,591, Preliminary Amendment Filed May 21, 2018", 6 pgs.
"European Application Serial No. 10705951.1, Communication Pursuant to Article 94(3) EPC dated May 23, 2018", 7 pgs.
"European Application Serial No. 10705951.1, Response filed Oct. 2, 2018 to Communication Pursuant to Article 94(3) EPC dated May 23, 2018", 12 pgs.
"European Application Serial No. 17188434.9, Extended European Search Report dated Aug. 30, 2018", 9 pgs.
Kwon, Oh-Ryong, et al,. "The Effect of Femoral Cutting Guide Design Improvements for Patient-Specific Instruments", BioMed Research International, vol. 2015, Article ID 978686; https://www.hindawi.com/journals/bmri/2015/978686/, (Apr. 20, 2015), 9 pgs.
MacDessi, S., et al., "Patient-specific cutting guides for total knee arthroplasty", Cochrane Database of Systematic Reviews, Issue 3, Art. No. CD012589; http://onlinelibrary.wiley.com/doi/10,1002/14651858.CD012589/full, (Mar. 13, 2017), 16 pgs.
U.S. Appl. No. 16/374,850, filed Apr. 1, 2019, Patient-Specific Femoral Guide.
U.S. Appl. No. 16/183,457, filed Nov. 7, 2018, Method and Appratus for Manufacturing an Implant.
U.S. Appl. No. 16/243,883, filed Jan. 9, 2019, Patient-Specific Knee Alignment Guide and Associated Method.
"U.S. Appl. No. 13/041,883, Amendment and Response Filed Oct. 25, 2018 to Appeal Decision Mailed Sep. 13, 2018", 7 pgs.
"U.S. Appl. No. 13/041,883, Corrected Notice of Allowability dated Feb. 21, 2019", 4 pgs.
"U.S. Appl. No. 13/041,883, Examiner Interview Summary dated Oct. 29, 2018", 3 pgs.
"U.S. Appl. No. 13/041,883, Notice of Allowance dated Dec. 26, 2018", 7 pgs.
"U.S. Appl. No. 14/798,809, Corrected Notice of Allowability dated Jan. 17, 2019", 2 pgs.
"U.S. Appl. No. 14/865,762, Final Office Action dated Mar. 1, 2019", 13 pgs.
"U.S. Appl. No. 14/865,762, Notice of Allowance dated May 22, 2019", 9 pgs.
"U.S. Appl. No. 14/865,762, Response filed Apr. 24, 2019 to Final Office Action dated Mar. 1, 2019", 13 pgs.
"U.S. Appl. No. 14/865,762, Response filed Nov. 26, 2018 to Non Final Office Action dated Aug. 27, 2018", 18 pgs.
"U.S. Appl. No. 15/008,528, Final Office Action dated Jan. 25, 2019", 9 pgs.
"U.S. Appl. No. 15/008,528, Notice of Allowance dated Apr. 10, 2019", 8 pgs.
"U.S. Appl. No. 15/008,528, Response filed Mar. 20, 2019 to Final Office Action dated Jan. 25, 2019", 11 pgs.
"U.S. Appl. No. 15/093,384, Non Final Office Action dated Feb. 12, 2019", 9 pgs.
"U.S. Appl. No. 15/093,384, Response Filed Jan. 23, 2019 to Restriction Requirement dated Nov. 30, 2018", 7 pgs.
"U.S. Appl. No. 15/093,384, Response filed May 13, 2019 to Non Final Office Action dated Feb. 12, 2019", 12 pgs.
"U.S. Appl. No. 15/093,384, Restriction Requirement dated Nov. 30, 2018", 9 pgs.
"U.S. Appl. No. 15/672,724, Restriction Requirement dated Apr. 8, 2019", 9 pgs.
"U.S. Appl. No. 15/712,679, Corrected Notice of Aliowability dated Nov. 15, 2018", 2 pgs.
"U.S. Appl. No. 16/183,457, Preliminary Amendment Filed Nov. 7, 2018", 3 pgs,.
"U.S. Appl. No. 16/183,457, Supplemental Preliminary Amendment Filed Dec. 5, 2018", 7 pgs.
"U.S. Appl. No. 16/243,883, Preliminary Amendment filed Jan. 14, 2019", 6 pgs.
"U.S. Appl. No. 16/371,850, Supplemental Preliminary Amendment filed Apr. 29, 2019", 6 pgs.
"European Application Serial No. 17188434.9, Response filed Apr. 3, 2019 to Extended European Search Report dated Aug. 30, 2018", 23 pgs.
"3D-Implantatplanung und StereolithographieImplantatbohrschablonen", Stomatologie 101.3, (2004), 55-59.
"Amazing Precision. Beautiful Results. The next evolution of MAKOplasty® is here", MAKO Surgical Corp., (Feb. 2009), 6 pgs.
"U.S. Appl. No. 09/861,859, 312 Amendment filed Sep. 27, 2011", 3 pgs.
"U.S. Appl. No. 09/861,859, Final Office Action dated Aug. 5, 2011", 10 pgs.
"U.S. Appl. No. 09/861,859, Non Final Office Action dated Mar. 3, 2011", 9 pgs.
"U.S. Appl. No. 09/861,859, Notice of Allowance dated Sep. 8, 2011", 5 pgs.
"U.S. Appl. No. 09/861,859, Notice of Non Compliant Amendment dated Nov. 18, 2010", 3 pgs.
"U.S. Appl. No. 09/861,859, PTO Response to Rule 312 Communication dated Oct. 7, 2011", 2 pgs.
"U.S. Appl. No. 09/861,859, Response filed May 12, 2011 to Non Final Office Action dated Mar. 3, 2011", 13 pgs.
"U.S. Appl. No. 09/861,859, Response filed Aug. 22, 2011 to Final Office Action dated Aug. 5, 2011", 9 pgs.
"U.S. Appl. No. 09/861,859, Response filed Oct. 28, 2010 to Restriction Requirement dated Sep. 29, 2010", 1 pg.
"U.S. Appl. No. 09/861,859, Response filed Nov. 29, 2010 to Notice of Non Compliant Amendment dated Nov. 18, 2010", 8 pgs.
"U.S. Appl. No. 09/861,859, Restriction Requirement dated Sep. 29, 2010", 7 pgs.
"U.S. Appl. No. 11/363,548, Advisory Action dated Aug. 5, 2009", 2 pgs.

(56) References Cited

OTHER PUBLICATIONS

"U.S. Appl. No. 11/363,548, Appeal Brief filed Jun. 19, 2009", 52 pgs.
"U.S. Appl. No. 11/363,548, Final Office Action dated Jan. 22, 2009", 12 pgs.
"U.S. Appl. No. 11/363,548, Non Final Office Action dated Jul. 9, 2008", 11 pgs.
"U.S. Appl. No. 11/363,548, Notice of Allowance dated Apr. 9, 2010", 5 pgs.
"U.S. Appl. No. 11/363,548, Response filed Jun. 19, 2009 to Final Office Action dated Jan. 22, 2009", 9 pgs.
"U.S. Appl. No. 11/363,548, Response filed Oct. 8, 2008 to Non Final Office Action dated Jul. 9, 2008", 18 pgs.
"U.S. Appl. No. 11/971,390, Non Final Office Action dated Mar. 3, 2011", 7 pgs.
"U.S. Appl. No. 11/971,390, Notice of Allowance dated Jul. 26, 2011", 8 pgs.
"U.S. Appl. No. 11/971,390, Preliminary Amendment filed Jan. 14, 2011", 8 pgs.
"U.S. Appl. No. 11/971,390, Response filed May 12, 2011 to Non Final Office Action dated Mar. 3, 2011", 12 pgs.
"U.S. Appl. No. 11/971,390, Response filed Dec. 23, 2010 to Restriction Requirement dated Nov. 23, 2010", 1 pgs.
"U.S. Appl. No. 11/971,390, Restriction Requirement dated Nov. 23, 2010", 6 pgs.
"U.S. Appl. No. 12/039,849, Final Office Action dated Apr. 8, 2012", 7 pgs.
"U.S. Appl. No. 12/039,849, Non Final Office Action dated Mar. 8, 2012", 11 pgs.
"U.S. Appl. No. 12/039,849, Notice of Allowance dated Jun. 6, 2012", 7 pgs.
"U.S. Appl. No. 12/039,849, Response filed Apr. 3, 2012 to Non Final Office Action dated Mar. 8, 2012", 19 pgs.
"U.S. Appl. No. 12/039,849, Response filed May 14, 2012 to Final Office Action dated Apr. 8, 2012", 7 pgs.
"U.S. Appl. No. 12/039,849, Response filed Aug. 30, 2011 to Restriction Requirement dated Aug. 16, 2011", 11 pgs.
"U.S. Appl. No. 12/039,849, Restriction Requirement dated Aug. 16, 2011", 6 pgs.
"U.S. Appl. No. 12/103,824, Examiner Interview Summary dated Jan. 12, 2012", 2 pgs.
"U.S. Appl. No. 12/103,824, Examiner Interview Summary dated Sep. 19, 2011", 3 pgs.
"U.S. Appl. No. 12/103,824, Final Office Action dated Apr. 26, 2012", 19 pgs.
"U.S. Appl. No. 12/103,824, Final Office Action dated Dec. 6, 2011", 20 pgs.
"U.S. Appl. No. 12/103,824, Non Final Office Action dated Aug. 17, 2011", 17 pgs.
"U.S. Appl. No. 12/103,824, Response filed Sep. 15, 2011 to Non Final Office Action dated Aug. 17, 2011", 16 pgs.
"U.S. Appl. No. 12/103,834 , Final Office Action dated Dec. 8, 2010", 11 pgs.
"U.S. Appl. No. 12/103,834 , Non Final Office Action dated Jun. 22, 2010", 9 pgs.
"U.S. Appl. No. 12/103,834 , Response filed Feb. 3, 2011 to Final Office Action dated Dec. 8, 2010", 5 pgs.
"U.S. Appl. No. 12/103,834 , Response filed Sep. 21, 2010 to Non Final Office Action dated Jun. 22, 2010", 11 pgs.
"U.S. Appl. No. 12/103,834, Notice of Allowance dated Feb. 23, 2011", 9 ogs.
"U.S. Appl. No. 12/103,834, Response filed Mar. 18, 2010 to Restriction Requirement dated Feb. 18, 2010", 9 pgs.
"U.S. Appl. No. 12/103,834, Restriction Requirement dated Feb. 18, 2010", 9 pgs.
"U.S. Appl. No. 12/211,407, Examiner Interview Summary dated Jan. 13, 2012", 3 pgs.
"U.S. Appl. No. 12/211,407, Examiner Interview Summary dated Dec. 5, 2013", 3 pgs.
"U.S. Appl. No. 12/211,407, Final Office Action dated Nov. 25, 2011", 14 pgs.
"U.S. Appl. No. 12/211,407, Non Final Office Action dated Aug. 17, 2011", 15 pgs.
"U.S. Appl. No. 12/211,407, Notice of Allowance dated Aug. 7, 2013", 12 pgs.
"U.S. Appl. No. 12/211,407, Response filed Jan. 16, 2012 to Final Office Action dated Nov. 25, 2011", 18 pgs.
"U.S. Appl. No. 12/211,407, Response filed Aug. 29, 2011 to Non Final Office Action dated Aug. 17, 2011", 19 pgs.
"U.S. Appl. No. 12/255,945, Advisory Action dated Feb. 5, 2014", 3 pgs.
"U.S. Appl. No. 12/255,945, Advisory Action dated Feb. 10, 2012", 3 pgs.
"U.S. Appl. No. 12/255,945, Advisory Action dated Mar. 27, 2014", 3 pgs.
"U.S. Appl. No. 12/255,945, Appeal Brief filed Mar. 26, 2014", 29 pgs.
"U.S. Appl. No. 12/255,945, Appeal Brief filed Oct. 13, 2014", 30 pgs.
"U.S. Appl. No. 12/255,945, Examiner Interview Summary dated Aug. 13, 2013", 3 pgs.
"U.S. Appl. No. 12/255,945, Examiner Interview Summary dated Sep. 22, 2011", 3 pgs.
"U.S. Appl. No. 12/255,945, Examiner's Answer dated Feb. 12, 2015", 26 pgs.
"U.S. Appl. No. 12/255,945, Final Office Action dated Sep. 30, 2013", 21 pgs.
"U.S. Appl. No. 12/255,945, Final Office Action dated Nov. 28, 2011", 14 pgs.
"U.S. Appl. No. 12/255,945, Non Final Office Action dated May 7, 2013", 23 pgs.
"U.S. Appl. No. 12/255,945, Non Final Office Action dated Jul. 24, 2014", 26 pgs.
"U.S. Appl. No. 12/255,945, Non Final Office Action dated Aug. 4, 2011", 12 pgs.
"U.S. Appl. No. 12/255,945, Reply Brief filed Apr. 13, 2015", 4 pgs.
"U.S. Appl. No. 12/255,945, Response filed Jan. 17, 2012 to Final Office Action dated Nov. 28, 2011", 11 pgs.
"U.S. Appl. No. 12/255,945, Response filed Jan. 28, 2014 to Final Office Action dated Sep. 30, 2013", 13 pgs.
"U.S. Appl. No. 12/255,945, Response filed Feb. 28, 2012 to Advisory Action dated Feb. 10, 2012", 13 pgs.
"U.S. Appl. No. 12/255,945, Response filed Jul. 7, 2011 to Restriction Requirement dated Jun. 7, 2011", 8 pgs.
"U.S. Appl. No. 12/255,945, Response filed Aug. 8, 2013 to Non Final Office Action dated May 7, 2013", 13 pgs.
"U.S. Appl. No. 12/255,945, Response filed Nov. 4, 2011 to Non Final Office Action dated Aug. 4, 2011", 14 pgs.
"U.S. Appl. No. 12/255,945, Restriction Requirement dated Jun. 7, 2011", 8 pgs.
"U.S. Appl. No. 12/255,945, Supplemental Amendment filed Mar. 5, 2014", 13 pgs.
"U.S. Appl. No. 12/371,096, Examiner Interview Summary dated Jan. 13, 2012", 3 pgs.
"U.S. Appl. No. 12/371,096, Examiner Interview Summary dated Dec. 5, 2013", 3 pgs.
"U.S. Appl. No. 12/371,096, Final Office Action dated Jul. 6, 2011", 23 pgs.
"U.S. Appl. No. 12/371,096, Final Office Action dated Nov. 25, 2011", 14 pgs.
"U.S. Appl. No. 12/371,096, Non Final Office Action dated Mar. 30, 2011", 19 pgs.
"U.S. Appl. No. 12/371,096, Non Final Office Action dated Apr. 17, 2014", 23 pgs.
"U.S. Appl. No. 12/371,096, Non Final Office Action dated Aug. 17, 2011", 15 pgs.
"U.S. Appl. No. 12/371,096, Non Final Office Action dated Aug. 28, 2014", 21 pgs.
"U.S. Appl. No. 12/371,096, Notice of Allowance dated Aug. 7, 2013", 12 pgs.
"U.S. Appl. No. 12/371,096, Notice of Allowance dated Nov. 5, 2013", 2 pgs.

(56) References Cited

OTHER PUBLICATIONS

"U.S. Appl. No. 12/371,096, Notice of Allowance dated Nov. 15, 2013", 2 pgs.
"U.S. Appl. No. 12/371,096, Response filed Jan. 16, 2012 to Final Office Action dated Nov. 25, 2011", 15 pgs.
"U.S. Appl. No. 12/371,096, Response filed Aug. 29, 2011 to Non Final Office Action dated Aug. 17, 2011", 19 pgs.
"U.S. Appl. No. 12/389,901, Applicant's Summary of Examiner Interview filed Nov. 28, 2011", 1 pg.
"U.S. Appl. No. 12/389,901, Examiner Interview Summary dated Nov. 1, 2011", 3 pgs.
"U.S. Appl. No. 12/389,901, Non Final Office Action dated May 12, 2011", 6 pgs.
"U.S. Appl. No. 12/389,901, Notice of Allowance dated Sep. 30, 2011", 12 pgs.
"U.S. Appl. No. 12/389,901, Notice of Allowance dated Dec. 7, 2011", 9 pgs.
"U.S. Appl. No. 12/389,901, Response filed Mar. 17, 2011 to Restriction Requirement dated Mar. 2, 2011", 8 pgs.
"U.S. Appl. No. 12/389,901, Response filed Jun. 28, 2011 to Non Final Office Action dated May 12, 2011", 11 pgs.
"U.S. Appl. No. 12/389,901, Restriction Requirement dated Mar. 2, 2011", 6 pgs.
"U.S. Appl. No. 12/483,807, Advisory Action dated Jan. 3, 2012", 2 pgs.
"U.S. Appl. No. 12/483,807, Applicant's Summary of Examiner Interview filed Jan. 19, 2012", 3 pgs.
"U.S. Appl. No. 12/483,807, Applicant's Summary of Examiner Interview filed Dec. 21, 2011", 3 pgs.
"U.S. Appl. No. 12/483,807, Non Final Office Action dated Oct. 3, 2011", 18 pgs.
"U.S. Appl. No. 12/483,807, Notice of Allowance dated Feb. 21, 2013", 9 pgs.
"U.S. Appl. No. 12/483,807, Response filed Jan. 16, 2012 to Advisory Action dated Jan. 3, 2012", 14 pgs.
"U.S. Appl. No. 12/483,807, Response filed Oct. 24, 2011 to Non Final Office Action dated Oct. 3, 2011", 16 pgs.
"U.S. Appl. No. 12/483,807, Response filed Dec. 19, 2011 to Final Office Action dated Nov. 4, 2011", 7 pgs.
"U.S. Appl. No. 12/486,992, Examiner Interview Summary dated Jan. 9, 2012", 3 pgs.
"U.S. Appl. No. 12/486,992, Examiner Interview Summary dated Mar. 9, 2012", 4 pgs.
"U.S. Appl. No. 12/486,992, Final Office Action dated Feb. 21, 2012", 8 pgs.
"U.S. Appl. No. 12/486,992, Non Final Office Action dated Nov. 21, 2011", 9 pgs.
"U.S. Appl. No. 12/486,992, Notice of Allowance dated Jun. 12, 2014", 11 pgs.
"U.S. Appl. No. 12/486,992, Preliminary Amendment filed Mar. 9, 2010", 3 pgs.
"U.S. Appl. No. 12/486,992, Response filed Jan. 17, 2012 to Non Final Office Action dated Nov. 21, 2011", 13 pgs.
"U.S. Appl. No. 12/486,992, Response filed Mar. 12, 2012 to Final Office Action dated Feb. 21, 2012", 10 pgs.
"U.S. Appl. No. 12/486,992, Response filed Oct. 24, 2011 to Restriction Requirement dated Sep. 30, 2011", 7 pgs.
"U.S. Appl. No. 12/486,992, Restriction Requirement dated Sep. 30, 2011", 6 pgs.
"U.S. Appl. No. 12/571,969, Advisory Action dated Oct. 21, 2013", 3 pgs.
"U.S. Appl. No. 12/571,969, Examiner Interview Summary dated Feb. 26, 2015", 3 pgs.
"U.S. Appl. No. 12/571,969, Examiner Interview Summary dated Mar. 11, 2013", 3 pgs.
"U.S. Appl. No. 12/571,969, Final Office Action dated Jan. 15, 2015", 9 pgs.
"U.S. Appl. No. 12/571,969, Final Office Action dated Jul. 31, 2013", 8 pgs.
"U.S. Appl. No. 12/571,969, Non Final Office Action dated Jun. 26, 2014", 8 pgs.
"U.S. Appl. No. 12/571,969, Non Final Office Action dated Dec. 19, 2012", 7 pgs.
"U.S. Appl. No. 12/571,969, Notice of Allowance dated Jun. 23, 2015", 8 pgs.
"U.S. Appl. No. 12/571,969, Preliminary Amendment filed Mar. 16, 2010", 3 pgs.
"U.S. Appl. No. 12/571,969, Response filed Mar. 6, 2013 to Non Final Office Action dated Dec. 19, 2012", 10 pgs.
"U.S. Appl. No. 12/571,969, Response filed May 15, 2015 to Final Office Action dated Jan. 15, 2015", 16 pgs.
"U.S. Appl. No. 12/571,969, Response filed Jun. 4, 2012 to Restriction Requirement dated May 9, 2012", 9 pgs.
"U.S. Appl. No. 12/571,969, Response filed Sep. 26, 2014 to Non Final Office Action dated Jun. 26, 2014", 12 pgs.
"U.S. Appl. No. 12/571,969, Response filed Sep. 30, 2013 to Final Office Action dated Jul. 31, 2013", 13 pgs.
"U.S. Appl. No. 12/571,969, Restriction Requirement dated May 9, 2012", 9 pgs.
"U.S. Appl. No. 12/714,023, Non Final Office Action dated Jan. 26, 2012", 15 pgs.
"U.S. Appl. No. 12/714,023, Notice of Allowance dated Apr. 9, 2012", 10 pgs.
"U.S. Appl. No. 12/714,023, Response filed Jan. 3, 2012 to Restriction Requirement dated Dec. 12, 2011", 9 pgs.
"U.S. Appl. No. 12/714,023, Response filed Feb. 14, 2012 to Non Final Office Action dated Jan. 26, 2012", 15 pgs.
"U.S. Appl. No. 12/714,023, Restriction Requirement dated Dec. 12, 2011", 5 pgs.
"U.S. Appl. No. 12/872,663, Non Final Office Action dated Jun. 20, 2012". 11 pgs.
"U.S. Appl. No. 12/872,663, Notice of Allowance dated Nov. 15, 2012", 9 pgs.
"U.S. Appl. No. 12/872,663, Response filed May 21, 2012 to Restriction Requirement dated Apr. 27, 2012", 7 pgs.
"U.S. Appl. No. 12/872,663, Restriction Requirement dated Apr. 27, 2012", 6 pgs.
"U.S. Appl. No. 12/872,663, Supplemental Amendment filed Nov. 8, 2012", 8 pgs.
"U.S. Appl. No. 12/888,005, Non Final Office Action dated Jun. 1, 2012", 11 pgs.
"U.S. Appl. No. 12/888,005, Notice of Allowance dated Sep. 27, 2012", 6 pgs.
"U.S. Appl. No. 12/888,005, Response filed May 15, 2012 to Restriction Requirement dated Apr. 27, 2012", 7 pgs.
"U.S. Appl. No. 12/888,005, Response filed Jul. 11, 2012 to Non Final Office Action dated Jun. 1, 2012", 12 pgs.
"U.S. Appl. No. 12/888,005, Restriction Requirement dated Apr. 27, 2012", 7 pgs.
"U.S. Appl. No. 12/893,306, Examiner Interview Summary dated Dec. 18, 2014", 3 pgs.
"U.S. Appl. No. 12/893,306, Final Office Action dated Sep. 11, 2014", 8 pgs.
"U.S. Appl. No. 12/893,306, Non Final Office Action dated Feb. 26, 2014", 9 pgs.
"U.S. Appl. No. 12/893,306, Notice of Allowability dated Jul. 29, 2015", 2 pgs.
"U.S. Appl. No. 12/893,306, Notice of Allowance dated Apr. 14, 2015", 5 pgs.
"U.S. Appl. No. 12/893,306, Response filed Jan. 12, 2015 to Final Office Action dated Sep. 11, 2014", 14 pgs.
"U.S. Appl. No. 12/893,306, Response filed May 22, 2014 to Non Final Office Action dated Feb. 26, 2014", 8 pgs.
"U.S. Appl. No. 12/893,306, Response filed Nov. 4, 2013 to Restriction Requirement dated Oct. 4, 2013", 11 pgs.
"U.S. Appl. No. 12/893,306, Restriction Requirement dated Oct. 4, 2013", 11 pgs.
"U.S. Appl. No. 12/938,905, Advisory Action dated Feb. 4, 2013", 3 pgs.
"U.S. Appl. No. 12/938,905, Appeal Brief filed Feb. 28, 2013", 1 pg.
"U.S. Appl. No. 12/938,905, Appeal Brief filed Apr. 29, 2013", 26 pgs.

(56) References Cited

OTHER PUBLICATIONS

"U.S. Appl. No. 12/938,905, Appeal Decision mailed Dec. 14, 2015", 18 pgs.
"U.S. Appl. No. 12/938,905, Examiner Interview Summary dated Jan. 30, 2013", 3 pgs.
"U.S. Appl. No. 12/938,905, Examiner Interview Summary dated Jul. 13, 2012", 3 pgs.
"U.S. Appl. No. 12/938,905, Examiner's Answer to Appeal Brief dated Jun. 24, 2013", 8 'pgs.
"U.S. Appl. No. 12/938,905, Final Office Action dated Nov. 28, 2012", 11 pgs.
"U.S. Appl. No. 12/938,905, Non Final Office Action dated Jun. 4, 2012", 11 pgs.
"U.S. Appl. No. 12/938,905, Reply Brief filed Aug. 26, 2013", 12 pgs.
"U.S. Appl. No. 12/938,905, Response filed Jan. 28, 2013 to Final Office Action dated Nov. 28, 2012", 19 pgs.
"U.S. Appl. No. 12/938,905, Response filed May 14, 2012 to Restriction Requirement dated Apr. 17, 2012", 7 pgs.
"U.S. Appl. No. 12/938,905, Response filed Jul. 19, 2012 to Non Final Office Action dated Jun. 4, 2012", 20 pgs.
"U.S. Appl. No. 12/938,905, Response filed Oct. 8, 2012 to Restriction Requirement dated Sep. 14, 2012", 8 pgs.
"U.S. Appl. No. 12/938,905, Restriction Requirement dated Apr. 17, 2012", 8 pgs.
"U.S. Appl. No. 12/938,905, Restriction Requirement dated Sep. 14, 2012", 6 pgs.
"U.S. Appl. No. 12/938,913, Advisory Action dated Jan. 15, 2015", 3 pgs.
"U.S. Appl. No. 12/938,913, Examiner Interview Summary dated Dec. 18, 2014", 3 pgs.
"U.S. Appl. No. 12/938,913, Final Office Action dated Oct. 1, 2014", 9 pgs.
"U.S. Appl. No. 12/938,913, Non Final Office Action dated Mar. 11, 2014", 10 pgs.
"U.S. Appl. No. 12/938,913, Non Final Office Action dated Apr. 9, 2015", 8 pgs.
"U.S. Appl. No. 12/938,913, Notice of Allowance dated Nov. 12, 2015", 5 pgs.
"U.S. Appl. No. 12/938,913, Response filed Jan. 2, 2015 to Final Office Action dated Oct. 1, 2014", 10 pgs.
"U.S. Appl. No. 12/938,913, Response filed Feb. 2, 2015 to Advisory Action dated Jan. 15, 2015", 14 pgs.
"U.S. Appl. No. 12/938,913, Response filed Jun. 11, 2014 to Non Final Office Action dated Mar. 11, 2014", 9 pgs.
"U.S. Appl. No. 12/938,913, Response filed Jul. 7, 2015 to Non Final Office Action dated Apr. 9, 2015", 11 pgs.
"U.S. Appl. No. 12/938,913, Response filed Nov. 6, 2013 to Restriction Requirement dated Oct. 7, 2013", 1 pg.
"U.S. Appl. No. 12/938,913, Restriction Requirement dated Oct. 7, 2013", 7 pgs.
"U.S. Appl. No. 12/955,361 , Non Final Office Action dated Mar. 27, 2013", 23 pgs.
"U.S. Appl. No. 12/955,361 , Response filed Jun. 27, 2013 to Non Final Office Action dated Mar. 27, 2013", 12 pgs.
"U.S. Appl. No. 12/955,361, Notice of Allowance dated Jul. 18, 2013", 9 pgs.
"U.S. Appl. No. 12/955,361, Notice of Allowance dated Oct. 1, 2013", 4 pgs.
"U.S. Appl. No. 12/955,361, Notice of Allowance dated Oct. 24, 2013", 4 pgs.
"U.S. Appl. No. 12/955,361, Response filed Jan. 14, 2013 to Restriction Requirement dated Dec. 14, 2012", 13 pgs.
"U.S. Appl. No. 12/955,361, Restriction Requirement dated Dec. 14, 2012", 9 pgs.
"U.S. Appl. No. 12/973,214 , Response filed Feb. 21, 2014 to Final Office Action dated Nov. 21, 2013", 16 pgs.
"U.S. Appl. No. 12/973,214, Examiner Interview Summary dated Jan. 24, 2014", 3 pgs.
"U.S. Appl. No. 12/973,214, Final Office Action dated Sep. 9, 2015", 10 pgs.
"U.S. Appl. No. 12/973,214, Final Office Action dated Nov. 21, 2013", 14 pgs.
"U.S. Appl. No. 12/973,214, Non Final Office Action dated Feb. 3, 2015", 14 pgs.
"U.S. Appl. No. 12/973,214, Non Final Office Action dated May 22, 2013", 11 pgs.
"U.S. Appl. No. 12/973,214, Notice of Allowance dated Jan. 11, 2016", 8 pgs.
"U.S. Appl. No. 12/973,214, Response filed Apr. 12, 2013 to Restriction Requirement dated Mar. 13, 2013", 9 pgs.
"U.S. Appl. No. 12/973,214, Response filed Jun. 3, 2015 to Non Final Office Action dated Feb. 3, 2015", 13 pgs.
"U.S. Appl. No. 12/973,214, Response filed Aug. 22, 2013 to Non Final Office Action dated May 22, 2013", 12 pgs.
"U.S. Appl. No. 12/973,214, Response filed Nov. 6, 2015 to Final Office Action dated Sep. 9, 2015", 14 pgs.
"U.S. Appl. No. 12/973,214, Restriction Requirement dated Mar. 13, 2013", 8 pgs.
"U.S. Appl. No. 12/978,069, Advisory Action dated Jun. 12, 2013", 3 pgs.
"U.S. Appl. No. 12/978,069, Examiner Interview Summary dated May 28, 2013", 3 pgs.
"U.S. Appl. No. 12/978,069, Final Office Action dated Mar. 25, 2013", 11 pgs.
"U.S. Appl. No. 12/978,069, Non Final Office Action dated Sep. 11, 2012", 11 pgs.
"U.S. Appl. No. 12/978,069, Notice of Allowance dated Jun. 21, 2013", 13 pgs.
"U.S. Appl. No. 12/978,069, Response filed May 23, 2013 to Final Office Action dated Mar. 25, 2013", 17 pgs.
"U.S. Appl. No. 12/978,069, Response filed Aug. 27, 2012 to Restriction Requirement dated Aug. 10, 2012", 8 pgs.
"U.S. Appl. No. 12/978,069, Response filed Dec. 10, 2012 to Non Final Office Action dated Sep. 11, 2012", 15 pgs.
"U.S. Appl. No. 12/978,069, Restriction Requirement dated Aug. 10, 2012", 11 pgs.
"U.S. Appl. No. 12/978,069, Supplemental Notice of Allowance dated Aug. 9, 2013", 3 pgs.
"U.S. Appl. No. 12/978,069, Supplemental Notice of Allowance dated Sep. 17, 2013", 2 pgs.
"U.S. Appl. No. 13/041,469, Non Final Office Action dated Mar. 22, 2013", 12 pgs.
"U.S. Appl. No. 13/041,469, Notice of Allowance dated Aug. 8, 2013", 6 pgs.
"U.S. Appl. No. 13/041,469, Notice of Allowance dated Oct. 3, 2013", 2 pgs.
"U.S. Appl. No. 13/041,469, Notice of Allowance dated Nov. 19, 2013", 2 pgs.
"U.S. Appl. No. 13/041,469, Response filed Jun. 18, 2013 to Non Final Office Action dated Mar. 22, 2013", 15 pgs.
"U.S. Appl. No. 13/041,469, Response filed Oct. 25, 2012 to Restriction Requirement dated Sep. 25, 2012", 1 pg.
"U.S. Appl. No. 13/041,469, Restriction Requirement dated Sep. 25, 2012", 5 pgs.
"U.S. Appl. No. 13/041,495, Appeal Brief filed Oct. 4, 2013", 39 pgs.
"U.S. Appl. No. 13/041,495, Examiner Interview Summary dated Feb. 20, 2013", 3 pgs.
"U.S. Appl. No. 13/041,495, Examiner Interview Summary dated Aug. 6, 2013", 3 pgs.
"U.S. Appl. No. 13/041,495, Final Office Action dated Jun. 18, 2013", 14 pgs.
"U.S. Appl. No. 13/041,495, Non Final Office Action dated Nov. 2, 2012", 10 pgs.
"U.S. Appl. No. 13/041,495, Non Final Office Action dated Dec. 31, 2013", 11 pgs.
"U.S. Appl. No. 13/041,495, Notice of Allowance dated Jun. 11, 2014", 5 pgs.
"U.S. Appl. No. 13/041,495, Response filed Jan. 31, 2013 to Non Final Office Action dated Nov. 2, 2012", 13 pgs.

(56) References Cited

OTHER PUBLICATIONS

"U.S. Appl. No. 13/041,495, Response filed Mar. 31, 2014 to Non Final Office Action dated Dec. 31, 2013", 12 pgs.
"U.S. Appl. No. 13/041,495, Response filed Oct. 8, 2012 to Restriction Requirement dated Sep. 25, 2012", 8 pgs.
"U.S. Appl. No. 13/041,495, Restriction Requirement dated Sep. 25, 2012", 7 pgs.
"U.S. Appl. No. 13/041,495, Supplemental Amendment filed Feb. 20, 2013", 15 pgs.
"U.S. Appl. No. 13/041,665, Examiner Interview Summary dated Apr. 4, 2013", 3 pgs.
"U.S. Appl. No. 13/041,665, Final Office Action dated Mar. 5, 2013", 10 pgs.
"U.S. Appl. No. 13/041,665, Non Final Office Action dated Sep. 27, 2012", 10 pgs.
"U.S. Appl. No. 13/041,665, Notice of Allowance dated May 16, 2013", 7 pgs.
"U.S. Appl. No. 13/041,665, Response filed May 3, 2013 to Final Office Action dated Mar. 5, 2013", 13 pgs.
"U.S. Appl. No. 13/041,665, Response filed Sep. 17, 2012 to Restriction Requirement dated Aug. 20, 2012", 6 pgs.
"U.S. Appl. No. 13/041,665, Response filed Dec. 27, 2012 to Non Final Office Action dated Sep. 27, 2012", 16 pgs.
"U.S. Appl. No. 13/041,665, Restriction Requirement dated Aug. 20, 2012", 9 pgs.
"U.S. Appl. No. 13/041,883, Examiner Interview Summary dated Oct. 27, 2014", 3 pgs.
"U.S. Appl. No. 13/041,883, Final Office Action dated Jan. 15, 2015", 10 pgs.
"U.S. Appl. No. 13/041,883, Final Office Action dated Feb. 11, 2016", 9 pgs.
"U.S. Appl. No. 13/041,883, Non Final Office Action dated Jun. 26, 2014", 8 pgs.
"U.S. Appl. No. 13/041,883, Non Final Office Action dated Aug. 13, 2015", 10 pgs.
"U.S. Appl. No. 13/041,883, Response filed Feb. 17, 2014 to Restriction Requirement dated Jan. 15, 2014", 3 pgs.
"U.S. Appl. No. 13/041,883, Response filed Apr. 7, 2016 to Final Office Action dated Feb. 11, 2016", 17 pgs.
"U.S. Appl. No. 13/041,883, Response filed May 15, 2015 to Final Office Action dated Jan. 15, 2015", 13 pgs.
"U.S. Appl. No. 13/041,883, Response filed Sep. 26, 2014 to Non Final Office Action dated Jun. 26, 2014", 12 pgs.
"U.S. Appl. No. 13/041,883, Response filed Nov. 6, 2015 to Non Final Office Action dated Aug. 13, 2015", 16 pgs.
"U.S. Appl. No. 13/041,883, Restriction Requirement dated Jan. 15, 2014", 9 pgs.
"U.S. Appl. No. 13/045,169, Applicant's Summary of Examiner Interview filed Sep. 21, 2015", 2 pgs.
"U.S. Appl. No. 13/045,169, Examiner Interview Summary dated Sep. 10, 2015", 3 pgs.
"U.S. Appl. No. 13/045,169, Final Office Action dated Dec. 3, 2015", 8 pgs.
"U.S. Appl. No. 13/045,169, Non Final Office Action dated Jun. 4, 2015", 8 pgs.
"U.S. Appl. No. 13/045,169, Non Final Office Action dated Sep. 24, 2014", 9 pgs.
"U.S. Appl. No. 13/045,169, Response filed May 15, 2014 to Restriction Requirement dated Mar. 14, 2014", 10 pgs.
"U.S. Appl. No. 13/045,169, Response filed Aug. 31, 2015 to Non Final Office Action dated Jun. 4, 2015", 14 pgs.
"U.S. Appl. No. 13/045,169, Response filed Dec. 23, 2014 to Non Final Office Action dated Sep. 24, 2014", 10 pgs.
"U.S. Appl. No. 13/045,169, Restriction Requirement dated Mar. 14, 2014", 10 pgs.
"U.S. Appl. No. 13/047,924, Examiner Interview Summary dated Jan. 21, 2015", 3 pgs.
"U.S. Appl. No. 13/047,924, Examiner Interview Summary dated Jan. 25, 2013", 3 pgs.
"U.S. Appl. No. 13/047,924, Examiner Interview Summary dated Sep. 5, 2013", 3 pgs.
"U.S. Appl. No. 13/047,924, Examiner Interview Summary dated Sep. 18, 2012", 3 pgs.
"U.S. Appl. No. 13/047,924, Final Office Action dated Apr. 3, 2015", 16 pgs.
"U.S. Appl. No. 13/047,924, Final Office Action dated Jul. 18, 2013", 14 pgs.
"U.S. Appl. No. 13/047,924, Non Final Office Action dated Sep. 21, 2012", 11 pgs.
"U.S. Appl. No. 13/047,924, Non Final Office Action dated Nov. 3, 2014", 14 pgs.
"U.S. Appl. No. 13/047,924, Response filed Feb. 3, 2015 to Non Final Office Action dated Nov. 3, 2014", 16 pgs.
"U.S. Appl. No. 13/047,924, Response filed May 1, 2013 to Restriction Requirement dated Apr. 1, 2013", 11 pgs.
"U.S. Appl. No. 13/047,924, Response filed Sep. 17, 2012 to Restriction Requirement dated Aug. 20, 2012", 9 pgs.
"U.S. Appl. No. 13/047,924, Response filed Oct. 18, 2013 to Final Office Action dated Jul. 18, 2013", 18 pgs.
"U.S. Appl. No. 13/047,924, Response filed Dec. 20, 2012 to Non Final Office Action dated Sep. 21, 2012", 19 pgs.
"U.S. Appl. No. 13/047,924, Restriction Requirement dated Apr. 1, 2013", 7 pgs.
"U.S. Appl. No. 13/047,924, Restriction Requirement dated Aug. 20, 2012", 8 pgs.
"U.S. Appl. No. 13/081,618, Examiner Interview Summary dated Feb. 5, 2013", 3 pgs.
"U.S. Appl. No. 13/081,618, Examiner Interview Summary dated Aug. 31, 2012".
"U.S. Appl. No. 13/081,618, Final Office Action dated Nov. 19, 2012", 8 pgs.
"U.S. Appl. No. 13/081,618, Non Final Office Action dated Jul. 25, 2012", 7 pgs.
"U.S. Appl. No. 13/081,618, Notice of Allowance dated Feb. 26, 2013", 9 pgs.
"U.S. Appl. No. 13/081,618, Response filed Aug. 23, 2012 to Non Final Office Action dated Jul. 25, 2012", 10 pgs.
"U.S. Appl. No. 13/081,618, Supplemental Notice of Allowability dated Jun. 21, 2013", 2 pgs.
"U.S. Appl. No. 13/088,787, Final Office Action dated May 20, 2015", 11 pgs.
"U.S. Appl. No. 13/088,787, Non Final Office Action dated Sep. 11, 2014", 8 pgs.
"U.S. Appl. No. 13/088,787, Notice of Allowance dated Oct. 21, 2015", 6 pgs.
"U.S. Appl. No. 13/088,787, Response filed May 12, 2014 to Restriction Requirement dated Mar. 12, 2014", 10 pgs.
"U.S. Appl. No. 13/088,787, Response filed Aug. 20, 2015 to Final Office Action dated May 20, 2015", 9 pgs.
"U.S. Appl. No. 13/088,787, Response filed Dec. 10, 2014 to Non Final Office Action dated Sep. 11, 2014", 11 pgs.
"U.S. Appl. No. 13/088,787, Restriction Requirement dated Mar. 12, 2014", 9 pgs.
"U.S. Appl. No. 13/106,295, Non Final Office Action dated Jan. 24, 2013", 14 pgs.
"U.S. Appl. No. 13/106,295, Notice of Allowance dated Aug. 1, 2013", 9 pgs.
"U.S. Appl. No. 13/106,295, Response filed Apr. 16, 2013 to Non Final Office Action dated Jan. 24, 2013", 10 pgs.
"U.S. Appl. No. 13/106,295, Response filed Dec. 20, 2012 to Restriction Requirement dated Nov. 23, 2012", 1 pg.
"U.S. Appl. No. 13/106,295, Restriction Requirement dated Nov. 23, 2012", 5 pgs.
"U.S. Appl. No. 13/111,007, Non Final Office Action dated Mar. 25, 2013", 10 pgs.
"U.S. Appl. No. 13/111,007, Notice of Allowance dated Aug. 1, 2013", 8 pgs.
"U.S. Appl. No. 13/111,007, Notice of Allowance dated Oct. 4, 2013", 2 pgs.
"U.S. Appl. No. 13/111,007, Notice of Allowance dated Nov. 7, 2013", 2 pgs.

(56) References Cited

OTHER PUBLICATIONS

"U.S. Appl. No. 13/111,007, Response filed Jun. 20, 2013 to Non Final Office Action dated Mar. 25, 2013", 12 pgs.
"U.S. Appl. No. 13/111,007, Response filed Nov. 26, 2012 to Restriction Requirement dated Sep. 24, 2012", 13 pgs.
"U.S. Appl. No. 13/111,007, Restriction Requirement dated Sep. 24, 2012", 7 pgs.
"U.S. Appl. No. 13/303,546, Non Final Office Action dated Jun. 29, 2012", 12 pgs.
"U.S. Appl. No. 13/303,546, Notice of Allowance dated Nov. 6, 2012", 10 pgs.
"U.S. Appl. No. 13/303,546, Response filed Jun. 14, 2012 to Restriction Requirement dated May 30, 2012", 7 pgs.
"U.S. Appl. No. 13/303,546, Response filed Aug. 16, 2012 to Non Final Office Action dated Jun. 29, 2012", 11 pgs.
"U.S. Appl. No. 13/303,546, Restriction Requirement dated May 30, 2012", 6 pgs.
"U.S. Appl. No. 13/303,546, Supplemental Notice of Allowance dated Jan. 8, 2013", 4 pgs.
"U.S. Appl. No. 13/303,546, Supplemental Notice of Allowance dated Feb. 13, 2013", 4 pgs.
"U.S. Appl. No. 13/343,957, Non Final Office Action dated Feb. 20, 2014", 14 pgs.
"U.S. Appl. No. 13/343,957, Notice of Allowance dated Jul. 24, 2014", 7 pgs.
"U.S. Appl. No. 13/343,957, Response filed May 20, 2014 to Non Final Office Action dated Feb. 20, 2014", 14 pgs.
"U.S. Appl. No. 13/400,652, Corrected Notice of Allowance dated Feb. 1, 2016", 2 pgs.
"U.S. Appl. No. 13/400,652, Non Final Office Action dated Jun. 17, 2015", 7 pgs.
"U.S. Appl. No. 13/400,652, Notice of Allowance dated Jan. 11, 2016", 7 pgs.
"U.S. Appl. No. 13/400,652, Response filed Jan. 28, 2015 to Restriction Requirement dated Nov. 28, 2014", 17 pgs.
"U.S. Appl. No. 13/400,652, Response filed Apr. 13, 2015 to Restriction Requirement dated Feb. 13, 2015", 16 pgs.
"U.S. Appl. No. 13/400,652, Response filed Aug. 13, 2014 to Restriction Requirement dated Jun. 13, 2014", 19 pgs.
"U.S. Appl. No. 13/400,652, Response filed Sep. 16, 2015 to Non Final Office Action dated Jun. 17, 2015", 12 pgs.
"U.S. Appl. No. 13/400,652, Restriction Requirement dated Feb. 13, 2015", 8 pgs.
"U.S. Appl. No. 13/400,652, Restriction Requirement dated Jun. 13, 2014", 9 pgs.
"U.S. Appl. No. 13/400,652, Restriction Requirement dated Nov. 28, 2014", 7 pgs.
"U.S. Appl. No. 13/527,981, Advisory Action dated Jan. 20, 2016", 3 pgs.
"U.S. Appl. No. 13/527,981, Final Office Action dated Feb. 5, 2015", 22 pgs.
"U.S. Appl. No. 13/527,981, Final Office Action dated Nov. 6, 2015", 13 pgs.
"U.S. Appl. No. 13/527,981, Non Final Office Action dated Feb. 26, 2015", 10 pgs.
"U.S. Appl. No. 13/527,981, Non Final Office Action dated Sep. 15, 2014", 19 pgs.
"U.S. Appl. No. 13/527,981, Response filed Jan. 6, 2016 to Final Office Action dated Nov. 6, 2015", 14 pgs.
"U.S. Appl. No. 13/527,981, Response filed May 27, 2014 to Restriction Requirement dated Mar. 27, 2014", 11 pgs.
"U.S. Appl. No. 13/527,981, Response filed Jul. 27, 2015 to Non-Final Office Action dated Feb. 26, 2015", 25 pgs.
"U.S. Appl. No. 13/527,981, Restriction Requirement dated Mar. 27, 2014", 7 pgs.
"U.S. Appl. No. 13/572,895, Non Final Office Action dated Nov. 7, 2013", 5 pgs.
"U.S. Appl. No. 13/572,895, Notice of Allowance dated Apr. 29, 2014", 7 pgs.
"U.S. Appl. No. 13/572,895, Response filed Feb. 7, 2014 to Non Final Office Action dated Nov. 7, 2013", 13 pgs.
"U.S. Appl. No. 13/674,531 Response Filed Mar. 30, 2016 to on-Final Office Action dated Sep. 30, 2015", 10 pgs.
"U.S. Appl. No. 13/674,531, Advisory Action dated Aug. 6, 2015", 3 pgs.
"U.S. Appl. No. 13/674,531, Final Office Action dated Apr. 29, 2015", 8 pgs.
"U.S. Appl. No. 13/674,531, Non Final Office Action dated Sep. 30, 2015", 8 pgs.
"U.S. Appl. No. 13/674,531, Non Final Office Action dated Dec. 1, 2014", 9 pgs.
"U.S. Appl. No. 13/674,531, Response filed Mar. 2, 2015 to Non Final Office Action dated Dec. 1, 2014", 12 pgs.
"U.S. Appl. No. 13/674,531, Response filed Jul. 29, 2015 to Final Office Action dated Apr. 29, 2015", 12 pgs.
"U.S. Appl. No. 13/674,531, Response filed Oct. 9, 2014 to Restriction Requirement dated Sep. 24, 2014", 3 pgs.
"U.S. Appl. No. 13/674,531, Restriction Requirement dated Sep. 24, 2014", 7 pgs.
"U.S. Appl. No. 13/713,710, Notice of Allowance dated Sep. 15, 2015", 10 pgs.
"U.S. Appl. No. 13/713,710, Response filed Aug. 25, 2015 to Restriction Requirement dated Jul. 2, 2015", 7 pgs.
"U.S. Appl. No. 13/713,710, Restriction Requirement dated Jul. 2, 2015", 6 pgs.
"U.S. Appl. No. 13/744,022, Advisory Action dated Oct. 27, 2014", 3 pgs.
"U.S. Appl. No. 13/744,022, Final Office Action dated Jul. 14, 2014", 9 pgs.
"U.S. Appl. No. 13/744,022, Non Final Office Action dated Jan. 30, 2014", 20 pgs.
"U.S. Appl. No. 13/744,022, Notice of Allowance dated Nov. 28, 2014", 9 pgs.
"U.S. Appl. No. 13/744,022, Response filed Apr. 25, 2014 to Non Final Office Action dated Jan. 30, 2014", 16 pgs.
"U.S. Appl. No. 13/744,022, Response filed Oct. 8, 2014 to Final Office Action dated Jul. 14, 2014", 15 pgs.
"U.S. Appl. No. 13/766,419, Advisory Action dated May 18, 2015", 2 pgs.
"U.S. Appl. No. 13/766,419, Final Office Action dated Jan. 13, 2015", 16 pgs.
"U.S. Appl. No. 13/766,419, Non Final Office Action dated Sep. 5, 2014", 14 pgs.
"U.S. Appl. No. 13/766,419, Response filed May 12, 2015 to Final Office Action dated Jan. 13, 2015", 13 pgs.
"U.S. Appl. No. 13/766,419, Response filed Dec. 5, 2014 to Non Final Office Action dated Sep. 5, 2014", 12 pgs.
"U.S. Appl. No. 13/800,334, Examiner Interview Summary dated Jan. 29, 2015", 4 pgs.
"U.S. Appl. No. 13/800,334, Final Office Action dated Feb. 12, 2015", 11 pgs.
"U.S. Appl. No. 13/800,334, Non Final Office Action dated Sep. 24, 2015", 14 pgs.
"U.S. Appl. No. 13/800,334, Non Final Office Action dated Oct. 22, 2014", 11 pgs.
"U.S. Appl. No. 13/800,334, Response filed Jan. 21, 2015 to Non Final Office Action dated Oct. 22, 2014", 12 pgs.
"U.S. Appl. No. 13/800,334, Response filed Jul. 10, 2015 to Final Office Action dated Feb. 12, 2015", 8 pgs.
"U.S. Appl. No. 13/800,334, Response filed Dec. 16, 2015 to Non Final Office Action dated Sep. 24, 2015", 16 pgs.
"U.S. Appl. No. 13/923,827, Advisory Action dated Oct. 9, 2014", 3 pgs.
"U.S. Appl. No. 13/923,827, Examiner Interview Summary dated Sep. 29, 2014", 3 pgs.
"U.S. Appl. No. 13/923,827, Final Office Action dated Jul. 28, 2014", 11 pgs.
"U.S. Appl. No. 13/923,827, Non Final Office Action dated Apr. 10, 2014", 9 pgs.
"U.S. Appl. No. 13/923,827, Notice of Allowance dated Oct. 29, 2014", 11 pgs.

(56) References Cited

OTHER PUBLICATIONS

"U.S. Appl. No. 13/923,827, Response filed Jul. 10, 2014 to Non Final Office Action dated Apr. 10, 2014", 13 pgs.
"U.S. Appl. No. 13/923,827, Response filed Sep. 29, 2014 to Final Office Action dated Jul. 28, 2014", 11 pgs.
"U.S. Appl. No. 13/923,827, Supplemental Notice of Allowance dated Feb. 11, 2015", 2 pgs.
"U.S. Appl. No. 13/923,827, Supplemental Notice of Allowance dated Dec. 19, 2014", 3 pgs.
"U.S. Appl. No. 14/027,340, Advisory Action dated Sep. 17, 2015", 3 pgs.
"U.S. Appl. No. 14/027,340, Final Office Action dated Jul. 8, 2015", 10 pgs.
"U.S. Appl. No. 14/027,340, Non Final Office Action dated Jan. 22, 2015", 11 pgs.
"U.S. Appl. No. 14/027,340, Non Final Office Action dated Dec. 9, 2015", 10 pgs.
"U.S. Appl. No. 14/027,340, Response filed Feb. 19, 2016 to Non Final Office Action dated Dec. 9, 2015", 13 pgs.
"U.S. Appl. No. 14/027,340, Response filed May 21, 2015 to Non Final Office Action dated Jan. 22, 2015", 14 pgs.
"U.S. Appl. No. 14/027,340, Response filed Sep. 9, 2015 to Final Office Action dated Jul. 8, 2015", 15 pgs.
"U.S. Appl. No. 14/064,970, Advisory Action dated Jan. 4, 2016", 3 pgs.
"U.S. Appl. No. 14/064,970, Final Office Action dated Oct. 19, 2015", 10 pgs.
"U.S. Appl. No. 14/064,970, Non Final Office Action dated Mar. 12, 2015", 11 pgs.
"U.S. Appl. No. 14/064,970, Response filed Jul. 8, 2015 to Non Final Office Action dated Mar. 12, 2015", 8 pgs.
"U.S. Appl. No. 14/064,970, Response filed Dec. 9, 2014 to Restriction Requirement dated Oct. 9, 2014", 11 pgs.
"U.S. Appl. No. 14/064,970, Response filed Dec. 15, 2015 to Final Office Action dated Oct. 19, 2015", 11 pgs.
"U.S. Appl. No. 14/064,970, Restriction Requirement dated Oct. 9, 2014", 9 pgs.
"U.S. Appl. No. 14/086,447, Response filed May 4, 2016 to Restriction Requirement dated Apr. 6, 2016", 7 pgs.
"U.S. Appl. No. 14/086,447, Restriction Requirement dated Apr. 6, 2016", 7 pgs.
"U.S. Appl. No. 14/100,134 Response Filed Apr. 14, 2016 to Restriction Requirement dated Feb. 24, 2016", 7 pgs.
"U.S. Appl. No. 14/100,134, Restriction Requirement dated Feb. 24, 2016", 5 pgs.
"U.S. Appl. No. 14/105,669, Non Final Office Action dated Jan. 11, 2016", 11 pgs.
"U.S. Appl. No. 14/105,669, Response filed Oct. 13, 2015 to Restriction Requirement dated Sep. 8, 2015", 7 pgs.
"U.S. Appl. No. 14/105,669, Restriction Requirement dated Sep. 8, 2015", 6 pgs.
"U.S. Appl. No. 14/106,669, Response filed Apr. 11, 2016 to Non Final Office Action dated Jan. 11, 2016", 11 pgs.
"U.S. Appl. No. 14/107,316, Non Final Office Action dated Mar. 24, 2016". 16 pgs.
"U.S. Appl. No. 14/107,316, Notice of Non-Compliant Amendment dated Dec. 30, 2015", 3 pgs.
"U.S. Appl. No. 14/107,316, Response filed Jan. 18, 2016 to Notice of Non-Compliant Amendment dated Dec. 30, 2015", 8 pgs.
"U.S. Appl. No. 14/107,316, Response filed Dec. 16, 2015 to Restriction Requirement dated Oct. 29, 2015", 8 pgs.
"U.S. Appl. No. 14/107,316, Restriction Requirement dated Oct. 29, 2015", 8 pgs.
"U.S. Appl. No. 14/159,071, Final Office Action dated May 14, 2015", 7 pgs.
"U.S. Appl. No. 14/159,071, Non Final Office Action dated Dec. 8, 2014". 14 pgs.
"U.S. Appl. No. 14/483,214, Final Office Action dated Dec. 16, 2015", 9 pgs.

"U.S. Appl. No. 14/483,214, Non Final Office Action dated Jun. 5, 2015", 8 pgs.
"U.S. Appl. No. 14/483,214, Response filed Mar. 14, 2016 to Final Office Action dated Dec. 16, 2015", 15 pgs.
"U.S. Appl. No. 14/483,214, Response filed May 15, 2015 to Restriction Requirement dated Mar. 25, 2015", 2 pgs.
"U.S. Appl. No. 14/483,214, Response filed Sep. 2, 2015 to Non Final Office Action dated Jun. 5, 2015", 13 pgs.
"U.S. Appl. No. 14/483,214, Restriction Requirement dated Mar. 25, 2015", 6 pgs.
"U.S. Appl. No. 14/658,429, Non Final Office Action dated Mar. 24, 2016", 7 pgs.
"U.S. Appl. No. 14/684,936, Non Final Office Action dated Mar. 22, 2016", 7 pgs.
"U.S. Appl. No. 14/798,809, Preliminary Amendment filed Oct. 29, 2015", 7 pgs.
"U.S. Appl. No. 14/812,583, Preliminary Amendment filed Jul. 29, 2015", 6 pgs.
"U.S. Appl. No. 14/865,762, Preliminary Amendment filed Oct. 14, 2015", 6 pgs.
"U.S. Appl. No. 14/973,057, Preliminary Amendment filed Dec. 18, 2015", 7 pgs.
"U.S. Appl. No. 14/983,077, Preliminary Amendment filed Dec. 30, 2015", 6 pgs.
"U.S. Appl. No. 15/008,528, Preliminary Amendment dated Jan. 29, 2016", 8 pgs.
"U.S. Appl. No. 15/093,384, Preliminary Amendment filed Apr. 28, 2016", 5 pgs.
"U.S. Appl. No. 12/025,414, Applicant's Summary of Examiner Interview filed Apr. 9, 2012", 4 pgs.
"U.S. Appl. No. 12/025,414, Final Office Action dated Mar. 14, 2012", 6 pgs.
"U.S. Appl. No. 12/025,414, Final Office Action dated May 1, 2012", 10 pgs.
"U.S. Appl. No. 12/025,414, Non Final Office Action dated Oct. 25, 2011", 10 pgs.
"U.S. Appl. No. 12/025,414, Notice of Allowance dated Jun. 13, 2012", 7 pgs.
"U.S. Appl. No. 12/025,414, Response filed Apr. 9, 2012 to Final Office Action dated Mar. 14, 2012", 15 pgs.
"U.S. Appl. No. 12/025,414, Response filed May 21, 2012 to Final Office Action dated May 1, 2012", 6 pgs.
"U.S. Appl. No. 12/025,414, Response filed Jul. 26, 2011 to Restriction Requirement dated Jul. 19, 2011", 8 pgs.
"U.S. Appl. No. 12/025,414, Response filed Dec. 22, 2011 to Non Final Office Action dated Oct. 25, 2011", 13 pgs.
"U.S. Appl. No. 12/025,414, Restriction Requirement dated Jul. 19, 2011", 5 pgs.
"U.S. Appl. No. 12/483,807, Final Office Action dated Nov. 4, 2011", 20 pgs.
"U.S. Appl. No. 12/872,663, Response filed Sep. 13, 2012 to Non Final Office Action dated Jun. 20, 2012", 9 pgs.
"U.S. Appl. No. 13/800,334, Final Office Action dated Apr. 6, 2016", 19 pgs.
"Australian Application Serial No. 2013222609, First Examiner Report dated Feb. 16, 2015", 5 pgs.
"Australian Application Serial No. 2013222609, Response filed Sep. 17, 2015 to First Examiner Report dated Feb. 16, 2015", 17 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.

(56) References Cited

OTHER PUBLICATIONS

"Customized Patient Instruments, Primary Cruciate Retaining Surgical Technique for use with the Sigma® Knee System Utilizing Specialist® 2 Instrumentation", DePuy Orthopaedics, Inc., (2008), 1-23.

"Discovery® Elbow System", Biomet Orthopedics, Inc., (Nov. 30, 2007), 3 pgs.

"Discovery® Elbow System Surgical Technique", Biomet Orthopedics, Inc., (Dec. 31, 2008), 1-25.

"European Application Serial 13710642.3, Communication Pursuant to Article 94(3) EPC dated Nov. 6, 2015", 3 pgs.

"European Application Serial No. 07809326.7, Examination Notification Art. 94(3) dated Jan. 22, 2015", 6 pgs.

"European Application Serial No. 07809326.7, Extended European Search Report dated Nov. 15, 2011", 6 pgs.

"European Application Serial No. 07809326.7, Office Action dated Jan. 28, 2009", 2 pgs.

"European Application Serial No. 07809326.7, Office Action dated Dec. 2, 2011", 1 pg.

"European Application Serial No. 07809326.7, Response filed Jun. 6, 2012 to Extended European Search Report dated Nov. 15, 2011", 6 pgs.

"European Application Serial No. 07809326.7, Response filed Jul. 31, 2015 to Examination Notification Art. 94(3) dated Jan. 22, 2015", 10 pgs.

"European Application Serial No. 09731923.0, Examination Notification Art. 94(3) dated Feb. 10, 2015", 7 pgs.

"European Application Serial No. 09731923.0, Office Action dated Feb. 3, 2011", 2 pgs.

"European Application Serial No. 09731923.0, Response filed Aug. 20, 2015 to Examination Notification Art. 94(3) dated Feb. 10, 2015", 11 pgs.

"European Application Serial No. 09732174.9, Communication Pursuant to Article 94(3) EPC dated Mar. 3, 2016", 4 pgs.

"European Application Serial No. 09732174.9, Examination Notification Art. 94(3) dated Mar. 7, 2014", 5 pgs.

"European Application Serial No. 09732174.9, Office Action dated Feb. 3, 2011", 2 pgs.

"European Application Serial No. 09732174.9, Response filed Jul. 14, 2014 to Examination Notification Art. 94(3) dated Mar. 7, 2014", 6 pgs.

"European Application Serial No. 09792468.2, Examination Notification Art. 94(3) dated Jan. 29, 2015", 5 pgs.

"European Application Serial No. 09792468.2, Office Action dated Jul. 8, 2011", 2 pgs.

"European Application Serial No. 09792468.2, Response filed Jan. 9, 2012 to Office Action dated Jul. 8, 2011", 11 pgs.

"European Application Serial No. 09792468.2, Response filed May 29, 2015 to Examination Notification Art. 94(3) dated Jan. 29, 2015", 8 pgs.

"European Application Serial No. 10705064.3, Communication Pursuant to Article 94(3) EPC dated Dec. 8, 2015", 4 pgs.

"European Application Serial No. 10705064.3, Examination Notification Art. 94(3) dated Feb. 4, 2015", 6 pgs.

"European Application Serial No. 10705064.3, Office Action dated Nov. 22, 2011", 2 pgs.

"European Application Serial No. 10705064.3, Response filed Aug. 14, 2015 to Examination Notification Art. 94(3) dated Feb. 4, 2015", 9 pgs.

"European Application Serial No. 10705951.1, Communication Pursuant to Article 94(3) EPC dated Jan. 22, 2013", 7 pgs.

"European Application Serial No. 10705951.1, Office Action dated Oct. 7, 2011", 2 pgs.

"European Application Serial No. 10705951.1, Response filed May 23, 2013 to Communication Pursuant to Article 94(3) EPC dated Jan. 22, 2013", 8 pgs.

"European Application Serial No. 12156937.0, Decision of Grant dated May 4, 2015", 2 pgs.

"European Application Serial No. 12156937.0, Examination Notification Art. 94(3) dated Dec. 11, 2013", 5 pgs.

"European Application Serial No. 12156937.0, Extended European Search Report dated Sep. 6, 2012", 9 pgs.

"European Application Serial No. 12156937.0, Response filed Apr. 16, 2013 to Extended European Search Report dated Sep. 6, 2012", 9 pgs.

"European Application Serial No. 12156937.0, Response filed Apr. 17, 2014 to Examination Notification Art. 94(3) dated Dec. 11, 2013", 15 pgs.

"European Application Serial No. 12724475.4, Examination Notification Art. 94(3) dated Nov. 24, 2014", 7 pgs.

"European Application Serial No. 12724475.4, Office Action dated Jan. 21, 2014", 2 pgs.

"European Application Serial No. 12724475.4, Response filed Apr. 15, 2015 to Examination Notification Art. 94(3) dated Nov. 24, 2014", 9 pgs.

"European Application Serial No. 13710642.3, Office Action dated Oct. 10, 2014", 2 pgs.

"Great Britain Application Serial No. 1116054.6, Search Report dated Dec. 21, 2011", 4 pgs.

"Hipsextant Instructions of Use", Surgical Planning Associates, Inc., (2011), 19 pgs.

"International Application Serial No. PCT/EP2010/061630, International Search Report dated Nov. 30, 2010", 3 pgs.

"International Application Serial No. PCT/GB2007/003737, International Preliminary Report on Patentability dated Apr. 7, 2009", 8 pgs.

"International Application Serial No. PCT/GB2007/003737, Written Opinion dated Jan. 25, 2008", 7 pgs.

"International Application Serial No. PCT/US2007/013223, International Preliminary Report on Patentability dated Dec. 24, 2008", 5 pgs.

"International Application Serial No. PCT/US2007/013223, International Search Report dated Nov. 26, 2007", 3 pgs.

"International Application Serial No. PCT/US2007/013223, Written Opinion dated Nov. 26, 2007", 4 pgs.

"International Application Serial No. PCT/US2009/039507, International Preliminary Report on Patentability dated Oct. 28, 2010", 9 pgs.

"International Application Serial No. PCT/US2009/039507, International Search Report dated Jul. 14, 2009", 6 pgs.

"International Application Serial No. PCT/US2009/039507, Written Opinion dated Jul. 14, 2009", 7 pgs.

"International Application Serial No. PCT/US2009/039578, International Preliminary Report on Patentability dated Oct. 28, 2010", 9 pgs.

"International Application Serial No. PCT/US2009/039578, International Search Report dated Jul. 31, 2009", 6 pgs.

"International Application Serial No. PCT/US2009/039578, Written Opinion dated Jul. 31, 2009", 7 pgs.

"International Application Serial No. PCT/US2009/056670, International Preliminary Report on Patentability dated Mar. 31, 2011", 12 pgs.

"International Application Serial No. PCT/US2009/056670, International Search Report dated Mar. 2, 2010", 7 pgs.

"International Application Serial No. PCT/US2009/056670, Invitation to Pay Additional Fees and Partial Search Report dated Nov. 26, 2009".

"International Application Serial No. PCT/US2009/056670, Written Opinion dated Mar. 2, 2010", 10 pgs.

"International Application Serial No. PCT/US2009/061434, International Preliminary Report on Patentability dated May 5, 2011", 6 pgs.

"International Application Serial No. PCT/US2009/061434, International Search Report dated Feb. 2, 2010", 4 pgs.

"International Application Serial No. PCT/US2009/061434, Written Opinion dated Feb. 2, 2010", 4 pgs.

"International Application Serial No. PCT/US2010/024073, International Preliminary Report on Patentability dated Aug. 25, 2011", 8 pgs.

"International Application Serial No. PCT/US2010/024073, International Search Report dated Jun. 4, 2010", 4 pgs.

"International Application Serial No. PCT/US2010/024073, Written Opinion dated Jun. 4, 2010", 6 pgs.

(56) References Cited

OTHER PUBLICATIONS

"International Application Serial No. PCT/US2010/024579, International Preliminary Report on Patentability dated Sep. 1, 2011", 7 pgs.
"International Application Serial No. PCT/US2010/024579, International Search Report dated Apr. 22, 2010", 3 pgs.
"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 19, 2010", 6 pgs.
"International Application Serial No. PCT/US2010/024584, Written Opinion dated Aug. 19, 2010", 6 pgs.
"International Application Serial No. PCT/US2010/028325, International Preliminary Report on Patentability dated Oct. 6, 2011", 8 pgs.
"International Application Serial No. PCT/US2010/028325, International Search Report dated Nov. 6, 2010", 6 pgs.
"International Application Serial No. PCT/US2010/028325, Written Opinion dated Nov. 6, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.
"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Invitation to Pay Additional Fees dated May 3, 2011".
"International Application Serial No. PCT/US2011/026333, Written Opinion dated Aug. 9, 2011", 8 pgs.
"International Application Serial No. PCT/US2011/026412, International Preliminary Report on Patentability dated Sep. 30, 2012", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Preliminary Report on Patentability dated May 16, 2013", 11 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/038351, International Search Report dated Jul. 6, 2012", 6 pgs.
"International Application Serial No. PCT/US2012/038351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.
"International Application Serial No. PCT/US2012/060848, International Preliminary Report on Patentability dated May 8, 2014", 11 pgs.
"International Application Serial No. PCT/US2012/060848, International Search Report dated Apr. 12, 2013", 6 pgs.
"International Application Serial No. PCT/US2012/060848, Invitation to Pay Additional Fees dated Feb. 6, 2013".
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, Invitation to Pay Additional Fees dated Feb. 7, 2013", 4 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.
"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.

(56) References Cited

OTHER PUBLICATIONS

"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Preliminary Report on Patentability dated May 14, 2015", 13 pgs.
"International Application Serial No. PCT/US2013/067505, International Search Report dated Apr. 14, 2014", 5 pgs.
"International Application Serial No. PCT/US2013/067505, Invitation to Pay Additional Fees dated Feb. 6, 2014", 6 pgs.
"International Application Serial No. PCT/US2013/067505, Written Opinion dated Apr. 14, 2014", 11 pgs.
"International Application Serial No. PCT/US2013/074288, International Preliminary Report on Patentability dated Jun. 25, 2015", 13 pgs.
"International Application Serial No. PCT/US2013/074288, International Search Report dated May 23, 2014", 7 pgs.
"International Application Serial No. PCTIUS2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.
"International Application Serial No. PCT/US2014/023655, Written Opinion dated Jul. 10, 2014", 6 pgs.
"International Application Serial No. PCTIUS2014/068131, International Search Report dated May 8, 2015", 5 pgs.
"International Application U.S. Appl. No. PCT/US2014/068131, Written Opinion dated May 8, 2015", 9 pgs.
"International Application Serial No. PCT/US2015/039561, International Search Report dated Sep. 14, 2015", 5 pgs.
"International Application Serial No. PCT/US2015/039561, Written Opinion dated Sep. 14, 2015", 6 pgs.
"Is Subchondroplasty® Right for Me?", [Online] retrieved from the internet: <http://www.subchondroplast}'..com/about subchondroplast}'./ is subchondroplasty right for >, (Jul. 1, 2013), 1 pg.
"Japanese Application Serial No. 2011-505080, Appeal Decision mailed Jun. 24, 2015", (W/English Translation), 3 pgs.
"Japanese Application Serial No. 2011-505080, Decision of Refusal dated Nov. 27, 2013", 4 pgs.
"Japanese Application Serial No. 2011-505080, Office Action dated Feb. 25, 2015", (W/ English Translation), 2 pgs.
"Japanese Application Serial No. 2011-505080, Office Action dated Apr. 3, 2013", 6 pgs.
"Japanese Application Serial No. 2011-505080, Response filed Mar. 27, 2014 to Decision of Refusal dated Nov. 27, 2013", 12 pgs.
"Japanese Application Serial No. 2011-505080, Response filed May 25, 2015 to Office Action dated Feb. 25, 2015", No English Translation, 6 pgs.
"Japanese Application Serial No. 2011-505080, Response filed Jul. 3, 2013 to Office Action dated Apr. 3, 2013", 11 pgs.
"Japanese Application Serial No. 2011-527885, Office Action dated Aug. 27, 2013", (English Translation), 8 pgs.
"Japanese Application Serial No. 2011-527885, Response filed Nov. 26, 2013 to Office Action dated Aug. 27, 2013", (W/ English Translation of Claims), 9 pgs.
"Japanese Application Serial No. 2013-537691, Office Action dated Feb. 10, 2015", No English Translation, 3 pgs.
"Japanese Application Serial No. 2013-537691, Office Action dated Apr. 15, 2014", 2 pgs.
"Japanese Application Serial No. 2013-537691, Office Action dated Aug. 19, 2014", 4 pgs.
"Japanese Application Serial No. 2013-537891, Response filed Jul. 5, 2014 to Office Action dated Apr. 15, 2014", 7 pgs.
"Japanese Application Serial No. 2013-537691, Response filed Dec. 19, 2014 to Office Action dated Aug. 19, 2014", 8 pgs.
"Japanese Application Serial No. 2014-257600, Office Action dated Oct. 27, 2015", (W/ English Translation), 6 pgs.
"Japanese Application Serial No. 2014-257600, Response filed Jan. 20, 2016 to Office Action dated Oct. 27, 2015", (W/ English Translation of Claims), 5 pgs.
"Japanese Application Serial No. 2014-257600, Voluntary Amendment filed Dec. 19, 2014", 16 pgs.
"Japanese Application Serial No. 2014-511538, Office Action dated Apr. 7, 2015", (W/ English Translation), 5 pgs.
"Japanese Application Serial No. 2014-511538, Office Action dated Nov. 17, 2015", W/ English Translation, 5 pgs.
"Japanese Application Serial No. 2014-511538, Response filed Feb. 17, 2016 to Office Action dated Nov. 17, 2015", (W/ English Translation of Claims), 9 pgs.
"Japanese Application Serial No. 2014-511538, Response filed Jul. 6, 2015 to Office Action dated Apr. 7, 2015", No English Translation, 6 pgs.
"Japanese Application Serial No. 2014-558800, Office Action dated Sep. 1, 2015", (W/ English Translation), 8 pgs.
"Japanese Application Serial No. 2014-558800, Response filed Dec. 1, 2015 to Office Action dated Sep. 1, 2015", (W/ English Translation), 9 pgs.
"Japanese Application Serial No. 2014511538, Office Action dated Apr. 7, 2015", (W/ English Translation), 8 pgs.
"Knee tensor combined with laser femoral head locator", Research Disclosure, No. 507, (Jul. 2006), 903.
"Max-Ti™ Modular Protrusio Cage", Surgical Technique brochure. Biomet Orthopedics, Inc., (2003), 10 pgs.
"Max-Ti™ Modular Protrusio Cage", Surgical Technique brochure. Biomet Orthopedics, Inc., (2006), 12 pgs.
"Method for constructing an allograft sleeve", Research Disclosure, No. 476, (Dec. 2003), 1294.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Orthopaedic Salvage System Femoral/Tibial Augmentation", Biomet Orthopedics, Inc., Product Brochure, (2003, 2004), 12 pgs.
"OSS™ Orthopaedic Salvage System, Femoral/Tibial Augmentation", Biomet Orthopedics, Inc.,, (Mar. 31, 2004), 1-8.
"OSS™ Orthopaedic Salvage System, Femoral/Tibial Augmentation", Biomet Orthopedics, Inc.,, (2003), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"PAR 5™ Protrusio Acetabular Reconstruction System", Biomet Orthopedics, Inc., (2006), 12 pgs.
"Patient Matched PMI Implants, C.A.M.R.A. 3-D Imaging", Brochure, Biomet, Inc., Form Y-BMI-191/013191, (1991), 6 pgs.
"Proximal Tibial Replacement (MOST)", Zimmer MOST Options System Surgical Technique, (2005), 84 pgs.
"Regenerex® Porous Titanium Construct", Biomet brochure, (2008), 12 pgs.
"Regenerex® Tibial Cone Augment, Surgical Technique Addendum to the Vanguard® SSK Revision System", brochure. Biomet® Orthopedics., (Mar. 31, 2010), 1-8.
"Signature™ Hip Technology Personalized Patient Care brochure", Biomet® Orthopedics., (2013), 8 pgs.
"Signature™ Personalized Patient Care", Surgical Technique Acetabular Guide System brochure, Biomet® Orthopedics, (2013), 1-13.
"Signature™ Personalized Patient Care, Surgical Technique Addendum to the Vanguard Knee System", brochure. Biomet® Orthopedics, Inc., (May 15, 2009), 1-8.
"Signature™ Personalized Patient Care, Surgical Technique Addendum Vanguard® Complete Knee System", Biomet® Orthopedics Brochure, (2011), 1-32.
"Subchondroplasty", [Online] retrieved from the internet: <http://www.subchondroplasty.com/>, (Jul. 1, 2013), 1 pg.
"Taperloc Complete Hip System Surgical Technique", Biomet: Brochure 2012 REV061512, (2011), 12 pgS.
"The Oxford® Partial Knee Surgical Technique", Biomet, (Feb. 2010), 1-38.
"TruMatch™ Personalized knee replacement solutions", SIGMA® DePuy Orthopaedics, Inc, (2009), 2 pgs.

(56) References Cited

OTHER PUBLICATIONS

"United Kingdom Application Serial No. 1207103.1, Amendment filed Apr. 13, 2012", 9 pgs.
"United Kingdom Application Serial No. 1207103.1, Office Action dated May 14, 2015", 3 pgs.
"United Kingdom Application Serial No. 1207103.1, Office Action dated Oct. 6, 2015", 2 pgs.
"United Kingdom Application Serial No. 1207103.1, Response filed Sep. 14, 2015 to Office Action dated May 14, 2015", 22 pgs.
"United Kingdom Application Serial No. 1216577.5, Office Action dated Oct. 29, 2015", 4 pgs.
"United Kingdom Application Serial No. 1216577.5, Response filed Feb. 24, 2016 to Office Action dated Oct. 29, 2015", 27 pgs.
"United Kingdom Application Serial No. 1516672.1, Combined Search and Examination Report dated Oct. 22, 2015", 5 pgs.
"United Kingdom Application Serial No. 1516672.1, Office Action dated Mar. 7, 2016", 3 pgs.
"United Kingdom Application Serial No. 1516672.1, Response filed Feb. 22, 2016 to Combined Search and Examination Report dated Oct. 22, 2015", (English Translation of Claims), 37 pgs.
"United Kingdom Application Serial No. 1516672.1, Response filed Apr. 13, 2016 to Office Action dated Mar. 7, 2016", 13 pgs.
"Vanguard Complete Knee System", Biomet Othopedics, Vanguard, System Summary, (2011), 8 pgs.
"Vanguard® PFR Partial Knee Patellofemoral Replacement System", Surgical Technique, Biomet Orthopaedics,, (Aug. 31, 2010), 1-25.
"What is Subchondroplasty", [Online]. Retrieved from the Internet: <http://www.subchondroplasty.com/about subchondroplasty/what is subchondroplasty.>, (Jul. 1, 2013), 2 pgs.
"Zimmer MIS Multi-Reference 4-in-1 Femoral Instrumentation Surgical Technique", Zimmer, Inc., (2003, 2008, 2009), 48 pgs.
"Zimmer® UniSpacer® Knee System", Zimmer, Inc., (2005), 4 pgs.
Biomet, "The Oxford® Partial Knee System Surgical Technique", Biomet: Manual of the Surgical Technique, (Feb. 2010), 44 pgs.
Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.
Botha, Charl P, "Technical Report: DeVIDE—The Delft Visualisation and Image processing Development Environment", (May 31, 2006), 1-49.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
Deakon, "Posterior Cruciate Ligament Reconstruction Technique Using the Modular ACL/PCL Guide Rationale and Surgical Technique", Arthrotek®, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40,© Springer-Verlag London Limited, (2011), 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.
Friedman, R J, et al., "The Use of Computerized Tomography in the Measurement of Glenoid Version", Journal of Bone & Joint Surgery Am. (JBJS) 1992;74, (Aug. 1992), 1032-1037.
Genant, H K, et al., "Advanced CT bone imaging in osteoporosis", Rheumatology, 47, (2008), 8 pgs.

Guldberg, et al., "3D Imaging of Tissue Integration with Porous Biomaterials", Biomaterials, 29, (Oct. 2008), 3757-3761.
Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hazan, Eric J, "Computer-Assisted Orthopaedic Surgery, A New Paradigm", Techniques in Orthopaedics® vol. 18, No. 2,, (2003), 221-229.
Hutmacher, Dietmar W, "Scaffolds in tissue engineering bone and cartilage", Biomaterials, 2000 Elsevier Science Ltd., (2000), 2529-2543.
Hutmacher, Dietmar, "Scaffolds in tissue engineering bone and cartilage", Biomaterials, 21(24), (Dec. 2000), 2529-2543.
Kaus, Michael R, "Automated Segmentation of MR Images of Brain Tumors", Radiology, vol. 218, No. 2,, (2001), 586-591.
Kelly, Todd C, "Role of Navigation in Total Hip Arthroplasty", The Journal of Bone & Joint Surgery(2009) vol. 91-A, Supplement 1, (2009), 153-8.
Klein, M, "Robot assisted insertion of craniofacial implants—clinical experience", CARS 2001, Elsevier Science B.V., (2001), 133-138.
Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.
Lynch, John A, et al., "Cartilage segmentation of 3D MRI scans of the osteoarthritic knee combining user knowledge and active contours", Medical Imaging 2000: Image Processing SPIE vol. 3979, (2000), 925-935.
Murphy, S B, et al., "The Hip Sextant: Navigation of Acetabular Component Orientation Using a Mechanical Instrument", (2009), 1 pg.
Nicholls, Paul M. D, "Trauma Grand Rounds PMI (Patient-Matched Implants)", Biomet Orthopedics, Inc.,, (Feb. 29, 2000), 1 pg.
Overhoff, H M, et al., "Total Knee Arthroplasty: Coordinate System Definition and Planning based on 3-D Ultrasound Image Volumes", CARS 2001, Elsevier Science B.V., (2001), 283-288.
Patsch, J M, et al., "Noninvasive imaging of bone microarchitecture", Annals ofthe NY Academy of Sciences, (2011), 77-87.
Portheine, F, "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.
Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.
Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.
Radermacher, K, et al., "Computer Integrated Orthopaedic Surgery: Connection of Planning and Execution in Surgical Intervention", Computer-integrated surgery: technology and clinical applications, (1996), 451-463.
Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.
Radermacher, K, et al., "Image Guided Orthopedic Surgery Using Individual Templates", Springer Berlin/Heidelberg, CVRMed-MRCAS'97, vol. 1205, (1997), 606-615.
Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.

(56) References Cited

OTHER PUBLICATIONS

Radermacher, Klaus, et al., "Computer Assisted Orthopaedic Surgery with Image Based Individual Templates", Clinical Orthopaedics and Related Research No. 354, Lippincott Williams & Wilkins, (Sep. 1998), 28-38.
Schuller-Gotzburg, P, et al., "3D-Implantatplanung und Stereolithographie-Implantatbohrschablonen", Stomatologie 101.3, (May 2004), 55-59.
Sharp, Michael S, "Patient-Specific, Resurfacing Bi-Compartmental Arthuroplasty Futuretech", Orthopaedic Product News, (Apr. 2008), 12-15.
Sisto, Domenick J, et al., "Custom Patellofemoral Arthroplasty of the Knee Surgical Technique", Journal of Bone and Joint Surgery, vol. 89-A, (2006), 214-225.
Slamin, John, et al., "Do You Have This Implant in My Size?", MDT Medical Design Technology, [Online]. Retrieved from the Internet: <http://www.mdtmag.com/scripts/ShowPR.asp?PUBCODE=046&ACCT=0007796& ISSUE . . . >, (Jul. 31, 2008), 3 pgs.
Steinwachs, Matthias Reinhard, "Cartilage Repair—Autologous Chondrocyte Transplantation and Autologous Matrix-induced Chondrogenesis", European Musculoskeletal Review, (2006), 65-68.
Subburaj, K, et al., "Automated 3D Geometric Reasoning in Computer Assisted Joint Reconstructive Surgery", IEEE International Conference on Automation Science and Engineering, (2009), 367-372.
Thoma, W, et al., "Endoprothetischen Versorgung des Kniegelenks auf der Basis eines 3D-computertomographischen Subtraktionsverfahrens", Topic: Computer-aided orthopedic surgery. Orthopedist 2000 29: Springer Verlag W/ Original German Document, (2000), 641-644.
Tripp, et al., "A Nondestructuve Precreening Method for Bone Collagen Content Using Micro-Computed Tomography", Radiocarbon, vol. 52, (2010), 612-619.
U.S. Appl. No. 11/363,548 U.S. Pat. No. 7,780,672, filed Feb. 27, 2006, Femoral Adjustment Device and Associated Method.
U.S. Appl. No. 11/756,057 U.S. Pat. No. 8,092,462, filed May 31, 2007, Patient Specific Knee Alignment Guide and Associated Method.
U.S. Appl. No. 13/303,546 U.S. Pat. No. 8,398,646, filed Nov. 23, 2011, Patient Specific Knee Alignment Guide and Associated Method.
U.S. Appl. No. 13/800,334, filed Mar. 13, 2013, Patient Specific Knee Alignment Guide and Associated Method.
U.S. Appl. No. 12/103,834 U.S. Pat. No. 7,967,868, filed Apr. 16, 2008, Patient-Modified Implant and Associated Method.
U.S. Appl. No. 12/103,824, filed Apr. 16, 2008, Method and Apparatus for Manufacturing an Implant.
U.S. Appl. No. 13/081,618 U.S. Pat. No. 8,486,150, filed Apr. 7, 2011, Patient-Modified Implant.
U.S. Appl. No. 14/658,429, filed Mar. 16, 2015, Patient-Modified Implant.
U.S. Appl. No. 13/041,883, filed Mar. 7, 2011, Patient-Specific Femoral Guide.
U.S. Appl. No. 13/923,827 U.S. Pat. No. 8,979,936, filed Jun. 21, 2013, Patient-Modified Implant
U.S. Appl. No. 13/041,495 U.S. Pat. No. 8,864,769, filed Mar. 7, 2011, Alignment Guides With Patient-Specific Anchoring Elements.
U.S. Appl. No. 13/041,469 U.S. Pat. No. 8,608,749, filed Mar. 7, 2011, Patient-Specific Acetabular Guides and Associated Intruments.
U.S. Appl. No. 13/047,924, filed Mar. 15, 2011, Patient-Specific Augments.
U.S. Appl. No. 13/045,169, filed Mar. 10, 2011, Instrument With Transparent Portion for Use With Patient-Specific Alignment Guide.
U.S. Appl. No. 13/400,652 U.S. Pat. No. 9,339,278, filed Feb. 21, 2012, Patient-Specific Acetabular Guides and Associated Instruments.
U.S. Appl. No. 14/483,214, filed Sep. 11, 2014, Alignment Guides With Patient-Specific Anchoring Elements.
U.S. Appl. No. 14/105,669, filed Dec. 13, 2013, Patient-Specific Acetabular Guides and Associated Instruments.

U.S. Appl. No. 14/812,583, filed Jul. 29, 2015, Patient-Specific Augments.
U.S. Appl. No. 12/872,663 U.S. Pat. No. 8,407,067, filed Aug. 31, 2010, Method and Apparatus for Manufacturing an Implant.
U.S. Appl. No. 13/766,419, filed Feb. 13, 2013, Method and Apparatus for Manufacturing an Implant.
U.S. Appl. No. 13/739,160, filed Jun. 15, 2015, Method and Apparatus for Manufacturing an Implant.
U.S. Appl. No. 11/971,390 U.S. Pat. No. 8,070,752, filed Jan. 9, 2008, Patient Specific Alignment Guide and Inter-Operative Adjustment.
U.S. Appl. No. 12/025,414 U.S. Pat. No. 8,298,237, filed Feb. 4, 2008, Patient Specific Guide for Multiple Incisions.
U.S. Appl. No. 12/371,096, filed Feb. 13, 2009, Method and Apparatus for Manufacturing an Implant.
U.S. Appl. No. 12/483,807 U.S. Pat. No. 8,473,305, filed Jun. 12, 2009, Method and Apparatus for Manufacturing an Implant.
U.S. Appl. No. 12/039,849 U.S. Pat. No. 8,282,646, filed Feb. 29, 2008, Patient Specific Knee Alignment Guide and Associated Method.
U.S. Appl. No. 12/211,407 U.S. Pat. No. 8,608,748, filed Sep. 16, 2008, Patient Specific Guides.
U.S. Appl. No. 14/107,316, filed Dec. 16, 2013, Patient-Specific Guides.
U.S. Appl. No. 12/389,901 U.S. Pat. No. 8,133,234, filed Feb. 20, 2009, Patient Specific Acetabular Guide and Method.
U.S. Appl. No. 13/343,957 U.S. Pat. No. 8,900,244, filed Jan. 5, 2012, Patient Specific Acetabular Guides and Method.
U.S. Appl. No. 12/,486,992 U.S. Pat. No. 8,858,561, filed Jun. 18, 2000, Patient-Specific Alignment Guide.
U.S. Appl. No. 12/571,969 U.S. Pat. No. 9,173,661, filed Oct. 1, 2009, Patient Specific Alignment Guide With Cutting Surface and Laser Indicator.
U.S. Appl. No. 14/865,762, filed Sep. 25, 2015, Patient Specific Alignment Guide With Cutting Surface and Laser Indicator.
U.S. Appl. No. 12/714,023 U.S. Pat. No. 8,241,293, filed Feb. 26, 2010, Patient Specific High Tibia Osteotomy.
U.S. Appl. No. 13/572,895 U.S. Pat. No. 8,828,087, filed Aug. 13, 2012, Patient-Specific High Tibia Osteotomy.
U.S. Appl. No. 12/888,005 U.S. Pat. No. 8,377,066, filed Sep. 22, 2010, Patient-Specific Elbow Guides and Associated Methods.
U.S. Appl. No. 13/744,022 U.S. Pat. No. 9,005,297, filed Jan. 17, 2013, Patient-Specific Elbow Guides and Associated Methods.
U.S. Appl. No. 14/684,936, filed Apr. 13, 2015, Patient-Specific Elbow Guides and Associated Methods.
U.S. Appl. No. 12/893,306 U.S. Pat. No. 9,113,971, filed Sep. 29, 2010, Femoral Acetabular Impingement Guide.
U.S. Appl. No. 14/798,809, filed Jul. 14, 2015, Femoral Acetabular Impingement Guide.
U.S. Appl. No. 12/938,913 U.S. Pat. No. 9,289,253, filed Nov. 3, 2010, Patient-Specific Shoulder Guide.
U.S. Appl. No. 15/008,528, filed Jan. 28, 2016, Patient-Specific Shoulder Guide.
U.S. Appl. No. 12/938,905, filed Nov. 3, 2010, Patient-Specific Implants.
U.S. Appl. No. 12/955,361 U.S. Pat. No. 8,591,516, filed Nov. 29, 2010, Patient-Specific Orthopedic Instruments.
U.S. Appl. No. 12/973,214, filed Dec. 20, 2010, Patient-Specific Pre-Operative Planning.
U.S. Appl. No. 15/093,384, filed Apr. 7, 2016, Patient-Specific Pre-Operative Planning.
U.S. Appl. No. 12/255,945, filed Oct. 22, 2008, Mechanical Axis Alignment Using MRI Imaging.
U.S. Appl. No. 12/978,069 U.S. Pat. No. 8,568,487, filed Dec. 23, 2010, Patient-Specific Hip Joint Devices.
U.S. Appl. No. 14/064,970, filed Oct. 28, 2013, Patient-Specific Hip Joint Devices.
U.S. Appl. No. 13/041,665 U.S. Pat. No. 8,535,387, filed Mar. 7, 2011, Patient-Specific Tools and Implants.
U.S. Appl. No. 14/027,340, filed Sep. 16, 2013, Patient-Specific Tools and Implants.
U.S. Appl. No. 13/111,007 U.S. Pat. No. 8,603,180, filed May 19, 2011, Patient-Specific Acetabular Guides and Associated Instruments.

(56) References Cited

OTHER PUBLICATIONS

U.S. Appl. No. 14/100,134, filed Dec. 9, 2013, Patient-Specific Acetabular Alignment Guides.
U.S. Appl. No. 13/527,981, filed Jun. 20, 2012, Backup Surgical Instrument System and Method.
U.S. Appl. No. 12/358,664 U.S. Pat. No. 8,167,823, filed Mar. 24, 2009, Method and Apparatus for Aligning and Securing an Implant Relative to a Patient.
U.S. Appl. No. 12/486,842 U.S. Pat. No. 8,337,426, filed Jun. 18, 2009, Method and Apparatus for Aligning and Securing an Implant Relative to a Patient.
U.S. Appl. No. 13/674,531, filed Nov. 12, 2012, Method and Apparatus for Aligning and Securing an Implant Relative to a Patient.
U.S. Appl. No. 14/327,234, filed Jul. 9, 2014, Patient-Specific Knee Alignment Guide and Associated Method.
U.S. Appl. No. 13/713,710 U.S. Pat. No. 9,241,745, filed Dec. 13, 2012, Patient-Specific Femoral Version Guide.
U.S. Appl. No. 14/973,057, filed Dec. 17, 2015, Patient-Specific Femoral Version Guide.
U.S. Appl. No. 13/106,295 U.S. Pat. No. 8,632,547, filed May 12, 2011, Patient-Specific Osteotomy Devices and Methods.
U.S. Appl. No. 14/086,447, filed Nov. 21, 2013, Patient-Specific Orthopedic Instruments.
"U.S. Appl. No. 13/041,883 Advisory Action dated May 18, 2016", 3 pgs.
"U.S. Appl. No. 13/041,883, Appeal Brief filed Jul. 25, 2016", 26 pgs.
"U.S. Appl. No. 13/527,981, Non Final Office Action dated Jul. 28, 2016", 11 pgs.
"U.S. Appl. No. 13/527,981, Response Filed Oct. 28, 2016 to Non-Final Office Action dated Jul. 28, 2016", 15 pgs.
"U.S. Appl. No. 13/674,531, Notice of Allowance dated Jun. 14, 2016", 16 pgs.
"U.S. Appl. No. 13/800,334, Non Final Office Action dated Dec. 15, 2016", 26 pgs.
"U.S. Appl. No. 13/800,334, Response filed Jun. 24, 2016 to Final Office Action dated Apr. 7, 2016", 19 pgs.
"U.S. Appl. No. 14/027,340, Notice of Allowance dated May 12, 2016", 7 pgs.
"U.S. Appl. No. 14/064,970, Non Final Office Action dated Jul. 26, 2016", 12 pgs.
"U.S. Appl. No. 14/064,970, Response filed Oct. 26, 2016 to Non Final Office Action dated Jul. 26, 2016", 14 pgs.
"U.S. Appl. No. 14/086,447, Notice of Allowance dated Aug. 12, 2016", 9 pgs.
"U.S. Appl. No. 14/086,447, Preliminary Amendment filed Jul. 29, 2016", 4 pgs.
"U.S. Appl. No. 14/100,134, Notice of Allowance dated Jun. 16, 2016", 14 pgs.
"U.S. Appl. No. 14/105,669, Non Final Office Action dated Aug. 11, 2016", 5 pgs.
"U.S. Appl. No. 14/105,669, Response filed Oct. 31, 2016 to Non Final Office Action dated Aug. 11, 2016", 8 pgs.
"U.S. Appl. No. 14/107,316, Corrected Notice of Allowance dated Jul. 11, 2016", 2 pgs.
"U.S. Appl. No. 14/107,316, Examiner Interview Summary dated Jun. 10, 2016", 3 pgs.
"U.S. Appl. No. 14/107,316, Notice of Allowance dated Jun. 28, 2016", 11 pgs.
"U.S. Appl. No. 14/107,316, Response filed Jun. 13, 2016 to Non Final Office Action dated Mar. 24, 2016", 13 pgs.
"U.S. Appl. No. 14/483,214, Non Final Office Action dated Oct. 6, 2016", 12 pgs.
"U.S. Appl. No. 14/483,214, Response filed Jan. 6, 2017 to Non Final Office Action dated Oct. 6, 2016", 16 pgs.
"U.S. Appl. No. 14/658,429, Final Office Action dated Aug. 29, 2016", 9 pgs.
"U.S. Appl. No. 14/658,429, Response filed Nov. 21, 2016 to Final Office Action dated Aug. 29, 2016", 14 pgs.
"U.S. Appl. No. 14/658,429, Response Filed Jun. 20, 2016 to Non-Final Office Action dated Mar. 24, 2016", 12 pgs.
"U.S. Appl. No. 14/684,936, Corrected Notice of Allowance dated Sep. 22, 2016", 4 pgs.
"U.S. Appl. No. 14/684,936, Notice of Allowance dated Aug. 30, 2016", 6 pgs.
"U.S. Appl. No. 14/684,936, Response filed Jun. 9, 2016 to Non Final Office Action dated Mar. 22, 2016", 8 pgs.
"U.S. Appl. No. 14/798,809, Restriction Requirement dated Jan. 4, 2017", 10 pgs.
"U.S. Appl. No. 14/973,057, Non Final Office Action dated Oct. 18, 2016", 6 pgs.
"U.S. Appl. No. 14/973,057, Response filed Sep. 21, 2016 to Restriction Requirement dated Jul. 29, 2016", 5 pgs.
"U.S. Appl. No. 14/973,057, Restriction Requirement dated Jul. 29, 2016", 8 pgs.
"U.S. Appl. No. 15/224,741, Preliminary Amendment filed Sep. 12, 2016", 8 pgs.
"U.S. Appl. No. 15/267,714, Preliminary Amendment filed Oct. 6, 2016", 7 pgs.
"U.S. Appl. No. 15/267,714, Restriction Requirement dated Jan. 5, 2017", 5 pgs.
"C2a-Taper™ Ceramic-on-Ceramic Articulation", Surgical Technique, Biomet Orthopedics, (2007), 20 pgs.
"European Application Serial 13710642.3, Intention to grant dated Jun. 17, 2016", 7 pgs.
"European Application Serial 13710642.3, Response filed Mar. 16, 2016 to Communication Pursuant to Article 94(3) EPC dated Nov. 6, 2015", 8 pgs.
"European Application Serial No. 09731923.0, Communication Pursuant to Article 94(3) EPC dated Nov. 29, 2016", 5 pgs.
"European Application Serial No. 09732174.9, Communication Pursuant to Article 94(3) EPC dated Oct. 17, 2016", 4 pgs.
"European Application Serial No. 09732174.9, Response filed Jul. 13, 2016 to Communication Pursuant to Article 94(3) EPC dated Mar. 3, 2016", 12 pgs.
"European Application Serial No. 09792468.2, Communication Pursuant to Article 94(3) EPC dated Jun. 7, 2016", 4 pgs.
"European Application Serial No. 09792468.2, Response filed Sep. 28, 2016 to Communication Pursuant to Article 94(3) EPC dated Jun. 7, 2016", 21 pgs.
"European Application Serial No. 10705064.3, Response filed Apr. 18, 2016 to Communication Pursuant to Article 94(3) EPC dated Dec. 8, 2015", 8 pgs.
"European Application Serial No. 12724475.4, Communication Pursuant to Article 94(3) EPC dated Aug. 31, 2016", 5 pgs.
"European Application Serial No. 13710642.3, Amendment dated Sep. 1, 2014", 7 pgs.
"Japanese Application Serial No. 2014-257600, Examiners Decision of Final Refusal dated Dec. 20, 2016", No English Translation, 1 pg.
"Japanese Application Serial No. 2014-257600, Office Action dated May 24, 2016", (W/ English Translation), 5 pgs.
"United Kingdom Application Serial No. 1116054.6, Office Action dated Aug. 12, 2016", 2 pgs.
"United Kingdom Application Serial No. 1116054.6, Response filed Oct. 11, 2016 to Office Action dated Aug. 12, 2016", 12 pgs.
"United Kingdom Application Serial No. 11160546, First Examination Report dated Jun. 6, 2016", 4 pgs.
"United Kingdom Application Serial No. 1216577.5, Office Action dated Oct. 20, 2016", 4 pgs.
"United Kingdom Application Serial No. 1216577.5, Response filed Oct. 25, 2016 to Office Action dated Oct. 20, 2016", 24 pgs.
"United Kingdom Application Serial No. 1308746.5, Office Action dated Oct. 14, 2016", 5 pgs.
"Vision Acetabular Surgical TechniQue", Biomet Orthopedics, Inc brochure, (2001), 16 pgs.
Hitt, Kirby, et al., "Anthropometric Measurements of the Human Knee: Correlation to the Sizing of Current Knee Arthroplasty Systems", The Journal of Bone & Joint Surgery, (2003), 114-122.
U.S. Appl. No. 15/224,741, filed Aug. 1, 2016, Patient-Specific Tools and Implants.

(56) References Cited

OTHER PUBLICATIONS

U.S. Appl. No. 15/267,714, filed Sep. 16, 2016, Patient-Specific Acetabular Alignment Guides.
U.S. Appl. No. 15/354,721, filed Nov. 16, 2016, Patient-Specific Orthopedic Instruments.

* cited by examiner

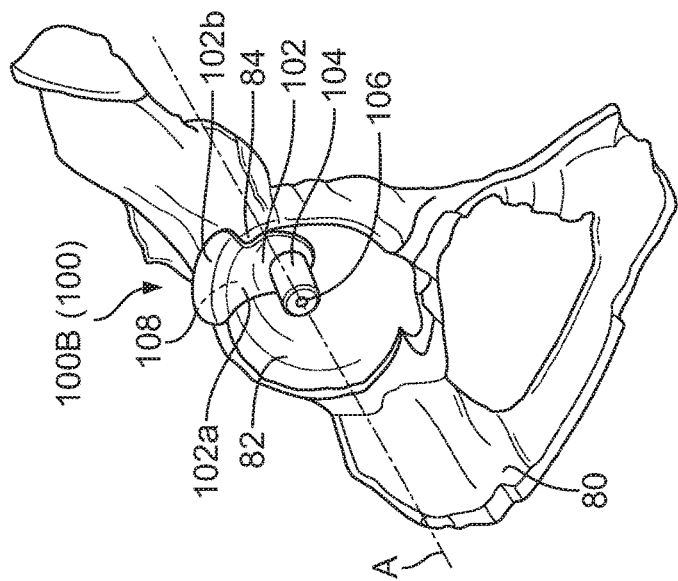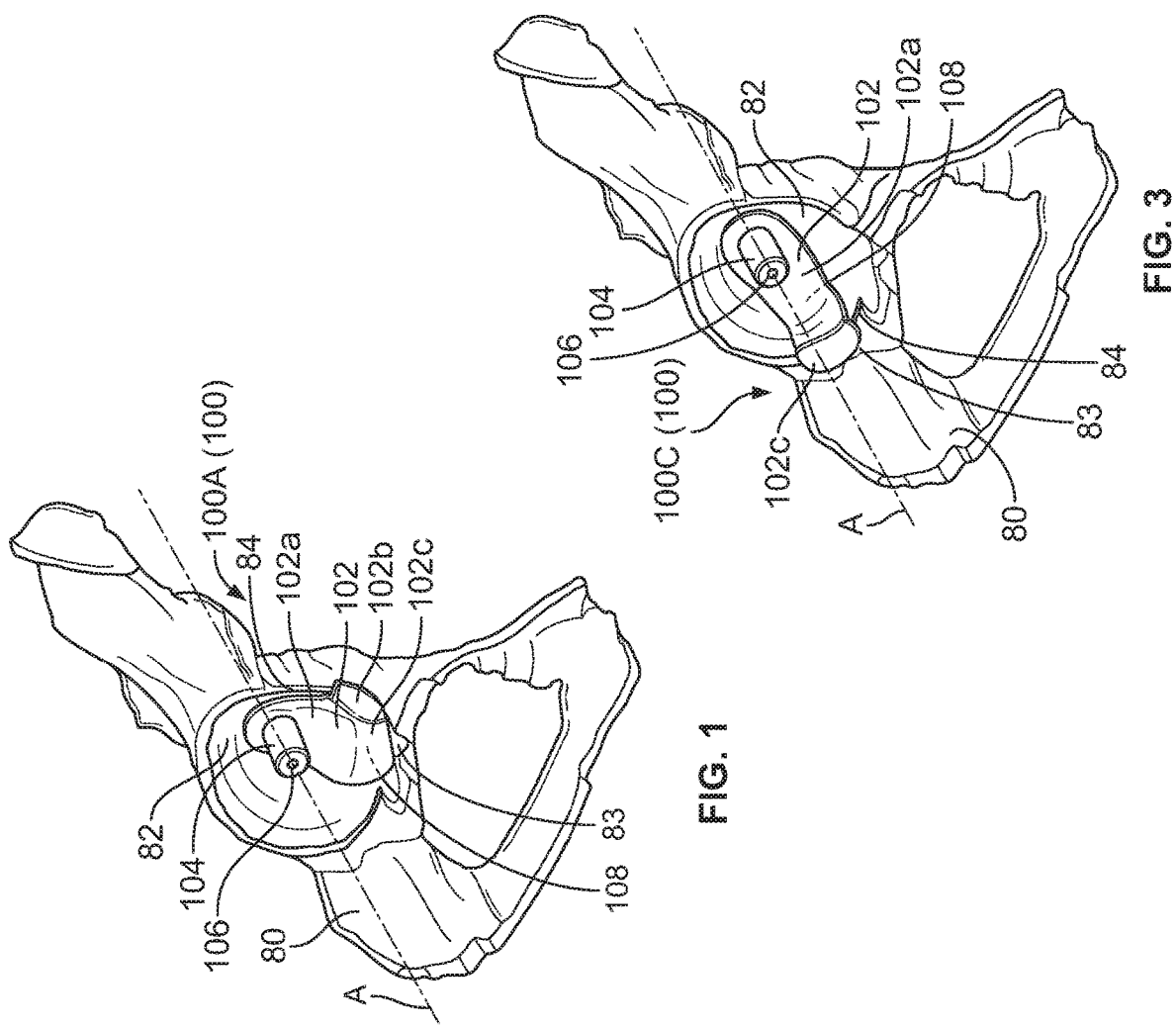

PATIENT-SPECIFIC ACETABULAR GUIDES AND ASSOCIATED INSTRUMENTS

CROSS-REFERENCE TO RELATED APPLICATIONS

This application claims the benefit of provisional application 61/446,660, filed Feb. 25, 2011 and is a divisional of U.S. application Ser. No. 13/400,652, filed on Feb. 21, 2012, now issued as U.S. Pat. No. 9,339,278.

The disclosures of the above applications are incorporated herein by reference.

INTRODUCTION

The present teachings provide a patient-specific acetabular guide and related instruments for preparing an acetabulum to receive an acetabular implant and guiding the implant into the acetabulum of a patient.

SUMMARY

The present teachings provide various instruments and methods for generally preparing the acetabulum of a patient to receive an acetabular implant, such as, for example, an acetabular cup along an alignment axis. The alignment axis and various patient-specific guides and instruments can be designed during a pre-operative plan using a three-dimensional reconstruction of the patient's relevant anatomy, such as the pelvis or portions thereof, including the acetabular and periacetabular areas of the pelvis. The three-dimensional reconstruction can be based on two-dimensional medical images, including MRI, CT or X-ray scans and prepared using commercially available imaging software.

The present teachings provide, for example, an acetabular guide that includes a patient-specific engagement surface designed to be complementary and mateable with a corresponding surface of the patient's pelvic anatomy. The acetabular guide is designed during the pre-operative plan for the patient using the three-dimensional reconstruction of the anatomy of the patient. The patient-specific engagement surface has a first portion mateable with a portion of the acetabulum of the patient. The acetabular guide includes a guiding element that extends from the acetabular guide opposite to the first portion of engagement surface. The guiding element defines a bore designed to be oriented along an alignment axis for an acetabular implant when the acetabular guide is engaged to the acetabulum. A drilling element with a stop can be used to drill a pilot hole into the acetabulum along the alignment axis.

The acetabular guide can be provided in various fitment options in which the patient-specific engagement surface is designed to fit in a unique position relative to the patient anatomy. Each fitment option of the acetabular guide includes a portion that covers a center of the acetabulum for aligning the acetabular implant and additional portions complementary to a portion of the acetabular rim and/or a portion of the transverse acetabular ligament. Each fitment option allows the acetabular guide to have a compact size, extend through the center of the acetabulum for alignment, and include portions that can fit over various anatomic landmarks in a unique position for the patient. The particular fitment option can be selected for each specific patient based on the patient's anatomy, the procedure to be performed and the surgeon's preference and/or technique.

In other embodiments according to the present teachings, the acetabular guide can include first and second marker elements extending from a portion of the acetabular guide outside the acetabulum of the patient. The marker elements define corresponding first and second bores for guiding first and second marker pins into a bone portion of the patient. A secondary guide can be used with the marker pins to orient an acetabular cup into a predetermined position and orientation. The secondary guide can be designed during the pre-operative plan to include first and second guiding elements complementary to the first and second marker elements of the acetabular guide for receiving the first and second marker pins when the first and second marker pins are attached to the bone portion of the patient.

The acetabular guide can be used according to the present teachings with a guiding handle support device that can be attached to the pelvis and provides an alignment rod as a reference for the alignment axis. The guiding handle can be removably attached to the guiding element of the acetabular guide along the alignment axis. The support device can include a connector supporting the alignment rod. The connector can be removably engaged with a shaft of the guiding handle. The support device includes rotational and translational mechanisms for orienting the alignment rod parallel to the shaft of the guiding handle and parallel to the alignment axis such that the alignment rod can provide a reference axis for the alignment axis.

The present teachings also provide a reamer having a guiding pin. The guiding pin of the reamer can be received in the pilot hole that is drilled in the acetabulum through the bore of the guiding element of the acetabular guide. The guiding pin is thus oriented along the alignment axis. In some embodiments, the reamer includes a spring that biases the guiding pin and provides tactile feedback during reaming. In some embodiments, the reamer includes a plurality of removable arcuate blades. The blades can be disposable or replaceable. In some embodiments, each blade is attached to a corresponding supporting element shaped as a spherical section, such that the supporting elements collectively form a surface corresponding to a shape of the acetabular cup.

The various instruments described above can be used in various combinations reaming the acetabulum and inserting an acetabular implant according to a pre-operative plan. In this regard the present teachings provide methods for reaming and preparing an acetabulum of a patient for an acetabular implant. One method includes engaging an acetabular area of the patient with a complementary surface of a patient-specific acetabular guide, supporting an alignment rod on a support device attached to the patient's pelvis and orienting the alignment rod to be parallel to an alignment axis for inserting the implant. The alignment axis is determined during a preoperative plan of the patient and coinciding with a center axis of a guiding element of the acetabular guide. The method further includes drilling a pilot hole in the acetabulum through a bore of the guiding element along the center axis, removing the acetabular guide, guiding an alignment pin of a reamer in the pilot hole such that the alignment pin is parallel to the alignment rod, and reaming the acetabulum.

Another method according to the present teachings includes engaging an acetabular area of the patient with a complementary surface of a patient-specific acetabular guide. The acetabular guide is designed during a pre-operative plan from a reconstructed three-dimensional image of the patient's anatomy. The method includes drilling a pilot hole in the acetabulum through a bore of a guiding element of the acetabular guide along a patient-specific alignment axis determined by the guiding bore. The method also includes inserting first and second marker pins into an area outside the acetabulum of the patient through corresponding first and second marker elements of the acetabular guide. The method includes removing the acetabular guide without removing the marker pins, reaming the acetabulum, inserting an acetabular cup in the reamed acetabulum and sliding a secondary guide over the first and second marker pins. The method further includes engaging a planar arcuate surface of the secondary guide to a complementary rim surface of the acetabular cup to align the acetabular cup to a position and orientation determined in the pre-operative plan.

Another method according to the present teachings includes using an electronic positioner for guiding an acetabular inserter into the acetabulum along a predetermined patient-specific alignment axis. The electronic positioner is capable of indicating a predetermined orientation using one or more orientation sensors. A patient-specific acetabular guide is placed on the acetabulum of the patient in a unique mated position. The acetabular guide has a guiding element oriented along the patient-specific alignment axis. A shaft of the acetabular inserter is inserted into the guiding element of the acetabular guide, such that the shaft of the acetabular inserter is oriented along the alignment axis. The electronic positioner is removably attached to the shaft of the acetabular inserter and is calibrated to indicate the alignment axis. After the acetabular guide is removed and the acetabulum prepared, the acetabular inserter with the acetabular implant can be guided along the alignment axis using feedback from the electronic positioner.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIGS. 1-5 illustrate environmental perspective views of various patient-specific acetabular alignment guides according to the present teachings;

DESCRIPTION OF VARIOUS EMBODIMENTS

Figure 4:
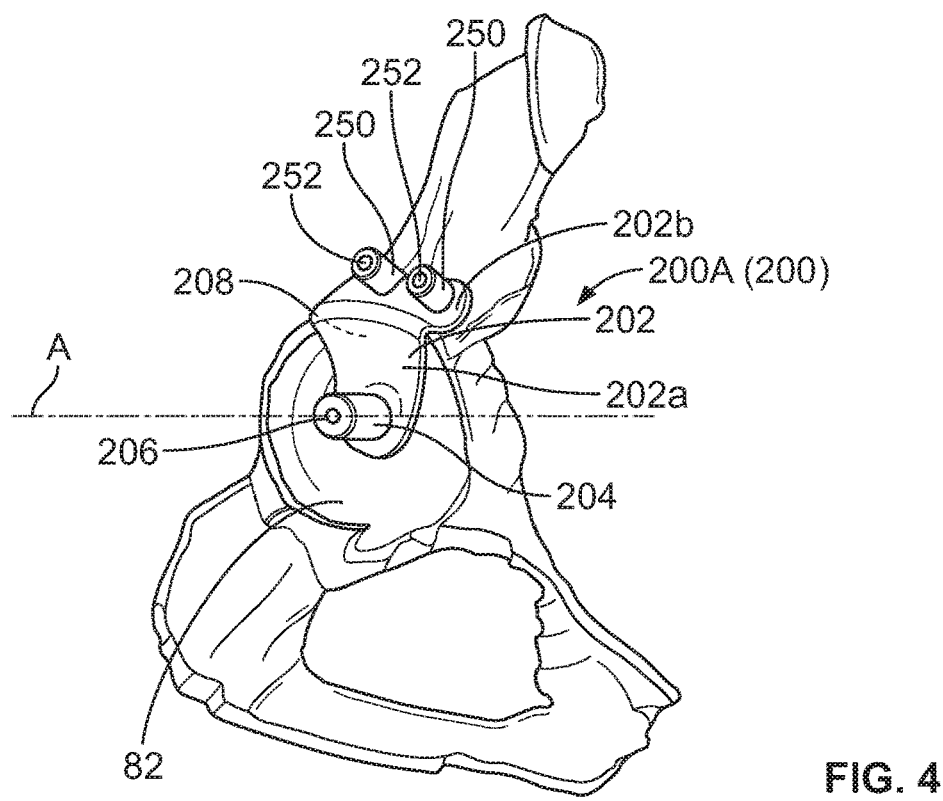

The following description is merely exemplary in nature and is in no way intended to limit the present teachings, applications, or uses.

The present teachings generally provide various patient-specific acetabular alignment guides, secondary guides, reamers, inserters, impactors and other associated instruments for use in orthopedic surgery, such as in joint replacement or revision surgery, for example. The patient-specific alignment guides and associated instruments can be used either with conventional or with patient-specific implant components prepared with computer-assisted image methods.

As described in commonly assigned U.S. application Ser. No. 11/756,057, filed on May 31, 2007, during a preoperative planning stage, imaging data of the relevant anatomy of a patient can be obtained at a medical facility or doctor's office. The imaging data can include, for example, a detailed scan of a pelvis, hip, knee, ankle or other joint or relevant portion of the patient's anatomy. The imaging data can be obtained using an MRI, CT, and X-Ray, ultrasound or any other imaging system. The imaging data obtained can be used to construct a three-dimensional computer image of the joint or other portion of the anatomy of the patient and prepare an initial pre-operative plan that can include bone or joint preparation, including planning for resections, milling, reaming, broaching, implant selection and fitting, design of patient-specific guides, templates, tools and alignment protocols for the surgical procedure.

Computer modeling for obtaining three-dimensional computer images of the relevant patient's anatomy can be provided by various CAD programs and/or software available from various vendors or developers, such as, for example, from Materialise USA, Plymouth, Mich. The computer modeling program can be configured and used to plan a preoperative surgical plan, including planning various bone preparation procedures, to select or design/modify implants and design patient-specific guides and tools including patient-specific prosthesis components, and patient-specific tools, including reaming, broaching, milling, drilling or cutting tools, alignment guides, templates and other patient-specific instruments.

The pre-operative plan can be stored in any computer storage medium, in a computer file form or any other computer or digital representation. The pre-operative plan, in a digital form associated with interactive software, can be made available via a hard medium, a web-based or mobile or cloud service, or a cellular portable device to the surgeon or other medical practitioner, for review. Using the interactive software, the surgeon can review the plan, and manipulate the position of images of various implant components relative to an image of the anatomy. The surgeon can modify the plan and send it to the manufacturer with recommendations or changes. The interactive review process can be repeated until a final, approved plan, is sent to a manufacturing facility for preparing the actual physical components.

After the surgical plan is approved by the surgeon, patient-specific implants and associated tools, including, for example, alignment guides, cutting/milling/reaming/broaching or other tools for the surgical preparation of the joint or other anatomy portion of the specific patient can be designed using a CAD program or other three-dimensional modeling software, such as the software provided by Materialise, for example, according to the preoperative surgical plan. Patient-specific guides and other instruments can be manufactured by various stereolithography methods, selective laser sintering, fused deposition modeling or other rapid prototyping methods. In some embodiments, computer instructions of tool paths for machining the patient-specific guides and/or implants can be generated and stored in a tool path data file. The tool path data can be provided as input to a CNC mill or other automated machining system, and the tools and implants can be machined from polymer, ceramic, metal or other suitable material depending on the use, and sterilized. The sterilized tools and implants can be shipped to the surgeon or medical facility for use during the surgical procedure.

Patient-specific implants, guides, templates, tools or portions thereof are defined herein as those constructed by a surgical plan approved by the surgeon using three-dimensional images of the specific patient's anatomy and made to closely conform and mate substantially as a negative mold or negative surface or inverse or mirror surface of corresponding surface portions of the patient's anatomy, including bone surfaces with or without associated soft tissue, such as articular cartilage, for example, depending on the particular procedure, implant and tool use.

Patient-specific alignment guides and implants are generally configured to match the anatomy of a specific patient and can fit in only one position on a corresponding surface of the specific patient because anatomic features that are unique to each patient function as landmarks and can guide placement of the alignment guide or implant in only one position without the need of intraoperative navigation, patient marking or other intraoperative guidance. The patient-specific alignment guides are generally configured and manufactured using computer modeling based on the patient's 3-D anatomic image and have an engagement surface that is made to conformingly contact and match as a mirror or negative or inverse surface to a corresponding surface of a three-dimensional image/model of the patient's bone surface (with or without cartilage or other soft tissue), by the computer methods discussed above. The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan. The patient-specific alignment guides can be used in minimally invasive surgery, and also in surgery with multiple minimally-invasive incisions. Various alignment guides and pre-operative planning procedures are disclosed in commonly assigned and co-pending U.S. patent application Ser. No. 11/756,057, filed on May 31, 2007, U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; and U.S. patent application Ser. No. 12/025,414, filed Feb. 4, 2008. The disclosures of the above applications are incorporated herein by reference.

Referring to FIGS. 1-5, the present teachings provide various patient-specific acetabular guides 100, 200. The acetabular guides 100, 200 can be used in connection with various other instruments to facilitate guided reaming of an acetabulum 82 of a pelvis 80 of a specific patient and guided insertion and implantation of an acetabular implant or acetabular cup in the acetabulum 82. Further, the patient-specific acetabular guides 100, 200 engage the acetabulum 82 of the specific patient in a unique (only one) position and can provide an accurate alignment axis relative to the planned orientation of the acetabular cup 280 (shown in FIG. 9, for example). The patient-specific acetabular guides 100, 200 can also provide secure fitting and rotational stability in a design that is lightweight with minimal size and bulk.

FIGS. 1-3 illustrate a patient-specific acetabular guide 100 having a patient-specific body 102, as described below, and a guiding or pilot element 104 having an elongated bore 106 with a patient-specific alignment axis A for drilling a pilot hole on the acetabulum and/or establishing the alignment axis A for a reamer, implant inserter, impactor or other instruments used in the preparation and implantation procedure. The alignment axis A is configured to be central to the acetabular cup and perpendicular to the acetabular cup's surface when the acetabular guide 100 is positioned on the acetabulum 82. The alignment axis A helps orient and guide the acetabular implant and various related instruments along a patient-specific orientation established during the preoperative plan for the patient. The acetabular guide 100 can be provided in various fitment options depending on the planned exposure of the acetabulum 82 for the reaming procedure and implantation. Each fitment option of the acetabular guide can generally include a portion that covers a center of the acetabulum for aligning the acetabular implant and additional portions complementary to a portion of the acetabular rim and/or a portion of the transverse acetabular ligament. Each fitment option allows the acetabular guide 100 to have a compact size, extend through the center of the acetabulum 82 for alignment, and include portions that can fit over various anatomic landmarks in a unique position for the patient. The particular fitment option can be selected for each specific patient based on the patient's anatomy, the procedure to be performed and the surgeon's preference and/or technique.

Three exemplary fitment options designated 100A, 100B and 100C are illustrated in FIGS. 1-3, respectively. The fitment options can include fitments engaging or registering to various combinations of portions of the acetabulum 82, the acetabular rim 84 and the transverse acetabular ligament 83. For example, the acetabular guide 100 in the fitment option 100A may engage a portion of the acetabulum 82, a portion of the acetabular rim 84 and a portion of the transverse acetabular ligament 83. In the fitment option 100B, the acetabular guide 100 may engage a portion of the acetabulum 82 and a portion of the acetabular rim 84. In the fitment option 100C, the acetabular guide 100 may engage a portion of the acetabulum 82 and a portion of the transverse acetabular ligament 83. Further details are discussed below. Either one or several acetabular guides 100A, 100B, 100C corresponding to different fitment options can be provided to the surgeon for intra-operative flexibility and plan change, according to the surgeon's preference. The acetabular guide 100 can be secured to the patient's bone with bone pins, guide wires or other fasteners.

The patient-specific body 102 of the acetabular guide 100 can include an inner portion 102a (all fitment options) from which the guiding element extends and which is designed to engage the acetabulum 82, an outer portion 102b which extends from the inner portion 102a and is configured to extend over a portion of the rim 84 (for fitment options 100A and 100C) and an outer portion 102c (fitment options 100A and 100C) configured to extend over a portion of the transverse acetabular ligament 83 (and adjacent area of the acetabulum 82). The patient specific body 102 has an underside three-dimensional engagement surface 108 that is custom-made or patient-specific to conform to and mirror (as a negative or inverse or mirror surface) complementary surfaces of various combinations of the acetabulum 82, rim 84 and/or transverse acetabular ligament 83 or other periacetabular surfaces of the pelvis 80 of the specific patient, as described above in connection with the various fitment options. The patient specific body 102 is designed by using a three-dimensional image or model of the acetabulum 82 and surrounding pelvic area of the patient, as described above. The engagement surface 108 enables the acetabular guide 100 to nest or closely mate relative to the complementarily acetabular surface of the patient. The acetabular guide 100 can be designed to have generally small thickness, such that it can form a lightweight three-dimensional shell from which the guiding element 104 extends opposite to the engagement surface. The guiding element 104 can be formed to be a monolithic or integral portion of the acetabular guide 100. Alternatively, the guiding element 104 can be modularly and removably coupled to the acetabular guide 100, using, for example, a threaded connection, snap-on connectors or other removable attachments.

Figure 5:
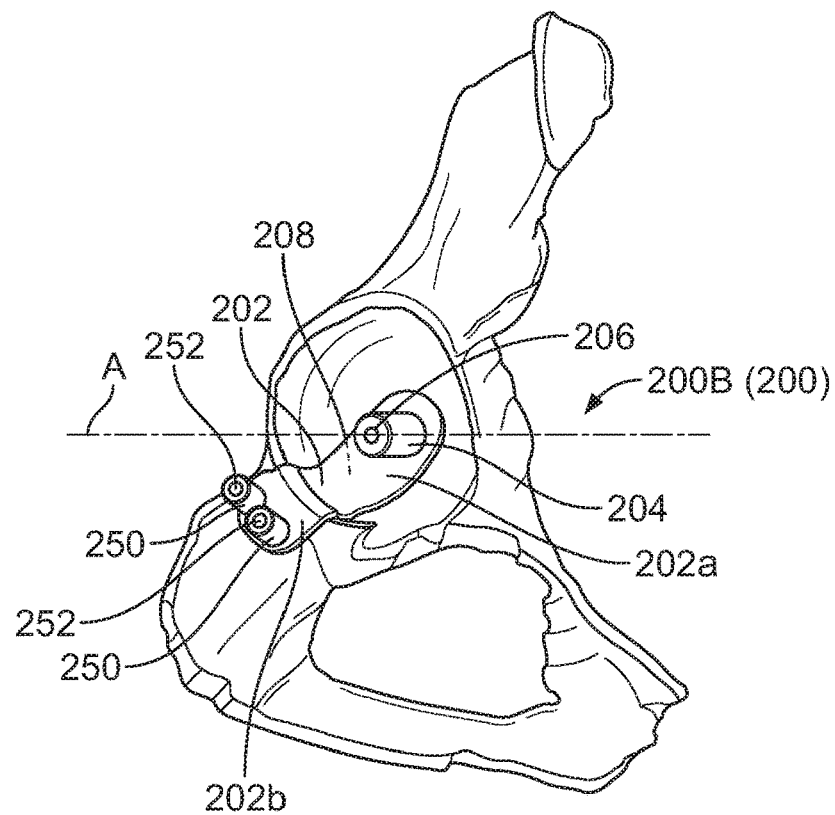
Figure 12:
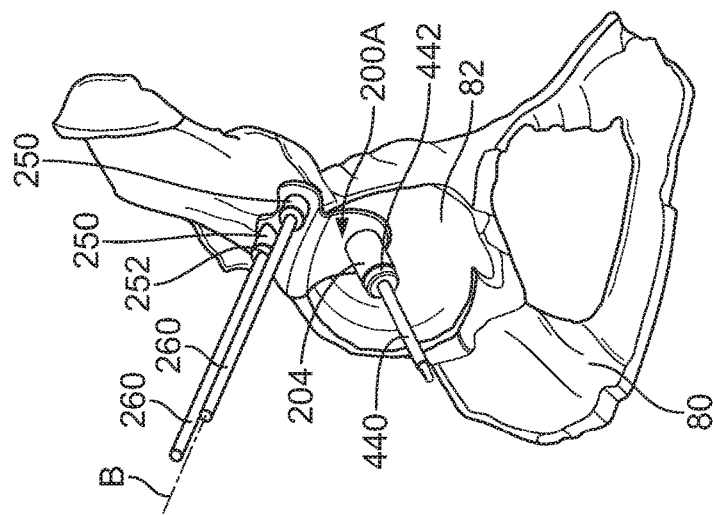
FIG. 12 is an environmental perspective view of the patient-specific acetabular alignment guide of FIG. 10 illustrating drilling a pilot hole for guided reaming according to the present teachings.
Figure 10:
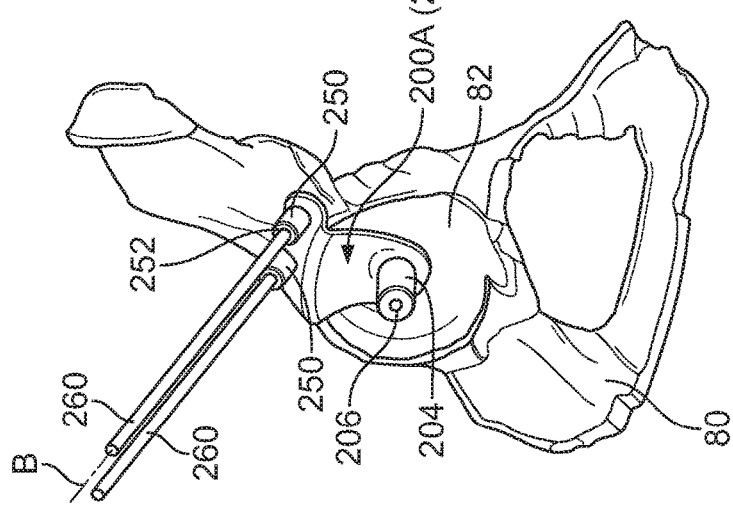
FIG. 10 is an environmental perspective view of a patient-specific acetabular alignment guide with alignment pins for a secondary guide according to the present teachings.
Figure 13:
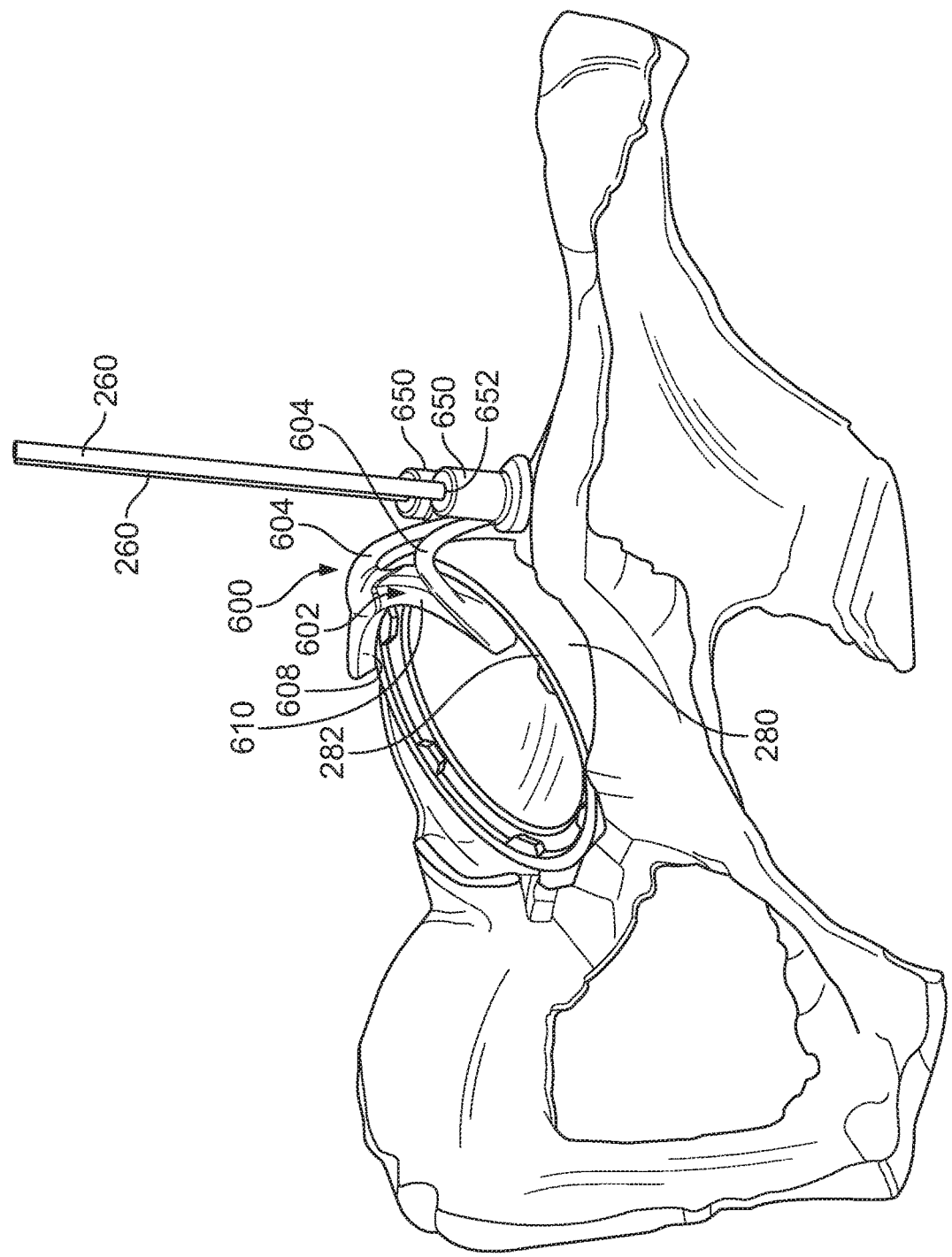
FIG. 13 is an environmental perspective view of a secondary guide over the alignment pins of FIG. 10 according to the present teachings.

Referring to FIGS. 4 and 5, another patient-specific acetabular guide 200 is illustrated with exemplary two fitment options 200A and 200B. Similarly to the acetabular guide 100, the acetabular guide 200 also includes a patient-specific body 202 and a guiding or pilot element 204 having an elongated bore 206 with an alignment axis A configured to be central to the acetabular cup and perpendicular to the acetabular cup's surface when the acetabular guide 200 is positioned on the acetabulum 82. The acetabular guide 200 can include one or more marker elements 250 (two are shown in the exemplary embodiments of FIGS. 4 and 5), each having an elongated bore 252 for guiding marker pins 260. The marker pins 260 can be used for supporting a secondary guide for another preparation method discussed below in reference to FIG. 12. The other features of the acetabular guide 200 are similar to that of the acetabular guide 100, such that the acetabular guide 200 can also be used instead of the acetabular guide 100. The acetabular guide 100 can be used for procedures in which the marker elements 250 are not utilized, as described below. The acetabular guide 200 can be used for procedures in which the marker elements 250 may or may not be utilized, as described below.

The patient-specific body 202 of the acetabular guide 200 is generally similar to patient-specific body 102 of the acetabular guide 100, such that the patient-specific body 202 can include an inner portion 202a from which the guiding element extends and which is designed to engage the acetabulum 82, and an outer portion 202b which extends from the inner portion 202a and is configured to extend over a rim portion 84 of the acetabulum 82. The outer portion 202b extends sufficiently beyond the rim 84 to the periacetabular area of pelvis to accommodate the marker elements 250. The patient specific body 202 has an underside or bone-engaging three-dimensional engagement surface 208 that is custom-made or patient-specific to conform and mirror (as an inverse or negative or mirror surface) complementary surfaces of selected portions of the acetabulum 82, the rim 84 and the transverse acetabular ligament 83 (depending on the fitment option) or other periacetabular surfaces of the pelvis 80 of the specific patient by using a three-dimensional image or model of the acetabulum and surrounding pelvic area of the patient, as described above. The engagement surface 208 enables the acetabular guide 100 to nest or closely mate relative to the complementarily acetabular surface of the patient. The acetabular guide 200 can be designed to have generally small thickness, such that it can form a lightweight three-dimensional shell from which the guiding element 204 and marker elements 250 extend.

Figure 6:
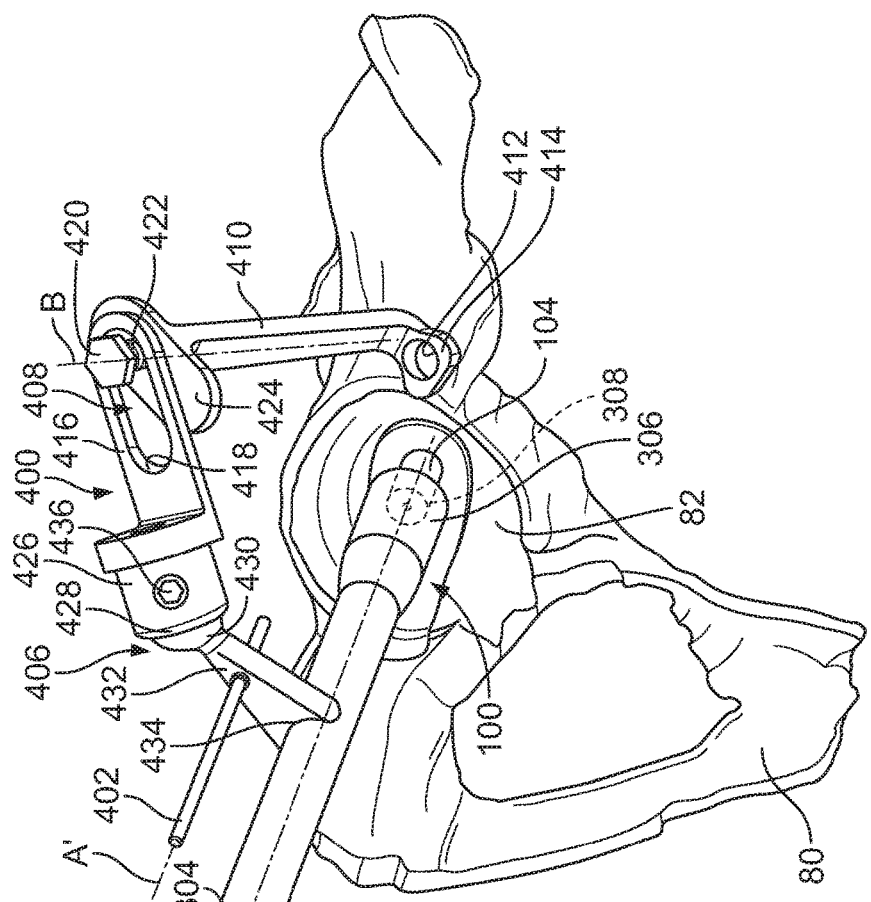
FIG. 6 is an environmental perspective view of various instruments illustrating a method for establishing an acetabular cup insertion axis according to the present teachings.

Referring to FIGS. 6-9, a method for reaming and preparing the acetabulum for an implant is described in connection with the patient-specific acetabular guides 100. The acetabular guides 200 can also be used, although the marker elements 250 are not utilized in this method. Referring to FIG. 6, a patient-specific acetabular guide 100 (or 200) is placed in a unique position on the acetabulum/rim/transverse acetabular ligament depending on the fitment option and associated anatomic landmarks of the patient, as determined in the preoperative plan for the specific patient. Once positioned, the guiding element 104 establishes the alignment axis A for the specific patient. An elongated guiding handle 300 can be attached to the guiding element 104 such that the center axis of the guiding handle 300 coincides with the alignment axis A. The guiding handle 300 can include a proximal gripping portion 302, an elongated shaft 304 extending from the gripping portion 302 and a coupling distal portion 306 which can be removably coupled to the guiding element 104, such that the guiding handle 300 is aligned along the alignment axis A. The connection can be a slidable or threadable or other connection between the distal portion 306 and the guiding element 104. The distal portion 306 can include, for example, a bore 308 for receiving the guiding element 104. The guiding element 104 and the bore 308 can be of sufficient length for the guiding handle 300 to be removably yet stably coupled to the guiding element 104 for indicating the alignment axis A without wobbling or other misaligning motion.

With continuing reference to FIG. 6, a support device or jig or outrigger 400 can be secured to the pelvis 80. The support device 400 can be used to orient an alignment pin or rod 402 along an axis A' parallel to the alignment axis A. More specifically, the support device 400 can include a universal rotational adjustment mechanism 406 and a pivotable/translational adjustment mechanism 408 for removably engaging the shaft 304 and aligning the alignment rod 402 parallel to the shaft 304 and, therefore, parallel to the alignment axis. In the exemplary embodiment of FIG. 6, the support device 400 can include a leg 410 that can be attached to the bone with a bone fastener (not shown) through a hole 412 of a foot or base 414 of the leg 410. The support device 400 can also include an arm 416 that is slidable coupled to the leg 410 to allow for translational motion of the arm 416 relative to the leg 410. The arm 416 can have, for example, an elongated slot 418 that slidably receives a fastener head 420 of a fastener 422, such as a screw or bolt that is received through a distal flange 424 of the leg 410. The flange 424 can also pivot relative to the arm 416 about an axis B along the axis of the leg 410 and fastener 422. The head 420 of the fastener 422 can be rotated to lock the flange 424 and the leg 410 relative to the arm 416. The interconnection of the arm 416, the leg 410 and the fastener 422 collectively form the pivotable/translational adjustment mechanism 408.

With continued reference to FIG. 6, the arm 416 can be substantially planar and include at a distal end a housing 426 forming a socket 428 for a ball 430 at a distal end of a connector 432. The socket 428 and the ball 430 form a universal (ball) joint of the universal rotational adjustment mechanism 406 for rotationally adjusting the connector 432 relative to the arm 416. After adjustment, the orientation of the connector 432 can be locked with a fastener 436 through the housing 426. The connector 432 supports the alignment rod 402 and includes an engagement surface 434 that can contact or engage the shaft 304, by a snap-on or other quick connect/disconnect connection. The support device 400 can be adjusted using the adjustment mechanisms 406, 408 described above such that the alignment rod 402 along axis A' is parallel to the alignment axis A of the shaft 304. In other words, the alignment rod 402 can serve as a marker for the orientation of the alignment axis A to guide reaming and cup insertion procedures as discussed below.

Figure 7:
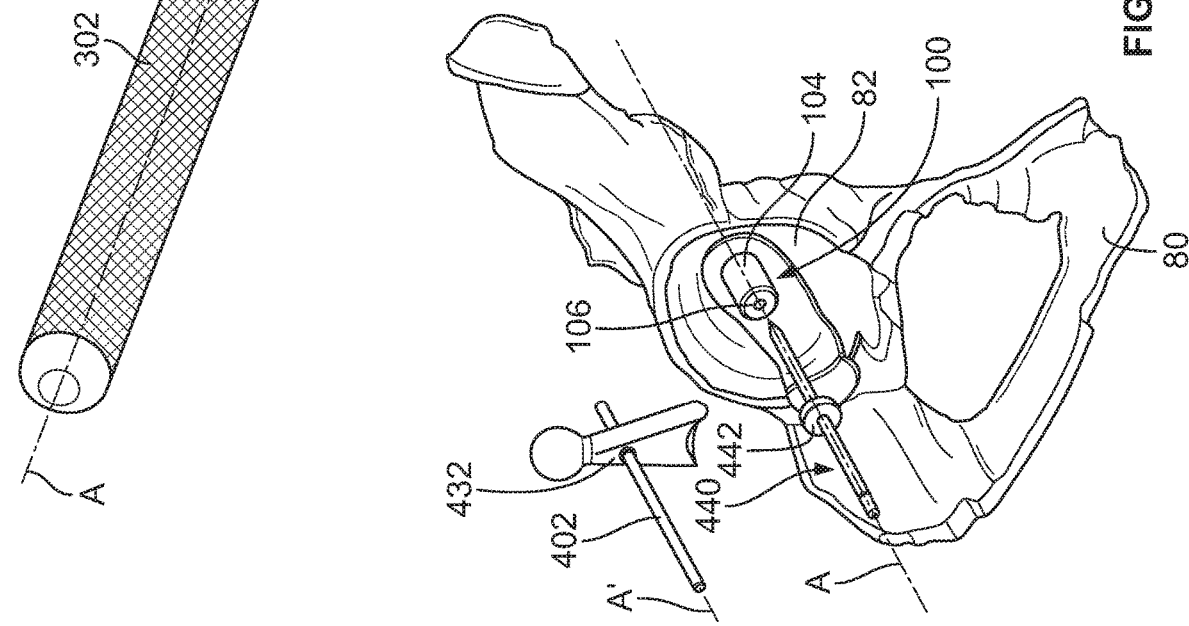
FIG. 7 is an environmental perspective view illustrating drilling a pilot hole for guided reaming according to the present teachings.
Figure 8A:
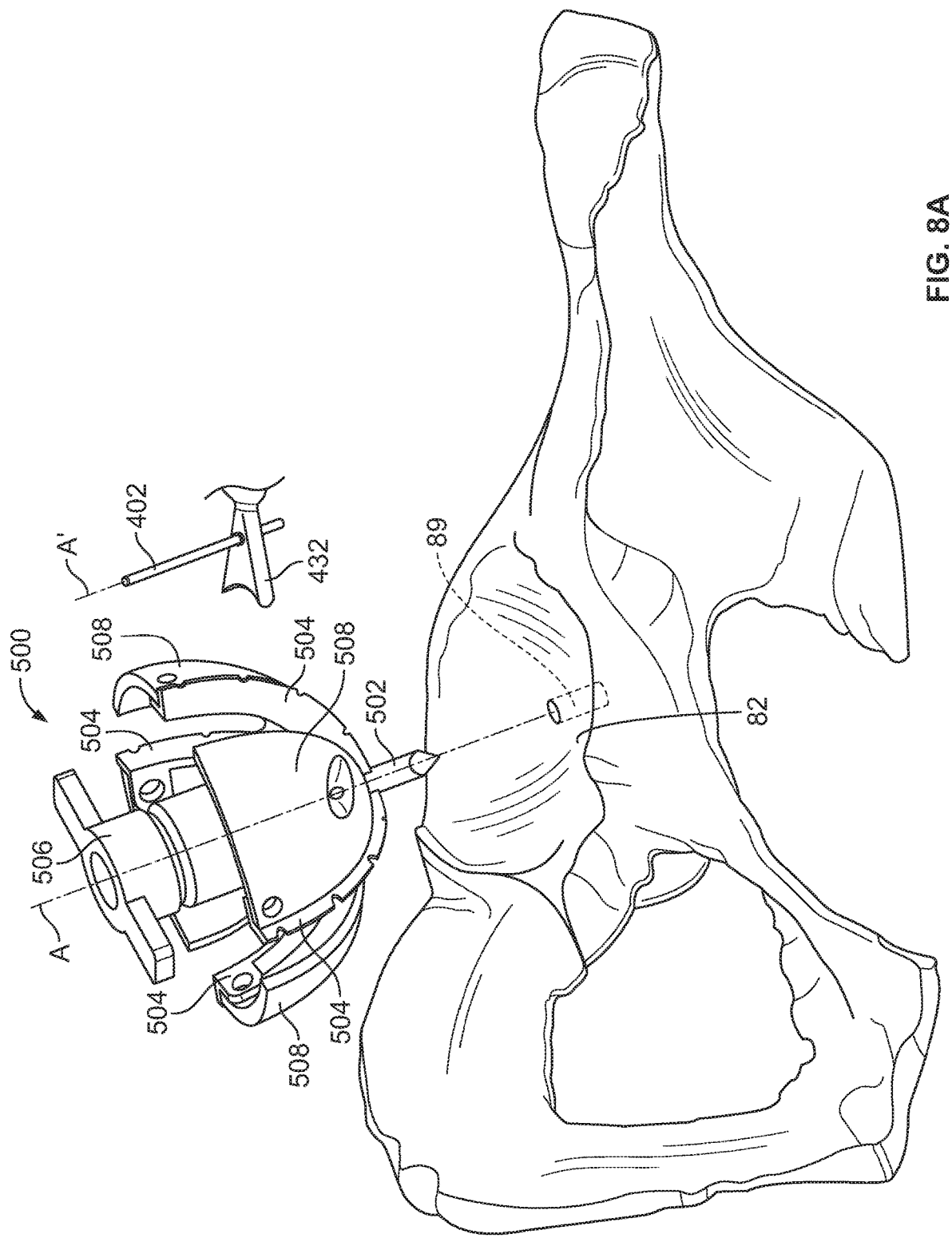
FIG. 8A is an environmental perspective view illustrating a reamer for guided reaming according to the present teachings.

After the support device 400 is locked in a position such that the orientation of the alignment rod 402 along axis A' is fixed and parallel to the alignment axis A, the guiding handle 300 is disengaged from the engagement surface 434 of the connector 432 and the acetabular guide 100 is removed. Referring to FIG. 7, a drilling element 440 can be guided through the bore 106 of the guiding element 104 of the acetabular guide 100 to drill a pilot hole 89 in the acetabulum 82 along the alignment axis A, as shown in FIG. 8A. The drilling element 440 can include a stop 442 at a pre-determined position to prevent over drilling or drilling through the wall of the acetabulum 82. The depth of drilling and the location of the stop 442 on the drilling element 440 can be determined during the pre-operative plan for the specific patient. The support device 400 and alignment rod 402 remain attached to the pelvis as shown in FIG. 6, although not fully shown in FIG. 7. After the pilot hole 89 is drilled, the acetabular guide 100 is removed.

Figure 8C:
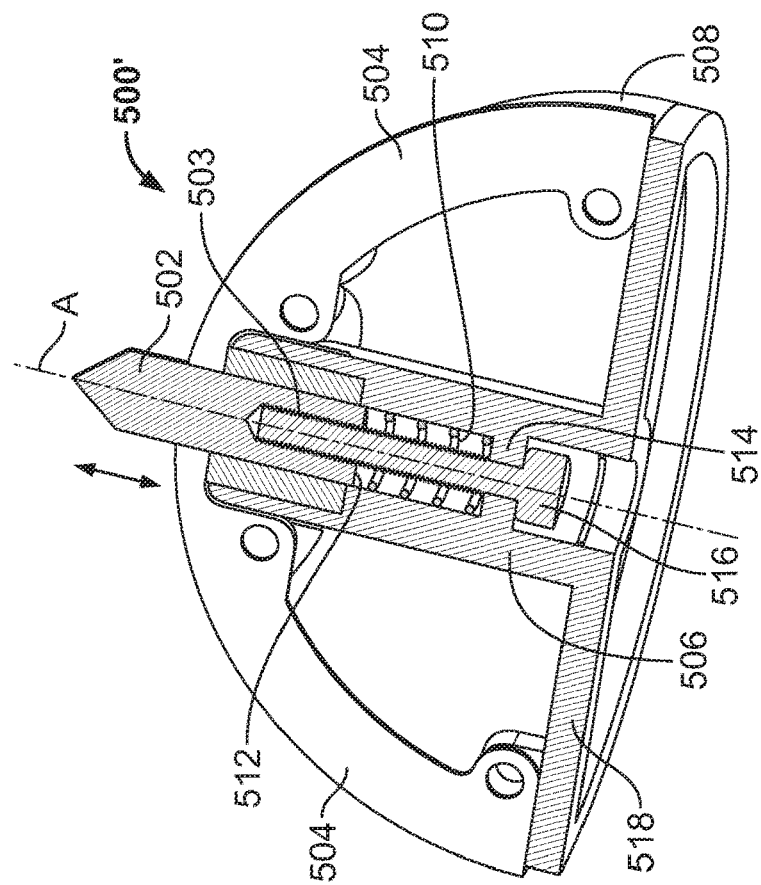
FIG. 8C is a partially sectioned perspective view of the reamer of FIG. 8B.
Figure 8B:
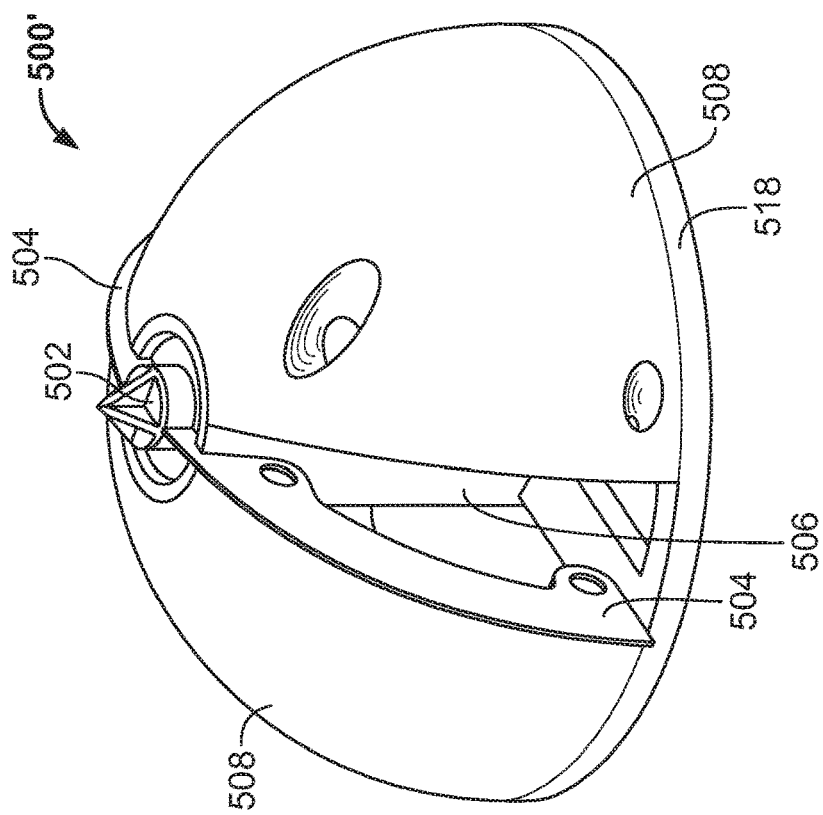
FIG. 8B is a stylized perspective view of a reamer for guided reaming according to the present teachings.

Referring to FIG. 8A, a reamer 500 can be guided along the alignment axis A to ream the acetabulum 82. Another embodiment of a reamer 500' according to the present teachings is illustrated in FIGS. 8B and 8C. The reamers 500 and 500' can be used interchangeably and similar elements will be referenced with the same numerals herein below. The reamer 500 (500') can include a trocar or other guiding pin 502 that is sized to fit and be received in the pilot hole 89 of the acetabulum 82 for stabilizing and guiding the reamer 500 (500') along the alignment axis A, i.e., at a predetermined location and orientation. This guided reaming arrangement enables the surgeon to recreate the preoperative planned position and orientation for reaming the acetabulum 82 and implanting the acetabular component. The alignment rod 402 which is supported by the support device 400 along the axis A' that is parallel to the alignment axis A can also help to guide the reamer 500 (500').

The reamer 500 (500') can include a plurality of curved reaming blades 504 and a supporting shaft 506 for a reamer driver or reamer handle. The curved blades 504 can be attached to a plurality of curved supporting elements 508 in the form of spherical leaves or spherical section/portions that collectively define a semi-spherical surface corresponding to the shape and size of the acetabular component to be implanted in the acetabulum after reaming. The blades 504 can be removable and replaceable or disposable. The entire reamer head that includes the blades 504 and the support element 508 can also be disposable. A reamer 500 with four disposable blades 504 is illustrated in FIG. 8A, while the reamer 500' shown in FIGS. 8B and 8C includes only two reamer blades 504. Referring to FIG. 8C, the guiding pin 502 can be spring biased to provide a tactile feedback during reaming. A spring or other biasing element 510 can be constrained between a proximal end 512 of the guiding pin 502 and a wall 514 of the supporting shaft 506. A set screw or fastener 516 can be used to stabilize the guiding pin 502 while allowing slidable movement along the alignment axis during reaming. The spring 510 can surround the fastener 516, as shown in FIG. 8C. Specifically, the fastener 516 is threaded to a blind bore 503 of the guiding pin 502 such that the fastener 516 and the guiding pin can move together along the alignment axis A by or against the action of the spring 510. The embodiments of FIGS. 8B and 8C also include a base ring 518 integrally attached to the shaft 506 providing additional stability.

Figure 9:
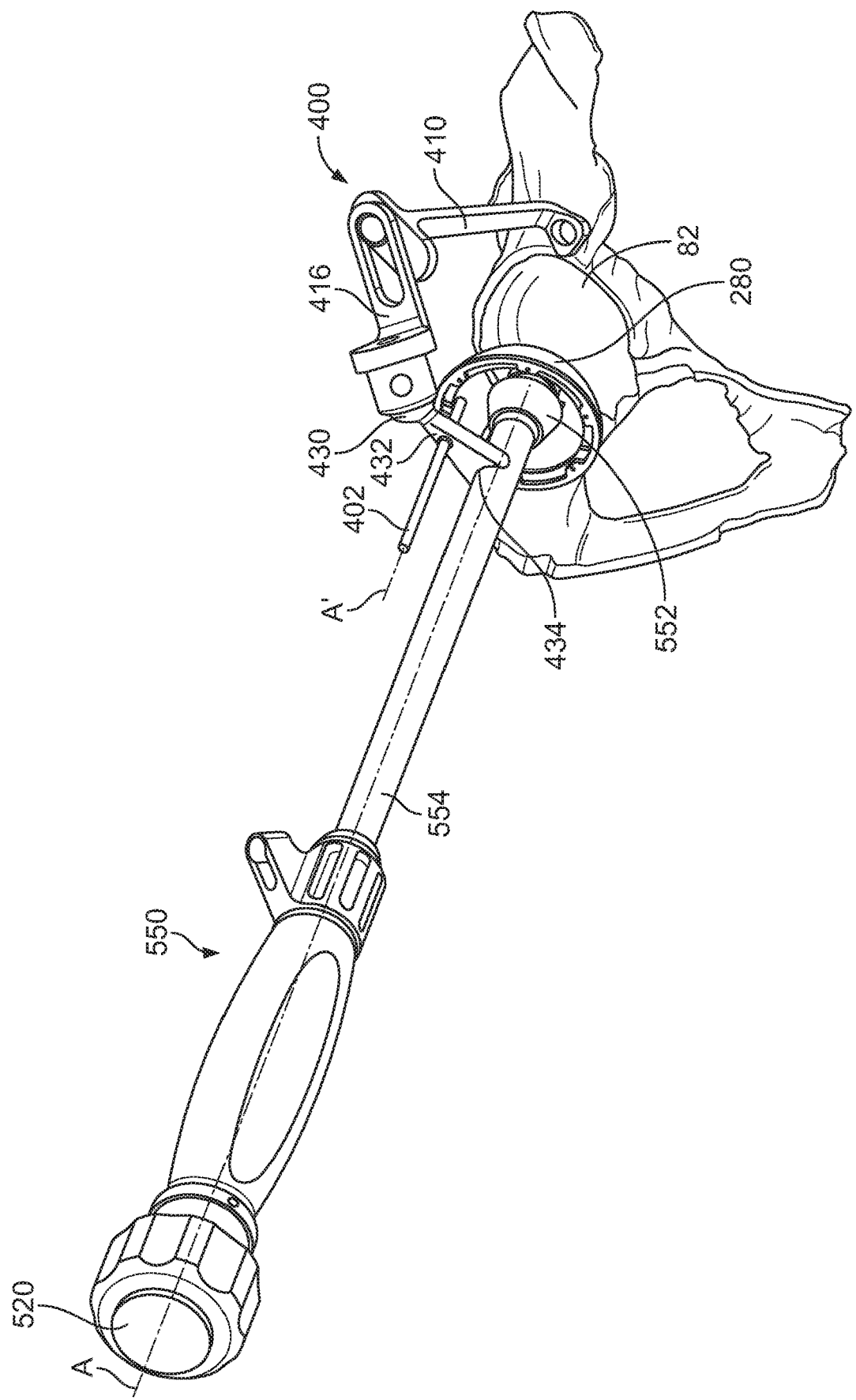
FIG. 9 is an environmental perspective view illustrating instruments for cup insertion according to the present teachings.
Figure 11:
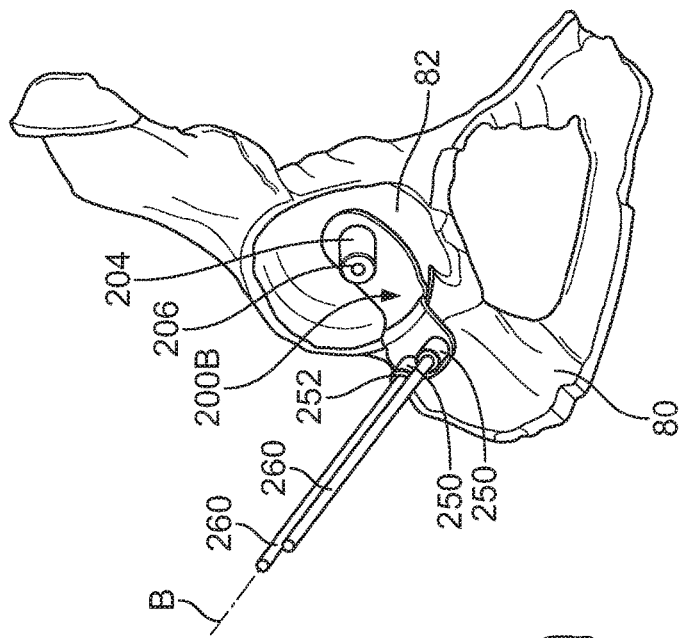
FIG. 11 is an environmental perspective view of another patient-specific acetabular alignment guide with alignment pins for a secondary guide according to the present teachings.

Referring to FIG. 9, after the acetabulum 82 has been reamed, an acetabular inserter 550 can be coupled to an acetabular cup 280 by an end coupler 552 at the distal end of a shaft 554 of the acetabular inserter 550. As seen in FIG. 9, the shaft 554 can be slidably and removably coupled or engaged to the engagement surface 434 of the connector 432 of the support device 400, such that the shaft is oriented and can slide along the alignment axis A for insertion of the acetabular cup 280 according to the preoperatively planned position and orientation. In some embodiments, the acetabular inserter 550 can include an impact head 520 and can be used to impact the acetabular cup 280 after implantation.

Referring to FIGS. 10-13, another method of reaming and preparing the acetabulum 82 is illustrated using the acetabular guides 200 with fitment options 200A and 200B, as described above in connection with FIGS. 4 and 5. In this method, markers pins 260 are inserted through the corresponding bores 252 of the marker elements 250 and attached to the bone in locations and orientations parallel to an axis B, as determined during the preoperative plan. The marker pins 260 can guide the location of a secondary guide 600, shown in FIG. 13, and designed according to the preoperative plan to be guided by the marker pins 260, as discussed below.

The acetabular guide 200 can be slidably lifted off the marker pins 260 and removed, leaving the marker pins 260 attached to the bone. The acetabular cup 280 can be inserted using an acetabular inserter 550 without the aid of an alignment orientation, although a support device 400 with an alignment rod 402 can also be used if desired.

If desired, a reamer 500, 500' with a guiding pin 502 can be used to ream the acetabulum 82, as discussed above in connection with FIG. 7, although other commercially available reamers can also be used. As was described above in connection with FIG. 7 and the acetabular guides 100, a pilot hole 89 of predetermined length is drilled into the acetabulum 82 through the guiding element 204 with a drill element 440 until the stop 442 of the drilling element reaches the upper surface of the guiding element 204 of the acetabular guide 200.

After the acetabular cup 280 is inserted but not impacted, a secondary guide 600 having secondary marker elements 650 with bores 652 complementarily corresponding to the orientation and relative location of the marker elements 250 of the acetabular guide 200 is placed over the marker pins 260. The secondary guide 600 can be designed during the pre-operative plan such that the bores 652 are complementary to the location and orientation of the marker elements 250 of the acetabular guide. The secondary guide 600 can include extender elements 604 supporting an arcuate or crescent-shaped planar flange 602 having parallel inferior and superior surfaces 608, 610 designed during the preoperative plan to be oriented parallel to a rim 282 of the acetabular cup 280, when the acetabular cup 280 is positioned in the predetermined position and orientation. The orientation and position of the acetabular cup 280 is adjusted using the secondary guide 600, such that the planar flange 602 (and the inferior and superior surfaces 608, 610 of the planar flange 602) and the rim 282 are parallel by ascertaining contact and engagement of the planar flange 602 to the rim 282 of the acetabular cup 280 in situ. It is noted that this method does not make use of the support device 400, although the acetabular guides 200 can also be used with the supporting device, at the discretion of the surgeon. Depending on the surgeons preferences, any selected or all the acetabular guides 100 (110A, 100B, 100C) and 200 (200A, 200B) and the associated instruments including the reamer 500, 500', the supporting device 400, the drilling element 440 with the stop 442, alignment rod 402, marker pins 260 and the secondary guide 600 can be provided in a surgical kit together with the acetabular cup 280 and/or additional implants and instruments.

Figure 14:
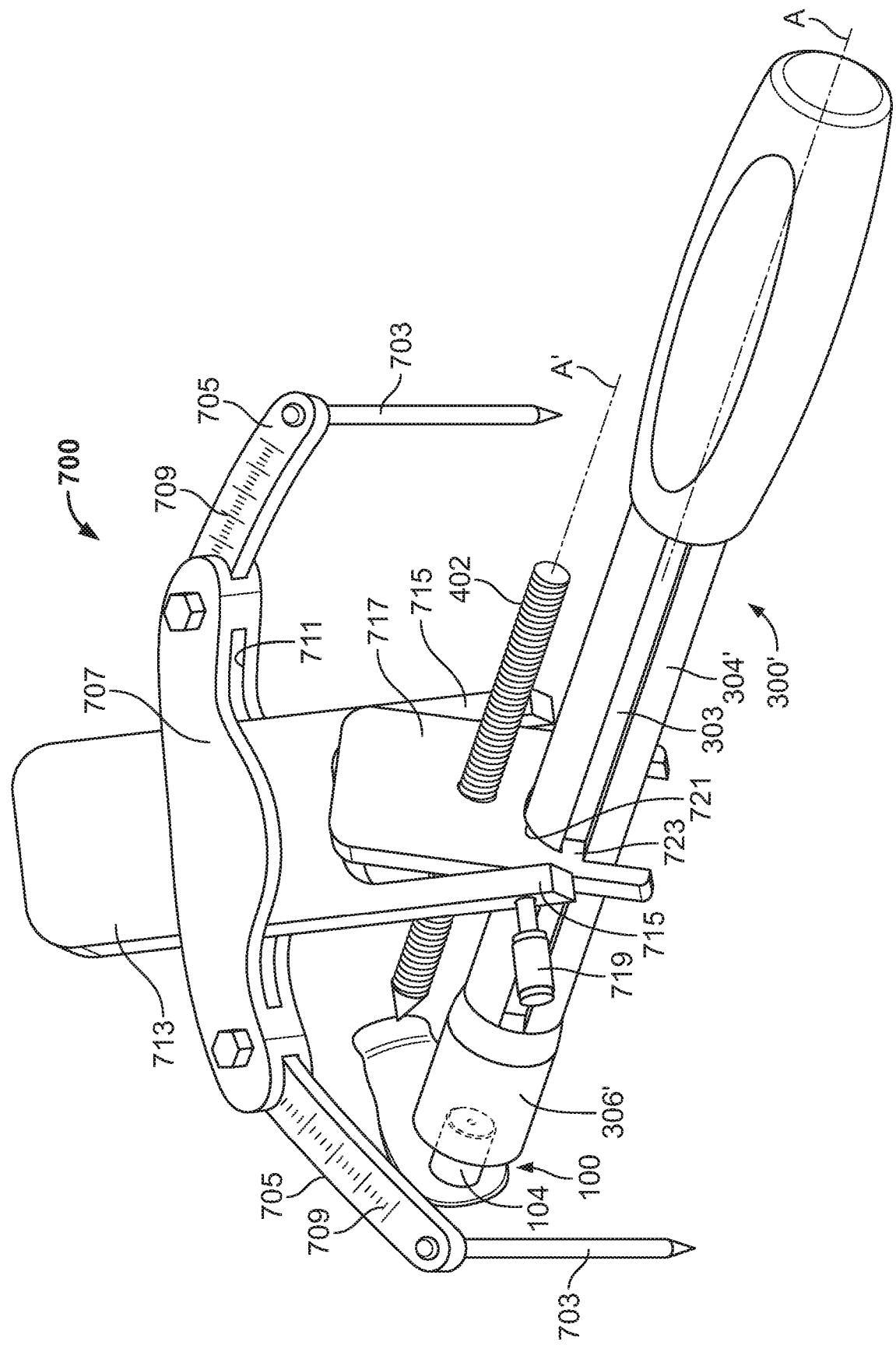
FIG. 14 is an environmental perspective view of a patient-specific acetabular alignment guide with an alignment pin and supporting instruments according to the present teachings.

Referring to FIG. 14, another embodiment of the support device 400 is support device 700 illustrated with a guiding handle 300' and an acetabular guide 100 for positioning an alignment rod 402 in the pre-planned orientation A'. The support device 700 can be attached to the bone with bone pins 703 that pass through arms 705. The arms 705 extend slidably from a body 707 and can include scale markings 709 for measuring distances from the body 707. The body 707 can include a planar slot 711 through which a first planar flange 713 can slidably pass there through and locked with a fastener (not shown) after adjustment. The first planar flange 713 includes arms 715 pivotably connected to a second planar flange 717 along a pivot axis coinciding with a center axis of a locking element 719. The locking element 719 can be used to lock the relative orientations of the first and second planar flanges 713, 717. The second planar flange 717 can have a curved engagement surface 721 for slidably engaging a shaft 304' of the guiding handle 300'. The shaft 404' can include a groove 303 that is rotationally keyed to an element 721 extending from the second planar flange 717. The support device 700 can provide pivotable and translational adjustability to align the alignment rod 402 parallel to the alignment axis A which is fixed when the shaft 304' is attached to the guiding element 104 of the acetabular guide. The support device 700 can be used generally similarly to the support device 400 to provide a reference axis A' along the reference or alignment rod 402 to guide a reamer 500 or implant inserter 550.

Figure 15:
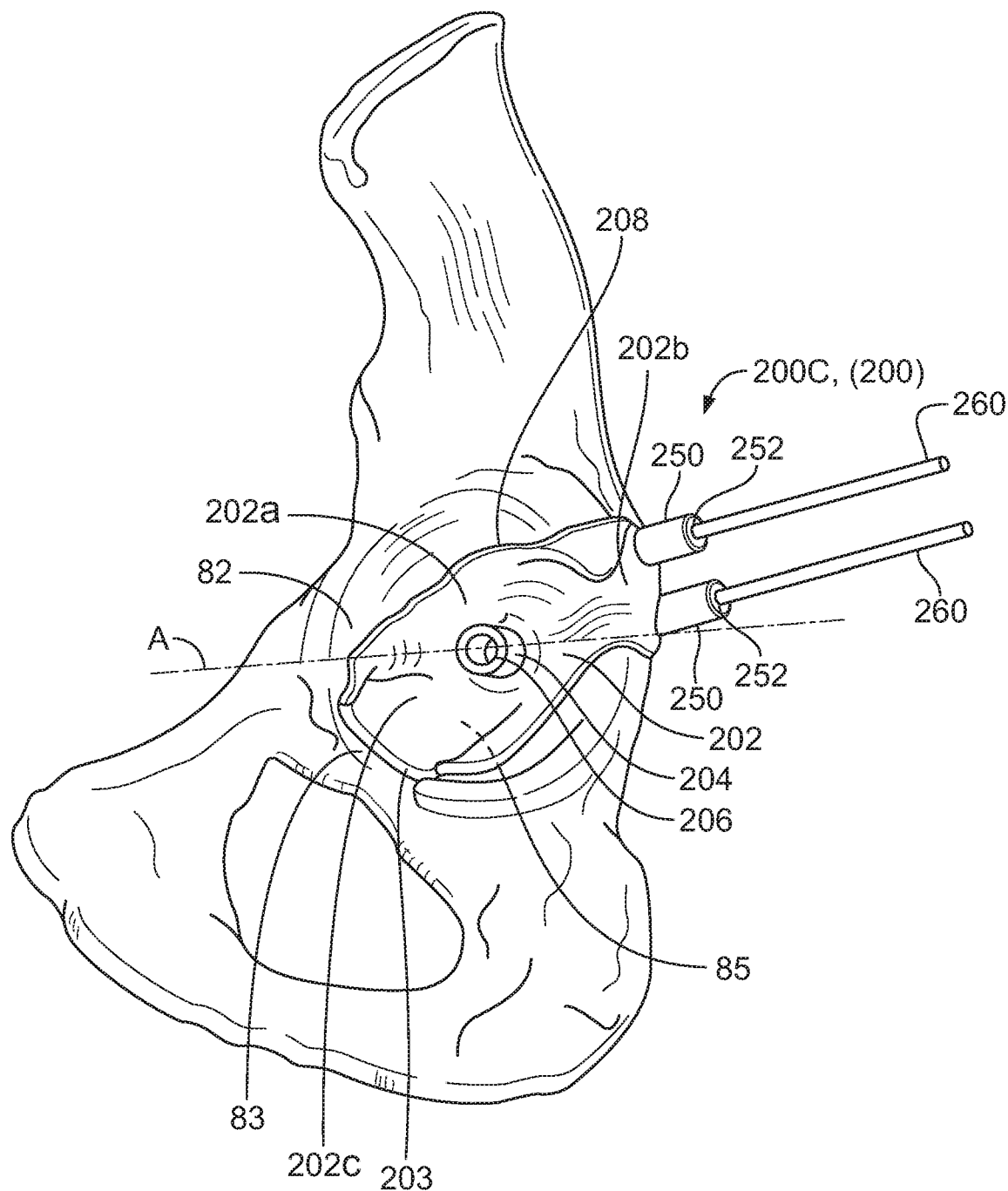
FIG. 15 is an environmental view of another embodiment of a patient-specific acetabular alignment guide shown with marker pins according to the present teachings.

Referring to FIG. 15, another embodiment 200C of a patient-specific acetabular guide 200 is illustrated. Similarly to the embodiments illustrated in FIGS. 4 and 5 discussed above, the acetabular guide 200C includes a patient-specific body 202 and a guiding or pilot element 204 having an elongated bore 206 with an alignment axis A configured to be central to the acetabular cup and perpendicular to the acetabular cup's surface when the acetabular guide 200 is positioned on the acetabulum 82. The acetabular guide 200 can include one or more marker elements 250 (two are shown), each having an elongated bore 252 for guiding corresponding marker pins 260. The marker pins 260 can be used for supporting a secondary guide such as discussed below in reference to FIG. 12 above, or a secondary guide shown in FIG. 16.

The patient specific body 202 of acetabular guide 200C is similar to the body 202 of the acetabular guide 200A or 200B of FIGS. 4 and 5, and includes a first portion 202a from which the guiding element extends and which is designed to engage the acetabulum 82, and a second portion 202b which extends from the inner portion 202a and is configured to extend over a rim portion 84 of the acetabulum 82. The outer portion 202b extends sufficiently beyond the rim 84 to the periacetabular area of pelvis to accommodate the marker elements 250. The patient specific body 202 has an underside or bone-engaging three-dimensional engagement surface 208 that is custom-made or patient-specific to conform to and mirror (as a negative or inverse or mirror surface) complementary surfaces of selected portions of the acetabulum 82. In the embodiment of FIG. 15, the patient specific body 202 includes additionally a third portion 202c which conforms to and covers at least a portion of the acetabular fossa 85 of the acetabulum for providing additional rotational stability. Further, an inferior edge 203 of the acetabular guide 200C on the third portion 202c is designed during the preoperative plan to be parallel to the shape of the transverse acetabular ligament 83. The inferior edge 203 can provide an additional visual confirmation of correct alignment during positioning of the acetabular guide 200C on the acetabulum 82 of the patient.

Figure 16:
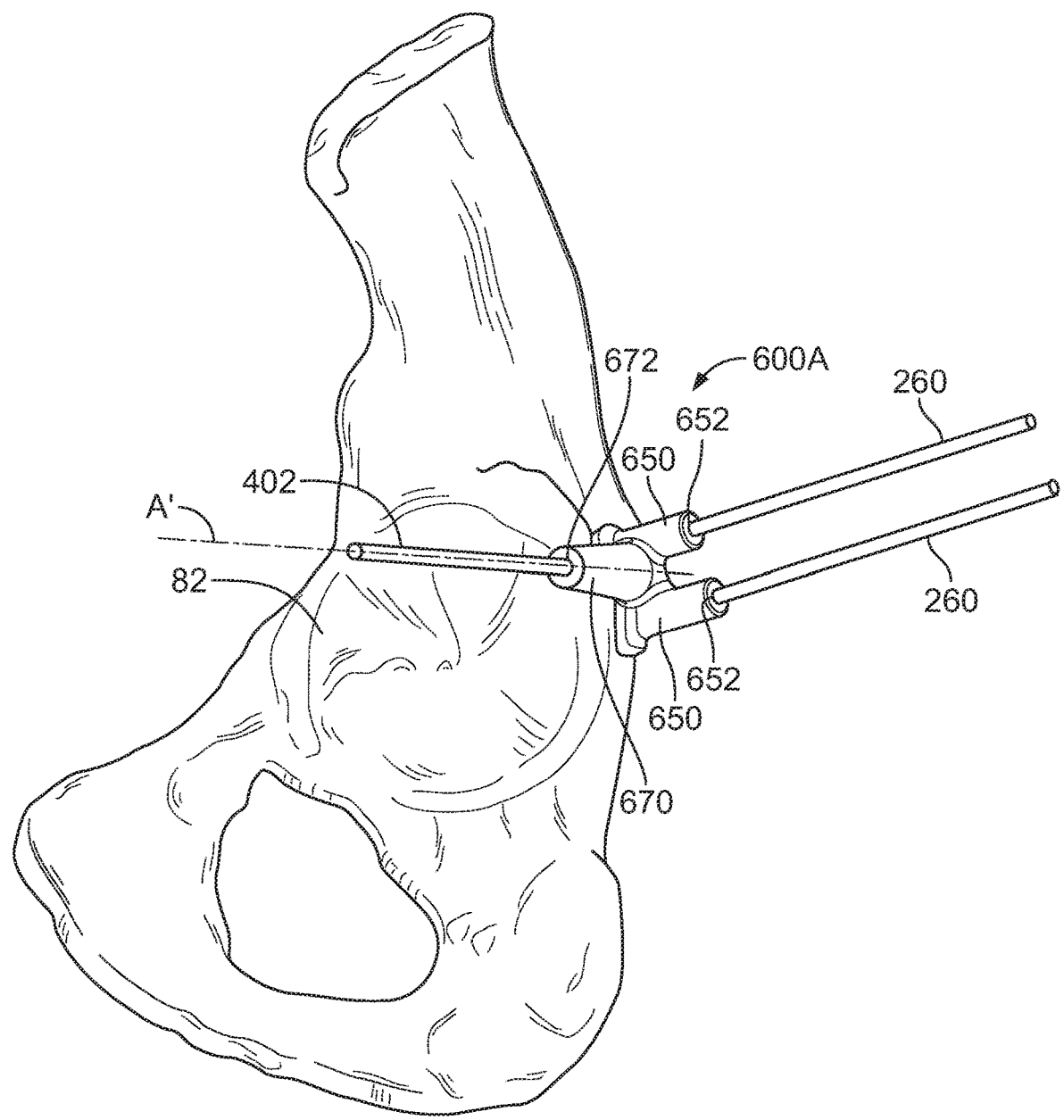
FIG. 16 is an environmental view of another embodiment of a secondary guide shown with marker pins according to the present teachings.

Referring to FIG. 16, another embodiment of a secondary guide 600A is illustrated. The secondary guide 600A can be used with any of the acetabular guides 200 (200A, 200B, 200C). The secondary guide 600A can have first and second (secondary) marker elements 650 with bores 652. The secondary guide 600 can be designed during the pre-operative plan such that the bores 652 are complementary to the location and orientation of the marker elements 250 of the acetabular guide. The marker pins 260 are secured into the bone through the marker elements 250 of the acetabular guide 200, as shown, for example, in FIG. 10, and discussed above. The acetabular guide 200 is then lifted off the marker pins 260 and the secondary guide 600A is guided and placed over the marker pins 260. The secondary guide 600A is also designed during the preoperative plan for the patient to have a guiding element 670 with a longitudinal bore 672 along an axis A' that is parallel to the alignment axis A for the acetabular implant, when the secondary guide 600A is seated on the acetabulum over the marker pins 260, as shown in FIG. 16. Accordingly, an alignment pin 402 inserted into the bore 672 can serve as an indicator of the alignment direction A for reaming the acetabulum and inserting the acetabular cup.

As discussed above, the alignment axis A is the pre-operatively planned axis for insertion of the acetabular cup 280. Although the alignment axis A is shown, for simplicity, to coincide with the center axis of various instruments used for inserting, reaming and impacting the acetabular cup 280, it should be appreciated that this designation is adapted to indicate the final positioning of the instrument in the desired alignment. In other words, the alignment axis A and the axis of the instrument used are brought to coincidence by the methods described herein and according to the present teachings.

Figure 17:
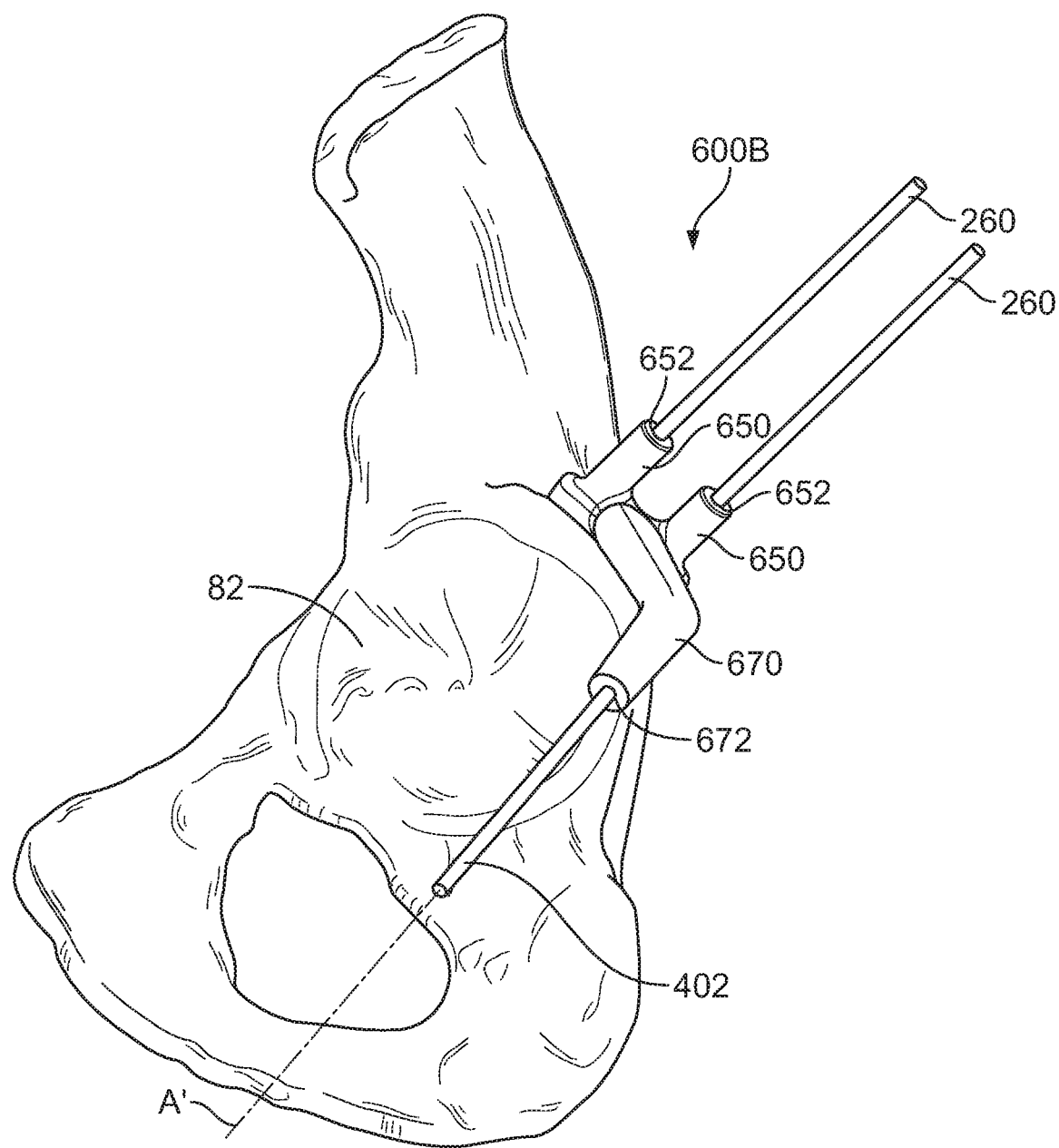
FIG. 17 is an environmental view of another embodiment of a secondary guide shown with marker pins according to the present teachings.
Figure 18:
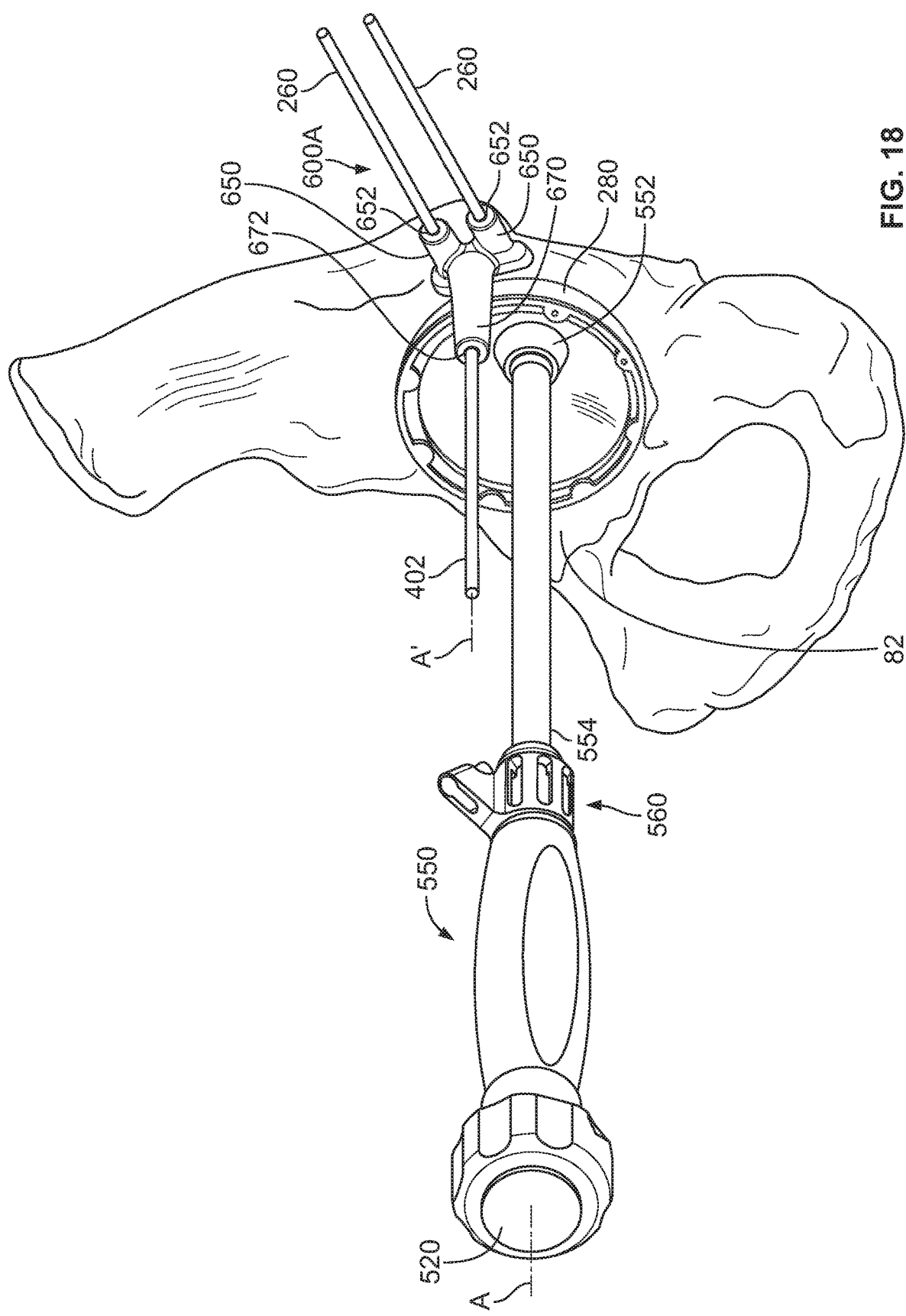
FIG. 18 is an environmental view illustrating a method of inserting an acetabular cup using the secondary guide of FIG. 16 according to the present teachings.
Figure 19:
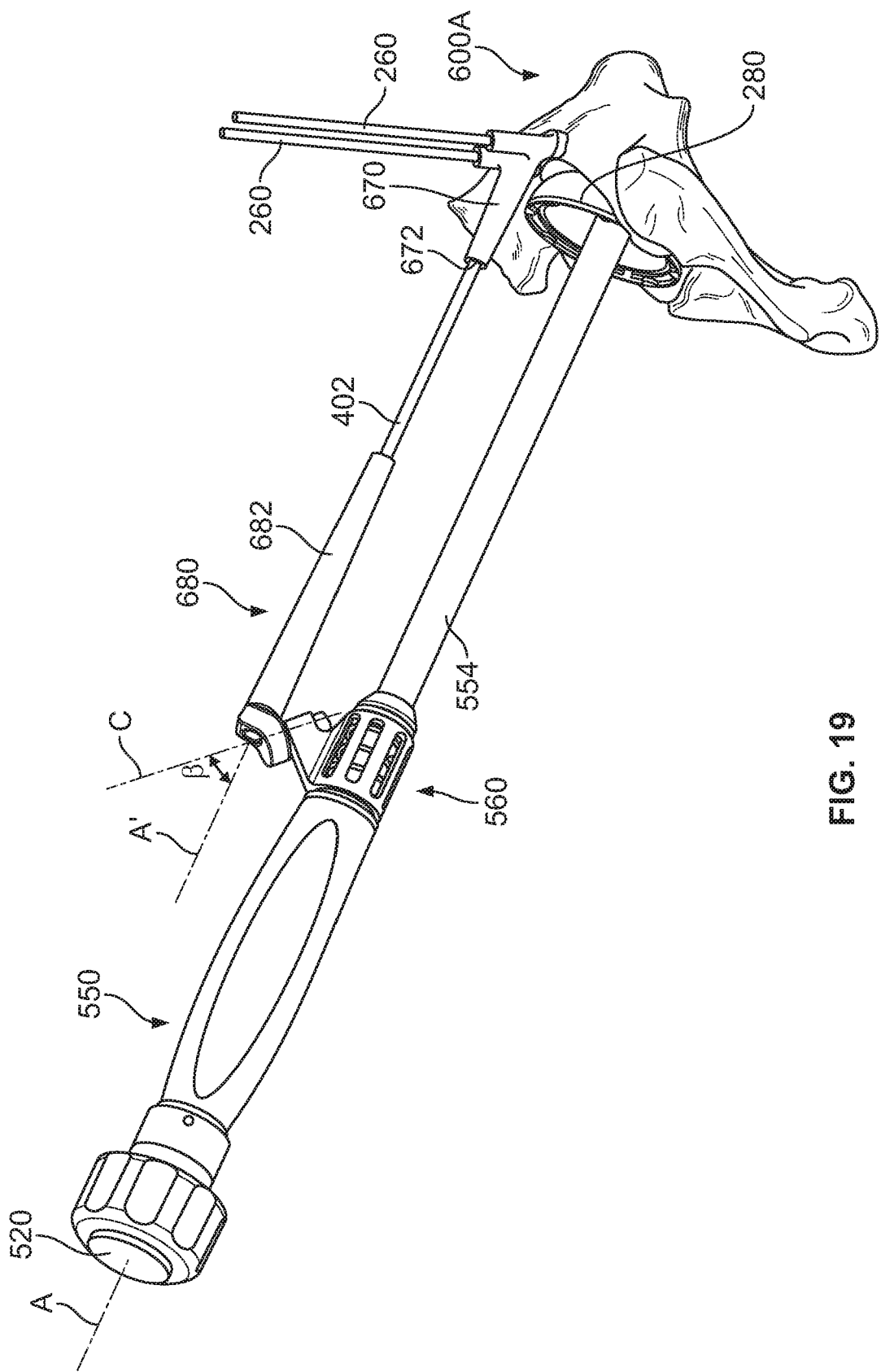
FIG. 19 is an environmental view illustrating another method of inserting an acetabular cup using an acetabular inserter coupled to the secondary guide of FIG. 16 with an adaptor according to the present teachings.

In some embodiments of the secondary guide, such as the secondary guide 600B shown in FIG. 17, the guiding element 670 may be placed in an offset position relative to the secondary marker elements 650 to provide better visualization of the acetabulum while guiding a reamer, inserter, impactor or other instrument along the alignment axis A parallel to the alignment pin 402.

Figure 20:
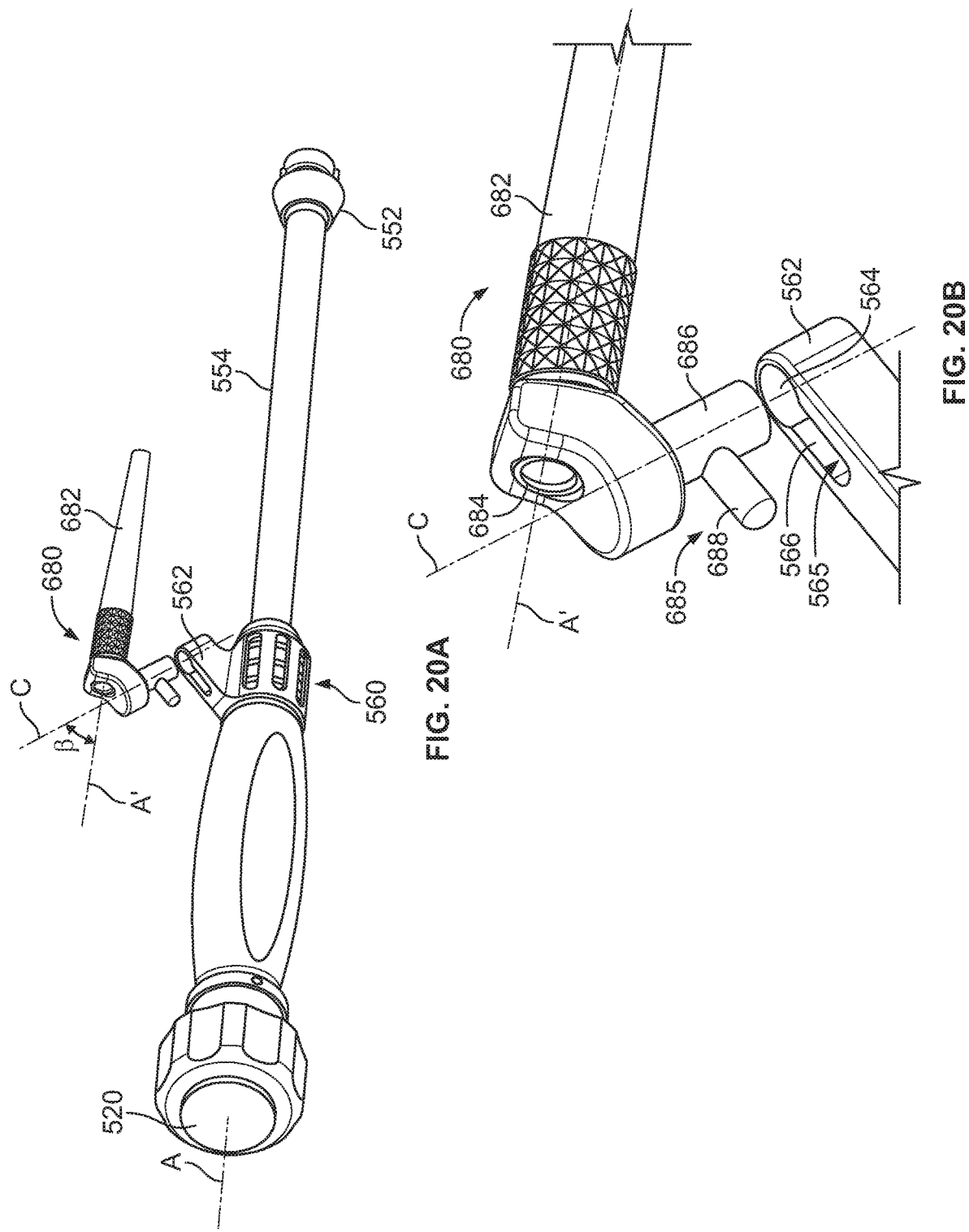
FIGS. 20A and 20B are perspective views of a detail of coupling between the acetabular inserter and the adaptor of FIG. 19.

Referring to FIGS. 18-20B, the acetabular inserter 550 coupled to the acetabular cup 280 can be guided along the alignment axis A by the alignment pin 402 of the secondary guide 600A (or the offset secondary guide 600B), as an alternate method that does not use the support device 400 described above and shown in FIG. 9. In some embodiments, an adaptor 680, shown in FIGS. 19-20B, can be optionally used to couple the acetabular inserter 550 to the alignment pin 402 of the secondary guide 600A, as a further aid to orient the acetabular inserter 550 along the alignment axis A. In particular, the adaptor 680 includes an arm 682, such as a cannulated shaft having a longitudinal bore 684 that receives the alignment pin 402 when the adaptor 680 is placed over the alignment pin 402. Accordingly, the shaft 682 is aligned along the axis A' that is defined by the guiding element 670 of the secondary guide 600A. The adaptor is coupled to a rotatable collar 560 of the acetabular inserter 550 and secures the acetabular inserter 550 along the alignment axis A parallel to the axis A' of the shaft 682 and alignment pin 402. The adaptor 680 can be coupled to the collar 560 with a tongue-in-groove or other keyed connection, as illustrated in FIGS. 20A and 20B. In some embodiments, for example, the collar 560 can include an extension 562 forming a keyhole-shaped opening 565 with a first portion 564 having a circular cross-section and a second portion 566 having an elongated cross-section. The keyhole opening 565 receives correspondingly shaped portions of the adaptor 680, forming a key 685 for the keyhole opening 565 and preventing rotational movement. The key 685 has a first cylindrical element 686 received in the first portion 564 of the opening 565 and a second element 688 extending at a right angle from the first element 686 and received into the second portion 566 of the keyhole opening 565. Additionally, the key 685 and the keyhole opening 565 are angled at an acute angle relative to the alignment axis A and axis A'. Specifically, the first portion 564 of the keyhole opening 565 and the first element 686 of the key 685 are oriented along the direction of an axis C forming an acute angle β with axes A and A' as shown in FIGS. 20A and 20B. This skewed orientation facilitates the insertion of the key 685 into the keyhole opening 565 and the coupling of the adaptor 680 to the acetabular inserter 550.

Figure 21:
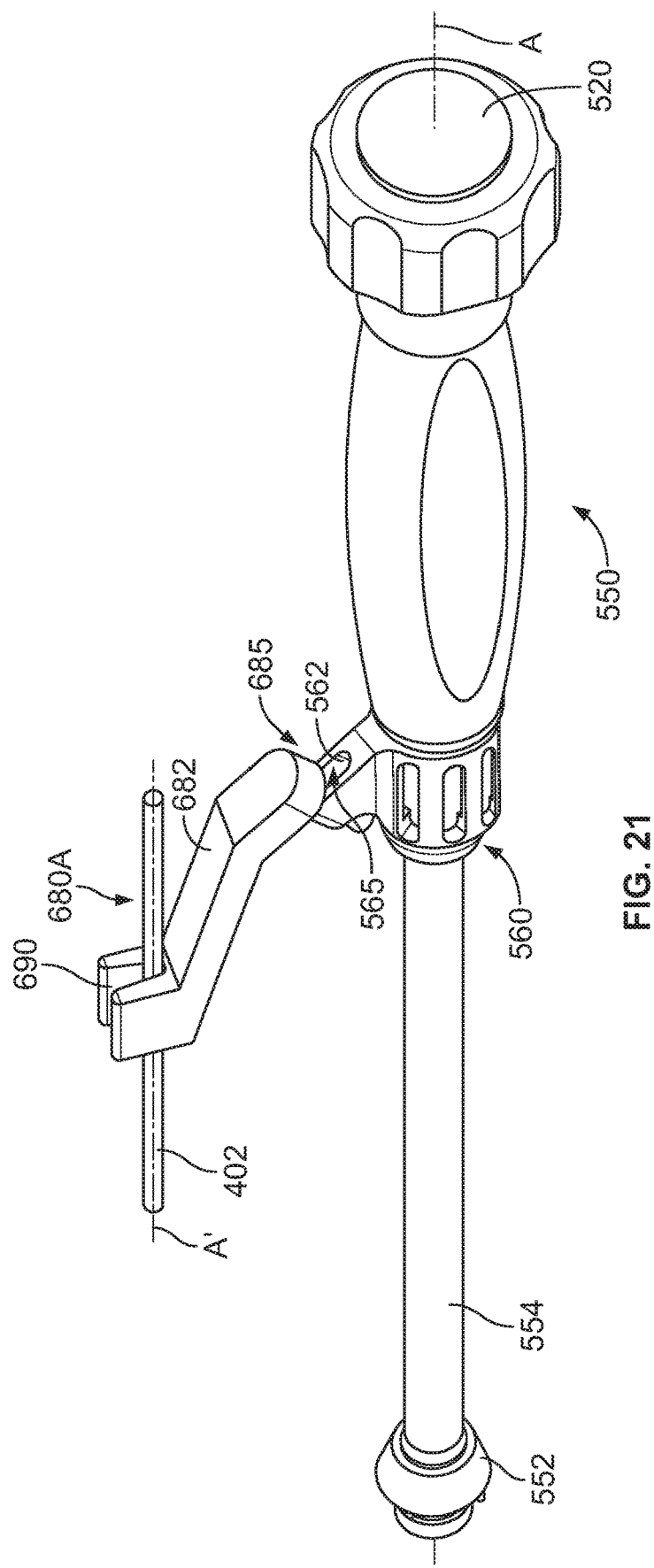
FIG. 21 is a perspective view of another embodiment of an adaptor for coupling an acetabular inserter to a secondary guide according to the present teachings.

Referring to FIG. 21, in some embodiments 680A, the arm of 682 of the adaptor 680A can include an external V-shaped notch 690 instead of an internal cannulation 684 of the embodiment 680 of FIGS. 20A and 20B, while retaining the key 685 for engagement with the keyhole opening 565 of the acetabular inserter 550. The notch 690 can receive the alignment pin 402 in a semi-constrained arrangement for facilitating engagement and disengagement between the adaptor 680A and the alignment pin 402.

Figure 26:
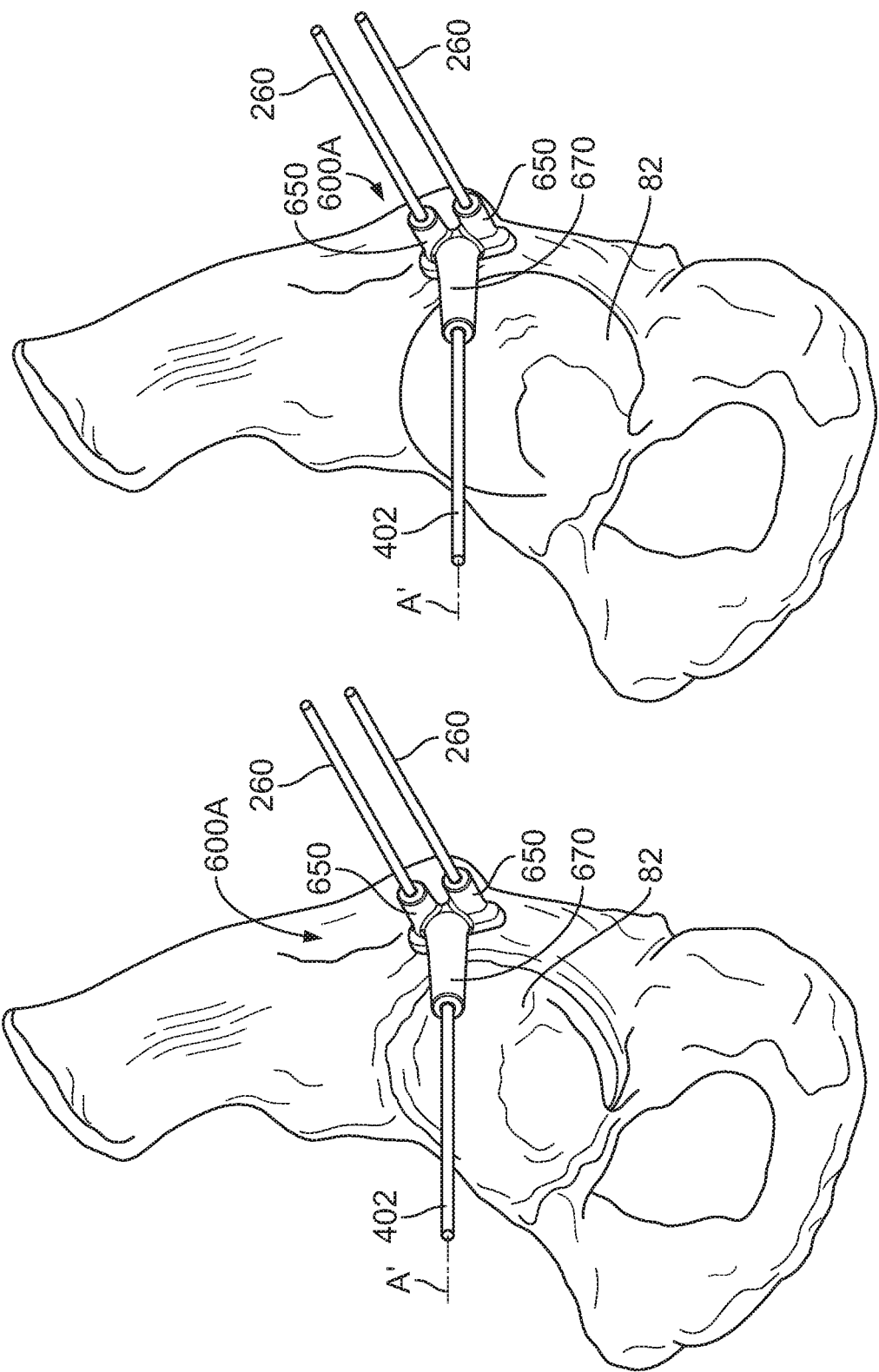
FIGS. 26A and 26B illustrate an acetabulum before and after reaming, respectively, using a secondary guide for alignment during reaming according to the present teachings.
Figure 27:
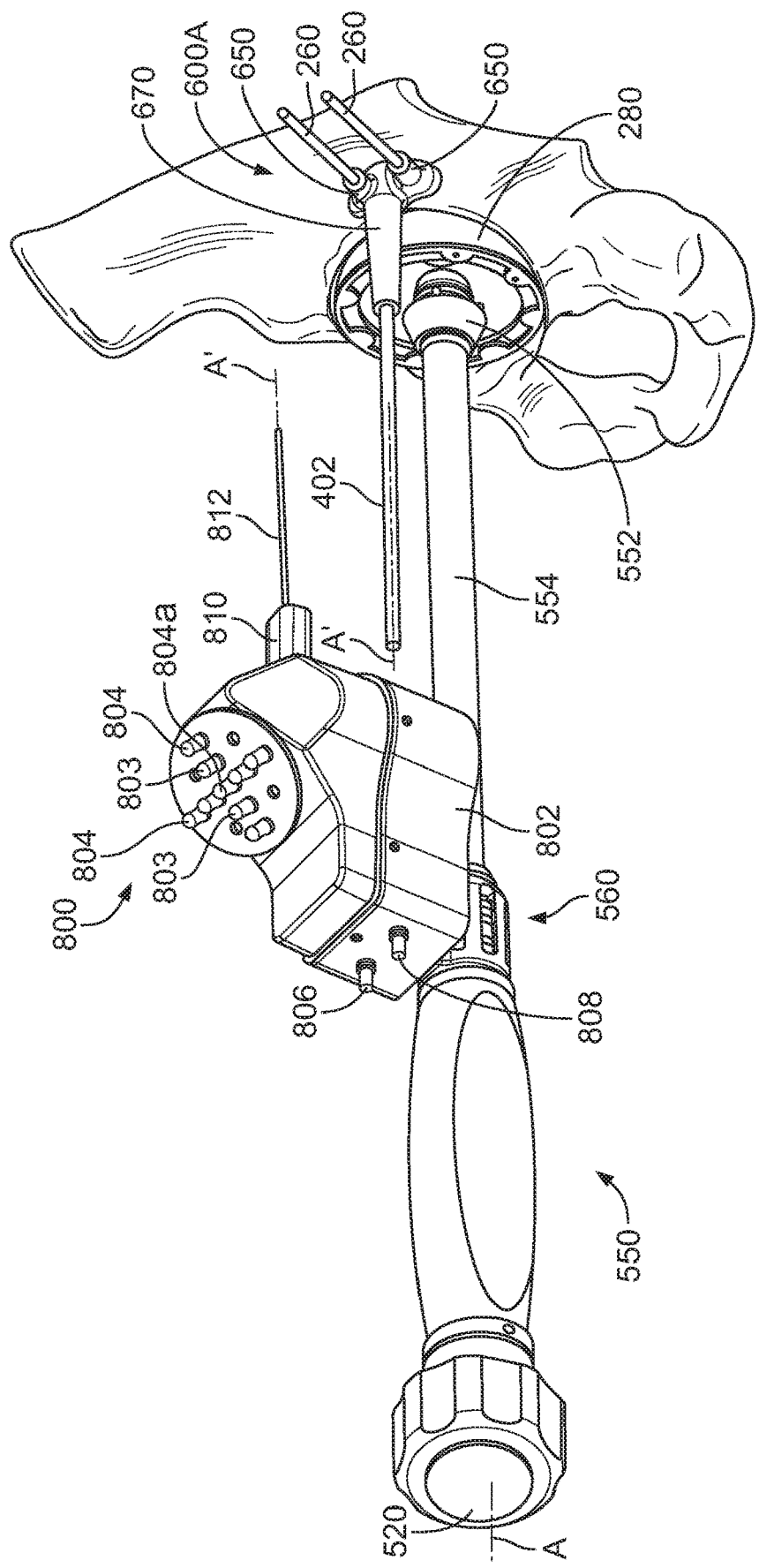
FIG. 27 is an environmental perspective view illustrating inserting an acetabular cup using the calibrated positioner and secondary guide of FIG. 25 according to the present teachings.
Figure 28:
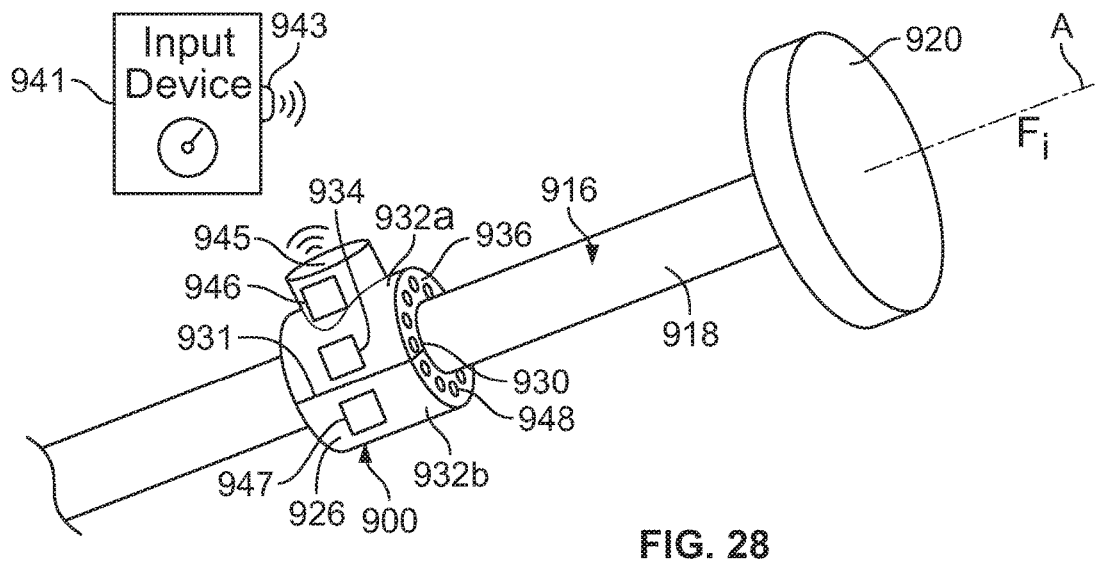
FIG. 28 is a perspective view of an electronic positioner coupled to an acetabular inserter/impactor as disclosed in commonly assigned U.S. Patent Publication 2010/0249796.
Figure 29:
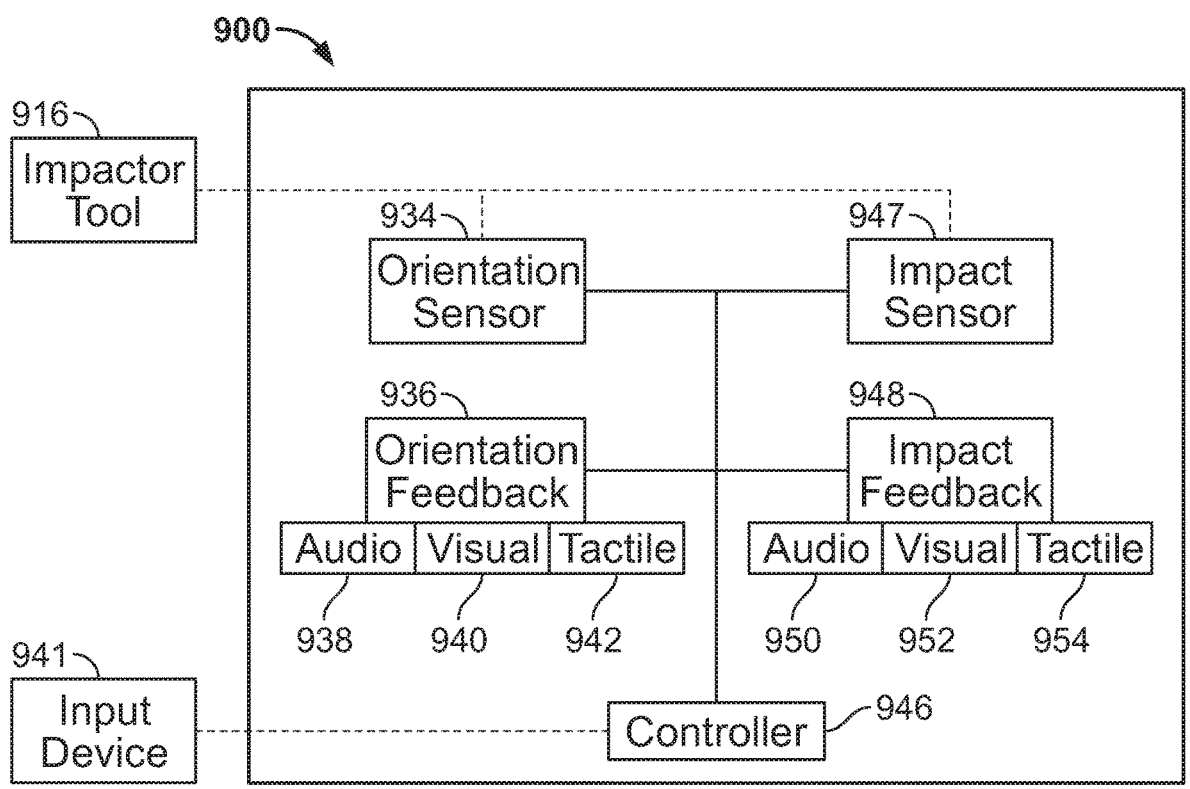
FIG. 29 is a schematic view of the electronic positioner of FIG. 28.

Referring to FIGS. 22-29, various methods for preparing the acetabulum for receiving an implant will be discussed in connection with the use of electronic positioners (800, 900) or other orientation devices for guiding the surgeon along the alignment axis A during reaming and/or inserting and impacting the acetabular implant into the acetabulum. Any commercially available orientation sensing devices can be used for the electronic positioner 800 (FIG. 22) or electronic positioner 900 (FIGS. 28 and 29). Various embodiments of the electronic positioner 900 are described in commonly assigned patent publications 2010/0249657, and 2010/0249796, both published on Sep. 30, 2010, and incorporated herein by reference. The electronic positioners can include a number of gyroscopic sensors and/or accelerometers that can measure deviations from a predetermined orientation and maintain or guide a return to that orientation. In the context of the present teachings, the predetermined orientation is the alignment axis A that was discussed above. Further, digital or MEMS gyroscopes of small size and capable of measuring deviation about two or three sin axes can be used, such as, for example, a three-axis, single sensor digital gyroscope (model L3G4200D) available from STMicroelectronics, Carrollton, Tex. It should be appreciated, however, that any combination of orientation sensors capable of identifying an orientation in three-dimensional space, including combinations of gyroscopic sensors (digital, analog, fiber optic or other type), having one or more axes, with other orientation sensors, such as accelerometers, such that the combination can identify deviations from an axis in three-dimensional space. For example, a 3-axis gyroscope (yaw, roll and pitch), or three one-axis gyroscopes, or one 2-axis gyroscope and one accelerometers, or three accelerometers or other combinations of gyroscopes and accelerometers. In some embodiments, the accelerometers can be single or multiple axes accelerometers. Mechanical, piezoelectric, MEMS, analog or digital accelerometers and gyroscope can be used. Additionally, a miniaturized compass, a laser, and/or GPS device may be included with the electronic positioner.

Figure 22:
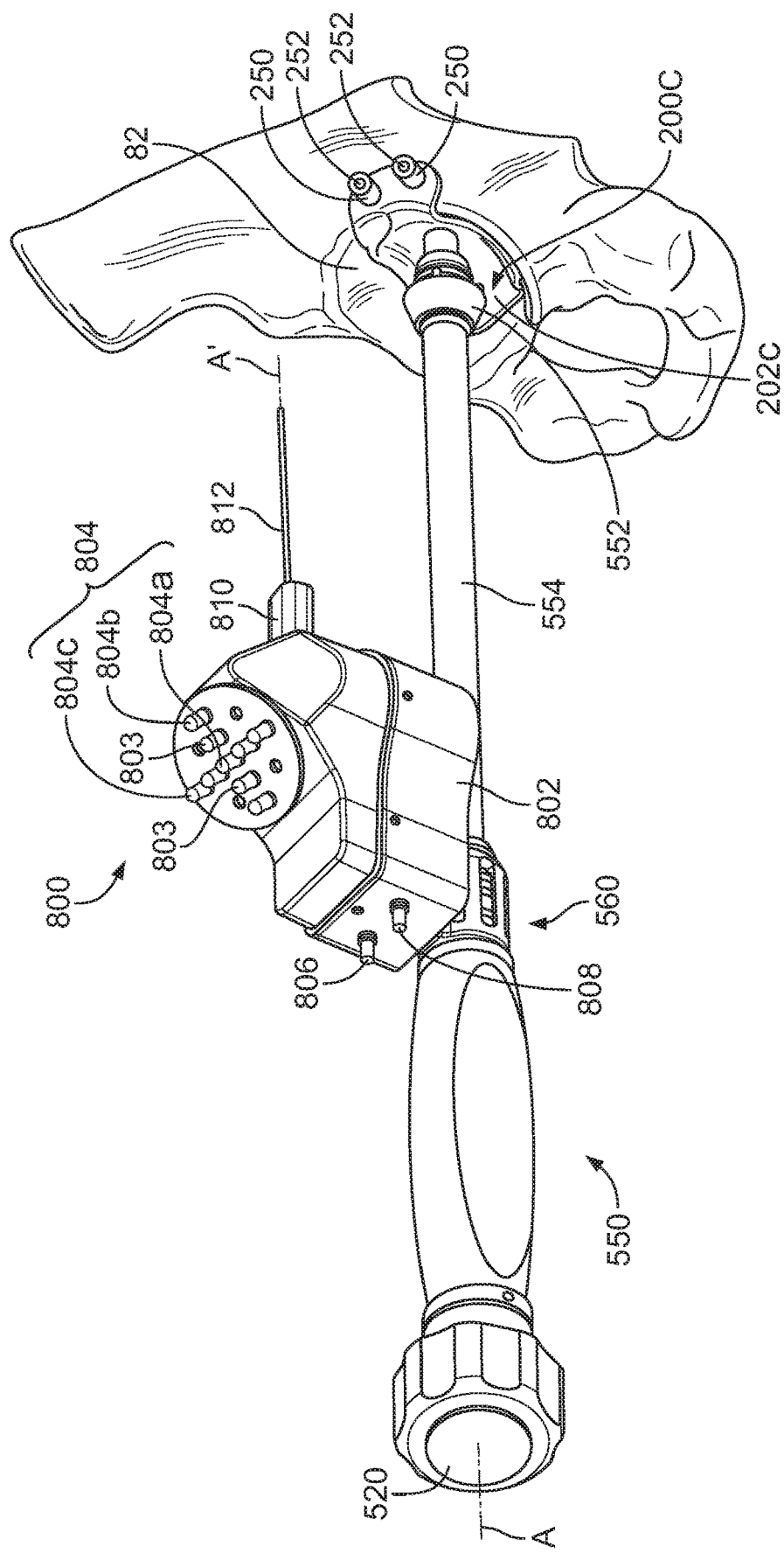
FIG. 22 is an environmental perspective view illustrating calibrating an electronic positioner coupled to an acetabular inserter and using a patient-specific alignment guide without marker pins according to the present teachings.

Referring to FIG. 22, the electronic positioner 800 can include a housing 802 that is removably attachable to a shaft of an inserter, impactor, reamer or other instrument used in connection with the acetabular arthroplasty or other corrective procedure. In FIG. 22, the electronic positioner is shown coupled to the acetabular inserter 550. The electronic positioner 800 can be, for example, keyed to the shaft 554, slidably attached to the shaft 554 or the collar 560 of the acetabular inserter 800 or slip-fit or with a clamp-on or tongue-and-groove or other coupling arrangement. The housing 802 can include a controller/processor communicably coupled to the orientation sensor/sensors discussed above, and a feedback module. An exemplary block diagram for the electronic positioner 900 of FIG. 20 is shown in FIG. 29, described below, and can be used for the electronic positioner 800, although the impact sensor and associated modules are optional and can be omitted from the electronic positioner of 800.

The electronic positioner 800 can include a power or on/off button 806, a set button/input device 808 for setting a pre-determined orientation during calibration and a set of LEDs 804 (outer set 804) for guiding the shaft 554 along the predetermined orientation (i.e., the alignment axis A) by lighting up to indicate a direction. The electronic positioner 800 can also include an optional laser device 810 capable of providing a reference orientation 812. The laser device 810 may be used, for example, with accelerometers that measure in two non parallel directions in a plane perpendicular to the reference orientation 812 of the laser. The electronic positioner 800 can be calibrated using one of the patient-specific acetabular guides described above, such as, for example, the acetabular guide 200C, shown in FIG. 22. The acetabular guide 200C can be positioned at a unique position on the patient's acetabulum, such that the guiding element 204 defines the alignment axis A, as designed during the preoperative plan. The shaft 554 of the acetabular inserter 550 can be slidably coupled to the guiding element 204 as described above in reference to FIG. 6, for example, such that the longitudinal axis of the shaft 554 coincides with the alignment axis A.

With the shaft 554 of the inserter 550 aligned along the alignment axis A, and the electronic positioner 800 coupled thereon, the set button/input device 808 can be pressed or otherwise activated to set or identify the alignment axis A as a reference axis, and store its orientation. As the shaft 554 is moved, deviations from the reference axis can be calculated by the sensors (see 934, FIG. 29) of the electronic positioner, processed by the controller (see 946, FIG. 29) of the electronic positioner and feedback provided by the LEDs 804 indicating the direction and increment of deviation. For example, the direction of deviation or, alternatively the direction to move to correct the deviation, can be indicated by the direction defined by a lit LED, such as, for example, 804b relative to a central LED 804a, which lights up when the shaft 554 is correctly aligned along the reference/alignment axis A. In some embodiments, a relative amount or degree of deviation for a given direction of a deviation can be indicated by a change in color of the LEDs 804, or by another set of LEDs 803 (inner set) that light up at a different fixed color, for example a fixed yellow to a fixed red of the outer set of LEDS 804. It will be appreciated that other types of feedback mechanisms or arrangements with or without LEDS and including visual, audio and vibratory or tactile feedback can be used, as disclosed in patent publications 2010/0249657 and 2010/0249796, referenced above, and further discussed below in reference to FIGS. 28 and 29.

Figure 23B:
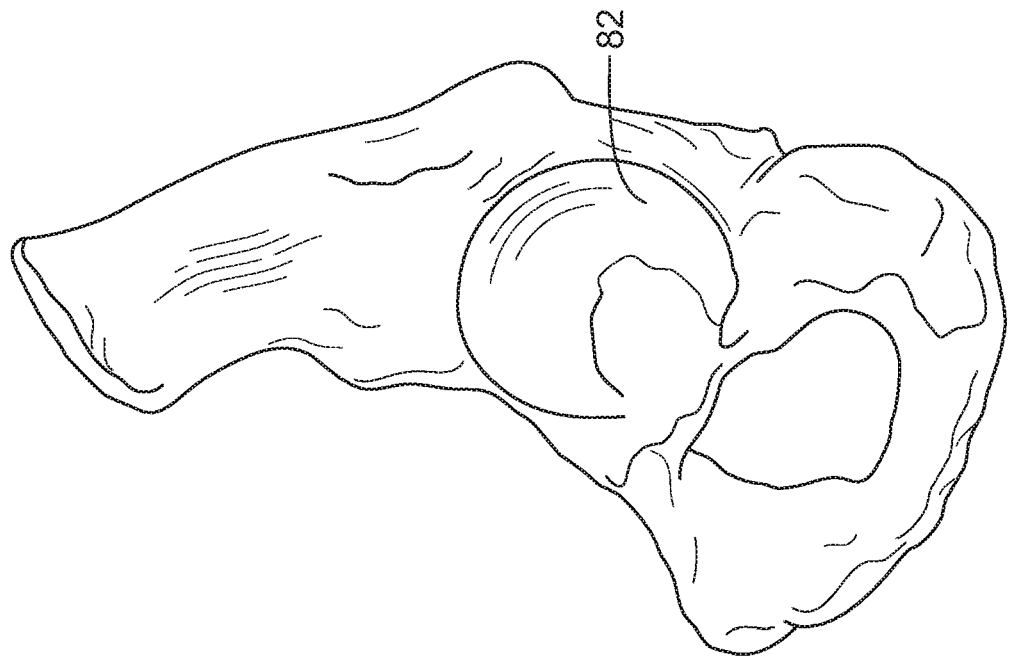
FIGS. 23A and 23B illustrate an acetabulum before and after reaming, respectively.
Figure 23A:
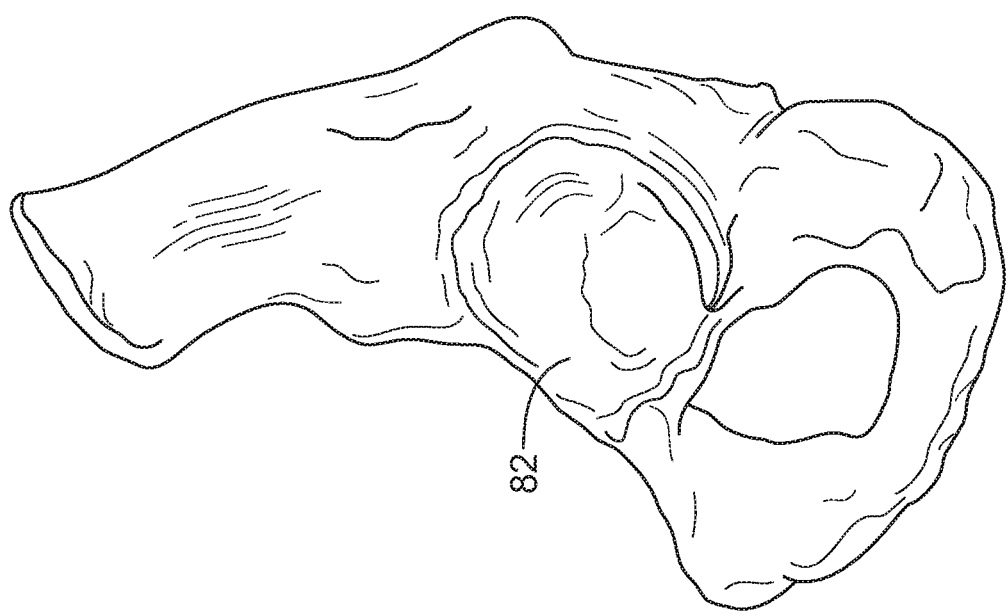
Figure 24:
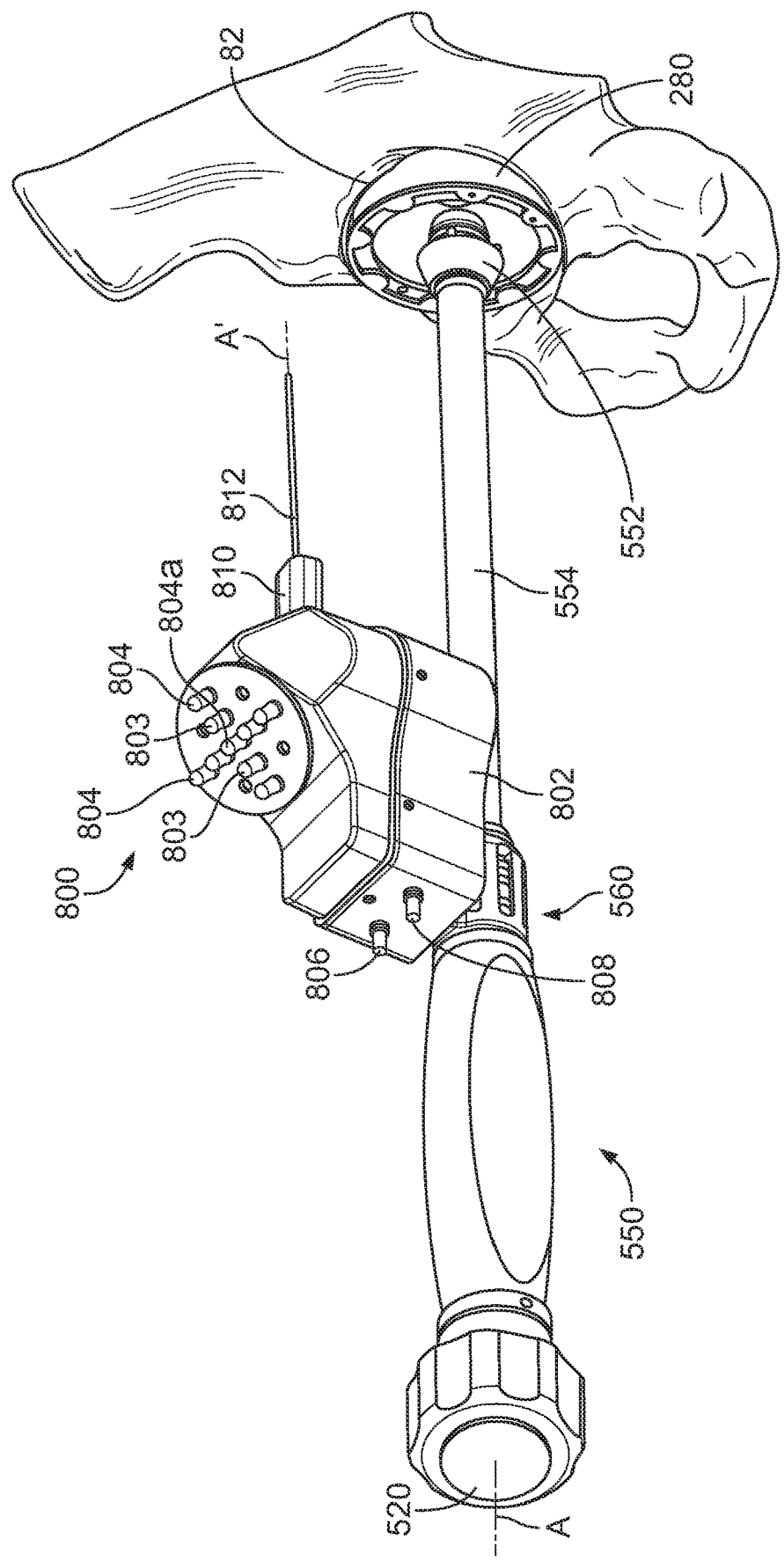
FIG. 24 is an environmental perspective view illustrating inserting an acetabular cup using the calibrated positioner of FIG. 22 according to the present teachings.

After the electronic positioner 800 is calibrated, the surgeon may ream the acetabulum 82 using a surgeon-selected method or any of the methods discussed above. See, for example, FIG. 8A and associated discussion. FIGS. 23A and 23B illustrate the patient's acetabulum 82 before and after reaming, respectively. After reaming, the acetabular inserter 500 with the electronic positioner 800 thereon can be coupled to the acetabular implant 280, as shown in FIG. 24, for inserting the acetabular implant 280 along the predetermined alignment axis A, as guided by the electronic positioner 800. Feedback from the LEDs 804 and/or 803 or other feedback mechanism can help guide the surgeon to correct any deviation from the predetermined alignment axis A that coincides with the calibrated reference axis of the electronic positioner 800, as discussed above.

Figure 25:
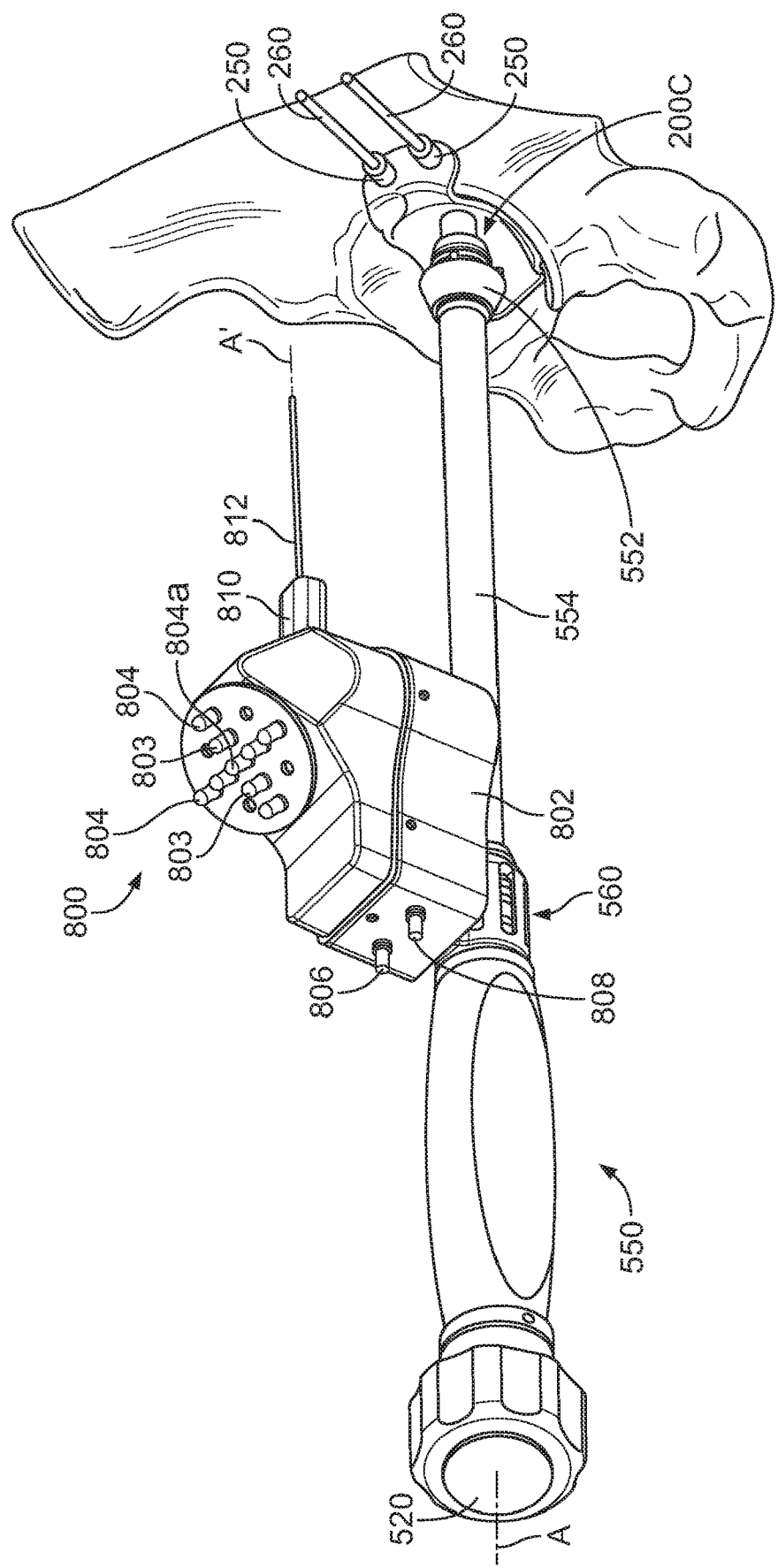
FIG. 25 is an environmental perspective view illustrating calibrating an electronic positioner coupled to an acetabular inserter and using a patient-specific alignment guide with marker pins according to the present teachings.

When using the electronic positioner 800, as described above, marker pins 260 and a secondary guide 600, 600A, 600B are not necessary. Depending on the surgeon's preference, when additional guidance is desired, the marker pins 260 and the secondary guide 600A (or 600 or 600B) can be used together with the electronic positioner 800, as illustrated in FIGS. 25-27. The marker pins 260 can be inserted, for example, through the marker elements 250 of the patient-specific acetabular guide 200C, as shown in FIG. 25 during calibration of the electronic positioner 800. After calibration, the patient-specific acetabular guide 200C is lifted off the marker pins 260, which are left attached to the acetabulum 82 for guiding the placement of the secondary guide 600A (or 600B or 600), as shown in FIG. 26A. The alignment pin 402 can be used as a reference for the implant alignment axis A. In some embodiments, the alignment pin 402 can be used to align a supporting shaft 506 of a reamer 500 (see FIG. 8A) parallel to the direction A' of the alignment pin 402 and used during reaming. After reaming, the secondary guide 600A and the marker pins 260 can remain attached to the acetabulum, as shown in FIG. 26B, to further guide the surgeon during the insertion of the acetabular cup 280. Accordingly, and referring to FIG. 27, the alignment pin 402 of the secondary guide 600A can provide an initial reference direction A' for the surgeon to position the acetabular inserter 800 easier and quicker along the alignment direction A, and make smaller corrections in orientation with the help of the LEDs 804, 803 or other feedback mechanism of the electronic positioner 800.

Referring to FIGS. 28 and 29, the electronic positioner 900 of the above referenced patent publications 2010/0249657 and 2010/0249796 is briefly described. It will be appreciated that in some embodiments, the electronic positioner 900 can replace the electronic positioner 800 in the methods described above. In other embodiments, the electronic positioner 800 can incorporate all or some of the functions of the electronic positioner 900, while maintaining, for example, the geometry of the housing 802 and the LED feedback arrangement described above in reference to FIG. 22. In some embodiments, the electronic positioner 800 can include a orientation sensor (or sensors) 934, but not impact sensors 947 and impact feedback, as discussed below. In other embodiments, the electronic positioner 800 may also include the impact sensor 947 and associated feedback mechanisms of the electronic positioner 900.

As shown in FIGS. 28 and 29, the electronic positioner 900 can include a cylindrical housing 926 coupled to an acetabular inserter/impactor tool 916 having a longitudinal shaft 918. Specifically, the housing 926 can include a passage 930 that receives the shaft 918 and couples the housing 926 to the acetabular inserter/impactor tool 916 in a fixed position relative to the shaft 918. The housing 926 can include a seam or hinge or other longitudinal separator 931 between first and seconds portions 932a, 932b of the housing 926 for removing the housing 926 from the shaft 918. In some embodiments, the hinge 931 can operate to secure the first and second portions 932a, 932b in a clam shell design of the housing 926.

It will be appreciated that the housing 926 can be attached to the shaft 918 in any suitable fashion, such as an interference fit, a taper to taper fit between the shaft 918 and the inner surface of the passage 930, or other arrangement. In some embodiments, the shaft 918 can include a recess (not shown) that receives the housing 926 such that the housing 926 is in a fixed position relative to the shaft 918. Further, the electronic positioner 900 can be removably coupled to various commercially available inserter/impactor tools 916, such as a RingLoc® Inserter (Part No. S313141) or a Magnum Inserter (Part No. 313131), commercially available from Biomet Manufacturing Corp., of Warsaw, Ind. The electronic positioner 900 can be similarly coupled to the shaft of the inserter 550 or reamer 500 or guiding handle 300 or other tool used during the acetabular procedure for guiding along the alignment axis A.

As shown in FIGS. 28 and 29, the electronic positioner 900 can include one or more orientation sensors 934. The orientation sensor 934 can detect an actual orientation of the longitudinal axis of the inserter/impactor tool 916 relative to a reference orientation or reference vector, such as the force of gravity. In some embodiments, the orientation sensor 934 can detect acceleration about three separate orthogonal axes (accelerometer sensors) or angular velocity (spin) about one or more orthogonal axes (gyroscopic sensor), as discussed above in reference to the electronic positioner 800.

The electronic positioner 900 (or 800) can include an orientation feedback device 936. The orientation feedback device 936 can selectively provide an orientation feedback signal when the actual orientation of the inserter/impactor tool 916 is substantially equal to a predetermined target orientation, i.e., the alignment axis A discussed above. The feedback signal provided by the orientation feedback device 936 can automatically indicate to the surgeon that the inserter/impactor tool 916 is in the target orientation, such that the acetabular cup can be properly positioned and implanted for added convenience and accuracy.

As represented in FIG. 29, the orientation feedback device 936 can include an audible feedback device 938 that emits an audible feedback signal. For instance, the audible feedback device 938 can include a speaker that emits a preprogrammed sound when the inserter/impactor tool 916 is in the target orientation. Furthermore, the orientation feedback device 936 can include a visual feedback device 940 that emits a visual feedback signal. For instance, the visual feedback device 940 can include one or more lights, such as LED lights, for emitting a preprogrammed light pattern when the inserter/impactor tool 916 is in the target orientation. An embodiment of the visual feedback device 940 is described above in connection with the LEDs 804 and 803 of the electronic positioner 800. Additionally, the orientation feedback device 936 can include a tactile feedback device that selectively emits a tactile feedback signal when the inserter/impactor tool 916 is in the target orientation. For instance, the tactile feedback device 942 can include a vibration motor that selectively vibrates the housing 926 and the inserter/impactor tool 916 when the inserter/impactor tool 916 is in the target orientation.

It will be appreciated that the orientation feedback device 936 can provide any suitable feedback signal, including combinations of visual, audible and tactile feedback. Also, it will be appreciated that the feedback signal can be seen, heard, and felt simultaneously, and this redundancy can increase accuracy and convenience.

The electronic positioner 900 (or 800) can include a controller 946. The controller 946 can include various components, such as a microprocessor, memory, and the like. The controller 946 can be in communication with the orientation sensor 934 and the orientation feedback device 936. Accordingly, the controller 946 can cause the orientation feedback device 936 to selectively provide the respective orientation feedback signal(s) when the actual orientation of the inserter/impactor tool 916 detected by the orientation sensor 934 is substantially equal to a predetermined target orientation of the inserter/impactor tool 916.

The electronic positioner 900 (or 800) can include an impact sensor 947 to help the surgeon determine more accurately and conveniently when the acetabular cup 280 is fully seated in the acetabulum 82 of the patient. The impact sensor 947 can detect an actual impact effect on the inserter/impactor tool 916. For instance, the impact sensor 947 can be configured to detect an actual impact force F; on the head 920 of the inserter/impactor tool 916. The impact sensor 947 can also detect an actual displacement of the inserter/impactor tool 916 when the load $F_i$ is applied to the head 920. In addition, the impact sensor 947 can detect an actual acoustic effect of the impact when the load $F_i$ is applied. It will be appreciated that the impact sensor 947 can be configured to detect any suitable effect of applying the load $F_i$. The impact sensor 947 can include any suitable component, such as an accelerometer and/or a piezoelectric sensor, for detecting the actual impact effect. It will be appreciated that the orientation sensor 934 and the impact sensor 947 can rely, at least in part, on some of the same components, such as a common accelerometer, for the respective functions.

With continued reference to FIGS. 28 and 29, the electronic positioner 900 (or 800) can include an impact feedback device 948. Generally, the impact feedback device 948 can provide a feedback signal when the actual effect of applying the load $F_i$ detected by the impact sensor 947 substantially matches a predetermined target impact effect. More specifically, the surgeon can predetermine a target impact effect (e.g., a predetermined impact force $F_i$, an amount of displacement, an acoustic effect, etc.) that correlates to a condition in which the acetabular cup 280 is fully seated in the acetabulum 82 of the patient. Then, the controller 946 can cause the impact feedback device 948 to provide the respective feedback signal when the actual impact effect substantially matches the predetermined target impact effect. Thus, the impact feedback device 948 can inform the surgeon that the acetabular cup 280 has been fully seated into the acetabulum 82 of the patient.

It will be appreciated that the impact feedback device 948 can include any suitable device, such as an audible feedback device 950, a visual feedback device 952, and/or a tactile feedback device 954. The audible feedback device 950 can provide an audible feedback signal, and can include a speaker or any other suitable device for providing an audible feedback signal. The visual feedback device 952 can provide a visual feedback signal, and can include one or more lights, such as LED lights, for providing a visual feedback signal. Also, the tactile feedback device 954 can provide a tactile feedback signal and can include a vibration motor that selectively provides a tactile feedback signal.

In some embodiments, the electronic positioner 900 (or 800) can include an input device 941 for manually setting the target orientation of the inserter/impactor tool 916. More specifically, the input device 941 can include buttons, dials, a display, and other features for setting a target inclination angle, a target anteversion angle, or any other setting for the orientation of the alignment axis A. The input device 41 can be integrally coupled to the housing 926, and/or the input device 941 can be separate and remote from the housing 926. For example, as shown in FIG. 28, the input device 941 can include a wireless transmitter 943, and the housing 926 can include a wireless receiver 945. The receiver 945 receives wireless signals from the transmitter 943 to thereby set the target orientation of the alignment axis A. In some embodiments, the input device 941 can include an alphanumeric keypad for manually inputting and setting a particular target orientation. Additional details about of the electronic positioner 900 can be found in patent publications 2010/0249657 and 2010/0249796, referenced above, and are or can be similarly incorporated in the electronic positioner 800.

Various patient-specific guides, secondary guides, reamers, guide handles, inserters, impactors, support devices, electronic positioners and other instruments can be used in various combinations and based on surgeon preferences or patient and preoperative or intraoperative circumstances for preparing an acetabulum and guiding and implanting an acetabular implant along a preoperatively determined alignment orientation. In this respect, tools and instrumentation providing redundant functionality and of different embodiments may provided to the surgeon in a kit or per surgeon's request. For example, more than one patient specific acetabular guide (100, 200) may be provided. Similarly, various support devices (400, 700), secondary guides (600, 600A, 600B), reamers (500, 500'), inserters and/or impactors (550, 916), adaptors or couplers, electronic positioners (800, 900) and other instruments described above can be provided and used in various combinations within the scope of the methods described herein.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An acetabular guide comprising:
a patient-specific engagement surface designed to be complementary and mateable with a corresponding surface of the patient's pelvic anatomy as determined during a pre-operative plan of the patient by a three-dimensional reconstruction of the anatomy of the patient using two-dimensional medical images, the patient-specific engagement surface having a first portion mateable with a portion of an acetabulum of the patient and the engagement surface includes a second portion mateable with a portion of a rim of the acetabulum of the patient;
a guiding element extending from the acetabular guide opposite to the first portion of engagement surface, the guiding element defining a bore designed to be oriented along an alignment axis for an acetabular implant when the acetabular guide is engaged to the acetabulum; and
first and second marker elements extending from a portion of the acetabular guide outside the acetabulum of the patient, the marker elements defining corresponding first and second bores for guiding first and second marker pins into a bone portion of the patient.

2. An acetabular guide comprising:
a patient-specific engagement surface designed to be complementary and mateable with a corresponding surface of the patient's pelvic anatomy as determined during a pre-operative plan of the patient by a three-dimensional reconstruction of the anatomy of the patient using two-dimensional medical images, the patient-specific engagement surface having a first portion mateable with a portion of an acetabulum of the patient;
a guiding element extending from the acetabular guide opposite to the first portion of engagement surface, the guiding element defining a bore designed to be oriented along an alignment axis for an acetabular implant when the acetabular guide is engaged to the acetabulum; and
first and second marker elements extending from a portion of the acetabular guide outside the acetabulum of the patient, the marker elements defining corresponding first and second bores for guiding first and second marker pins into a bone portion of the patient.

* * * * *